(12) United States Patent
Grant et al.

(10) Patent No.: US 11,672,583 B2
(45) Date of Patent: Jun. 13, 2023

(54) CRYOTHERAPY, THERMAL THERAPY, TEMPERATURE MODULATION THERAPY, AND PROBE APPARATUS THEREFOR

(71) Applicant: Monteris Medical Corporation, Plymouth, MN (US)

(72) Inventors: Mark A. Grant, Winnipeg (CA); Richard Tyc, Winnipeg (CA)

(73) Assignee: MONTERIS MEDICAL CORPORATION, Minnetonka, MN (US)

( * ) Notice: Subject to any disclaimer, the term of this patent is extended or adjusted under 35 U.S.C. 154(b) by 492 days.

(21) Appl. No.: 16/397,015

(22) Filed: Apr. 29, 2019

(65) Prior Publication Data
US 2019/0262057 A1 Aug. 29, 2019

Related U.S. Application Data

(63) Continuation of application No. 14/841,109, filed on Aug. 31, 2015, now Pat. No. 10,327,830.
(Continued)

(51) Int. Cl.
*A61B 18/02* (2006.01)
*A61B 18/04* (2006.01)
(Continued)

(52) U.S. Cl.
CPC ............ *A61B 18/02* (2013.01); *A61B 18/04* (2013.01); *A61B 18/082* (2013.01); *A61B 18/22* (2013.01);
(Continued)

(58) Field of Classification Search
CPC combination set(s) only.
See application file for complete search history.

(56) References Cited

U.S. PATENT DOCUMENTS 3,021,842 A 2/1962 Flood
3,139,990 A 7/1964 Jelatis et al.
(Continued)

FOREIGN PATENT DOCUMENTS

CA 1317641 C 5/1993
CA 2348867 A1 5/2000
(Continued)

OTHER PUBLICATIONS

European Examination Communication pursuant to Article 94(3) EPC, issued by the European Patent Office, regarding corresponding patent application Serial No. EP 16773825.1; dated Mar. 5, 2019; 8 pages.
(Continued)

*Primary Examiner* — Joseph A Stoklosa
*Assistant Examiner* — Adam J Avigan
(74) *Attorney, Agent, or Firm* — Fox Rothschild LLP

(57) ABSTRACT

A variable length interstitial probe apparatus includes: a probe for effecting thermal therapy and/or cryotherapy to a tissue; a flexible umbilical sheath permanently affixed to the probe, including at least one interface for supplying energy, cooling fluid, cooling gas, heating fluid, and/or heating gas to the probe; and an adjustable depth stop configured to slide along a length of a shaft region of the probe, and lock to the shaft region at a selected position. The adjustable depth stop is configured to engage a probe driver and/or a skull mount apparatus to stabilize positioning of the probe and to control a depth of entry of the probe into a patient. The probe may be configured to effect temperature modulation therapy, where processing circuitry activates a modulation pattern of thermal therapy emission and cryogenic therapy emission for applying a thermal dose to the tissue.

14 Claims, 25 Drawing Sheets

Related U.S. Application Data

(60) Provisional application No. 62/141,612, filed on Apr. 1, 2015.

(51) Int. Cl.

| | | |
|---|---|---|
| *A61B 18/08* | (2006.01) | |
| *A61B 18/20* | (2006.01) | |
| *A61B 18/22* | (2006.01) | |
| *A61N 7/02* | (2006.01) | |
| *A61B 18/00* | (2006.01) | |
| *A61B 90/00* | (2016.01) | |

(52) U.S. Cl.
CPC ............ *A61B 2018/00577* (2013.01); *A61B 2018/00738* (2013.01); *A61B 2018/0231* (2013.01); *A61B 2018/0262* (2013.01); *A61B 2018/046* (2013.01); *A61B 2018/20361* (2017.05); *A61B 2018/2266* (2013.01); *A61B 2090/036* (2016.02); *A61B 2090/3937* (2016.02); *A61N 7/022* (2013.01)

(56) References Cited

U.S. PATENT DOCUMENTS

| | | |
|---|---|---|
| 4,111,209 A | 9/1978 | Wolvek et al. |
| 4,233,979 A | 11/1980 | Naser |
| 4,360,028 A | 11/1982 | Barbier et al. |
| 4,378,016 A | 3/1983 | Loeb |
| 4,402,694 A | 9/1983 | Ash et al. |
| 4,568,559 A | 2/1986 | Nuwayser et al. |
| 4,609,174 A | 9/1986 | Nakatani |
| 4,622,953 A | 11/1986 | Gordon |
| 4,623,588 A | 11/1986 | Nuwayser et al. |
| 4,646,752 A | 3/1987 | Swann et al. |
| 4,671,254 A | 6/1987 | Fair |
| 4,733,660 A | 3/1988 | Itzkan |
| 4,733,929 A | 3/1988 | Brown |
| 4,832,024 A | 5/1989 | Boussignac et al. |
| 4,914,608 A | 4/1990 | LeBihan et al. |
| 4,986,628 A | 1/1991 | Lozhenko et al. |
| 5,059,415 A | 10/1991 | Neuwelt |
| 5,078,140 A | 1/1992 | Kwoh |
| 5,085,219 A | 2/1992 | Ortendahl et al. |
| 5,092,891 A | 3/1992 | Kummer et al. |
| 5,102,410 A | 4/1992 | Dressel |
| 5,116,344 A | 5/1992 | Sundqvist |
| 5,154,723 A | 10/1992 | Kubota et al. |
| 5,192,278 A | 3/1993 | Hayes et al. |
| 5,196,005 A | 3/1993 | Doiron et al. |
| 5,201,742 A | 4/1993 | Hasson |
| 5,207,669 A | 5/1993 | Baker et al. |
| 5,207,681 A | 5/1993 | Ghadjar et al. |
| 5,217,441 A | 6/1993 | Shichman |
| 5,222,953 A | 6/1993 | Dowlatshahi |
| 5,230,338 A | 7/1993 | Allen et al. |
| 5,242,438 A | 9/1993 | Saadatmanesh et al. |
| 5,246,436 A | 9/1993 | Rowe |
| 5,247,935 A | 9/1993 | Cline et al. |
| 5,263,956 A | 11/1993 | Nobles |
| 5,269,777 A | 12/1993 | Doiron et al. |
| 5,275,165 A | 1/1994 | Ettinger et al. |
| 5,281,213 A | 1/1994 | Milder et al. |
| 5,284,144 A | 2/1994 | Delannoy et al. |
| 5,291,890 A | 3/1994 | Cline et al. |
| 5,292,320 A | 3/1994 | Brown et al. |
| 5,307,144 A | 4/1994 | Hiroshi et al. |
| 5,307,812 A | 5/1994 | Hardy et al. |
| 5,312,351 A | 5/1994 | Gerrone |
| 5,320,617 A | 6/1994 | Leach |
| 5,323,779 A | 6/1994 | Hardy et al. |
| 5,327,884 A | 7/1994 | Hardy et al. |
| 5,343,543 A | 8/1994 | Novak, Jr. et al. |
| 5,344,418 A | 9/1994 | Ghaffari |
| 5,344,419 A | 9/1994 | Spears |
| 5,348,048 A | 9/1994 | Schirado et al. |
| 5,354,293 A | 10/1994 | Beyer et al. |
| 5,354,294 A | 10/1994 | Chou |
| 5,366,456 A | 11/1994 | Rink et al. |
| 5,368,031 A | 11/1994 | Cline et al. |
| 5,368,032 A | 11/1994 | Cline et al. |
| 5,370,649 A | 12/1994 | Gardetto et al. |
| 5,374,266 A | 12/1994 | Kataoka et al. |
| 5,387,220 A | 2/1995 | Pisharodi |
| 5,388,580 A | 2/1995 | Sullivan et al. |
| 5,409,493 A | 4/1995 | Greenberg |
| 5,433,717 A | 7/1995 | Rubinsky et al. |
| 5,443,068 A | 8/1995 | Cline et al. |
| 5,445,166 A | 8/1995 | Taylor |
| 5,454,794 A | 10/1995 | Narciso, Jr. et al. |
| 5,454,807 A | 10/1995 | Lennox et al. |
| 5,454,897 A | 10/1995 | Vaniglia |
| 5,469,353 A | 11/1995 | Pinsky et al. |
| 5,474,564 A | 12/1995 | Clayman et al. |
| 5,476,461 A | 12/1995 | Cho et al. |
| 5,490,840 A | 2/1996 | Uzgiris et al. |
| 5,492,122 A | 2/1996 | Button et al. |
| 5,496,308 A | 3/1996 | Brown et al. |
| 5,499,313 A | 3/1996 | Kleinerman |
| 5,509,917 A | 4/1996 | Cecchetti et al. |
| 5,526,814 A | 6/1996 | Cline et al. |
| 5,530,780 A | 6/1996 | Ohsawa |
| 5,534,000 A | 7/1996 | Bruce |
| 5,537,499 A | 7/1996 | Brekke |
| 5,553,618 A | 9/1996 | Suzuki et al. |
| 5,562,688 A | 10/1996 | Riza |
| 5,568,503 A | 10/1996 | Omori |
| 5,571,099 A | 11/1996 | Purcell, Jr. et al. |
| 5,589,233 A | 12/1996 | Law et al. |
| 5,590,653 A | 1/1997 | Aida et al. |
| 5,620,479 A | 4/1997 | Diederich |
| 5,632,767 A | 5/1997 | Sinofsky |
| 5,636,259 A | 6/1997 | Khutoryansky et al. |
| 5,638,819 A | 6/1997 | Manwaring et al. |
| 5,643,179 A | 7/1997 | Fujimoto |
| 5,647,361 A | 7/1997 | Damadian |
| 5,655,084 A | 8/1997 | Pinsky et al. |
| 5,657,760 A | 8/1997 | Ying et al. |
| 5,663,646 A | 9/1997 | Kuth et al. |
| 5,671,353 A | 9/1997 | Tian et al. |
| 5,672,171 A | 9/1997 | Andrus et al. |
| 5,672,172 A | 9/1997 | Zupkas |
| 5,695,501 A | 12/1997 | Carol et al. |
| 5,711,300 A | 1/1998 | Schneider et al. |
| 5,715,823 A | 2/1998 | Wood et al. |
| 5,716,369 A | 2/1998 | Riza |
| 5,719,975 A | 2/1998 | Wolfson et al. |
| 5,728,106 A | 3/1998 | Misko et al. |
| 5,733,277 A | 3/1998 | Pallarito |
| 5,735,846 A | 4/1998 | Panescu et al. |
| 5,749,362 A | 5/1998 | Funda et al. |
| 5,749,549 A | 5/1998 | Ashjaee |
| 5,752,962 A | 5/1998 | D'Urso |
| 5,762,066 A | 6/1998 | Law et al. |
| 5,769,790 A | 6/1998 | Watkins et al. |
| 5,772,657 A | 6/1998 | Hmelar et al. |
| 5,782,824 A | 7/1998 | Abela et al. |
| 5,785,704 A | 7/1998 | Bille et al. |
| 5,792,110 A | 8/1998 | Cunningham |
| 5,807,383 A | 9/1998 | Kolesa et al. |
| 5,814,008 A | 9/1998 | Chen et al. |
| 5,817,036 A | 10/1998 | Anthony et al. |
| 5,823,941 A | 10/1998 | Shaunnessey |
| 5,824,005 A | 10/1998 | Motamedi et al. |
| 5,830,209 A | 11/1998 | Savage et al. |
| 5,848,967 A | 12/1998 | Cosman |
| 5,855,582 A | 1/1999 | Gildenberg |
| 5,855,583 A | 1/1999 | Wang et al. |
| 5,861,020 A | 1/1999 | Schwarzmaier |
| 5,873,845 A | 2/1999 | Cline et al. |
| 5,874,955 A | 2/1999 | Rogowitz et al. |
| 5,876,342 A | 3/1999 | Chen et al. |
| 5,890,897 A | 4/1999 | Kruger et al. |
| 5,891,100 A | 4/1999 | Fleckenstein |

(56) References Cited

U.S. PATENT DOCUMENTS

| | | |
|---|---|---|
| 5,891,157 A | 4/1999 | Day et al. |
| 5,897,495 A | 4/1999 | Aida et al. |
| 5,916,161 A | 6/1999 | Ishihara et al. |
| 5,928,145 A | 7/1999 | Ocali et al. |
| 5,944,663 A | 8/1999 | Kuth et al. |
| 5,945,827 A | 8/1999 | Gronauer et al. |
| 5,947,958 A | 9/1999 | Woodard et al. |
| 5,949,929 A | 9/1999 | Hamm |
| 5,959,246 A | 9/1999 | Gretz |
| 5,961,466 A | 10/1999 | Anbar |
| 5,978,541 A | 11/1999 | Doiron et al. |
| 5,989,246 A | 11/1999 | Kaufmann et al. |
| 5,993,463 A | 11/1999 | Truwit |
| 6,004,315 A | 12/1999 | Dumont |
| 6,006,126 A | 12/1999 | Cosman |
| 6,019,724 A | 2/2000 | Gronningsaeter et al. |
| 6,022,309 A | 2/2000 | Celliers et al. |
| 6,039,728 A | 3/2000 | Berlien et al. |
| 6,047,216 A | 4/2000 | Carl et al. |
| 6,050,943 A | 4/2000 | Slayton et al. |
| 6,053,912 A | 4/2000 | Panescu et al. |
| 6,058,323 A | 5/2000 | Lemelson |
| 6,067,371 A | 5/2000 | Gouge et al. |
| 6,071,288 A | 6/2000 | Carol et al. |
| 6,081,533 A | 6/2000 | Laubach et al. |
| 6,086,532 A | 7/2000 | Panescu et al. |
| 6,106,516 A | 8/2000 | Massengill |
| 6,117,143 A | 9/2000 | Hynes et al. |
| 6,123,719 A | 9/2000 | Masychev |
| 6,128,522 A | 10/2000 | Acker et al. |
| 6,131,480 A | 10/2000 | Yoneyama |
| 6,132,437 A | 10/2000 | Omurtag et al. |
| 6,133,306 A | 10/2000 | Beal |
| 6,143,018 A | 11/2000 | Beuthan et al. |
| 6,148,225 A | 11/2000 | Kestler et al. |
| 6,151,404 A | 11/2000 | Pieper |
| 6,152,933 A | 11/2000 | Werp et al. |
| 6,159,150 A | 12/2000 | Yale et al. |
| 6,162,052 A | 12/2000 | Kokubu |
| 6,164,843 A | 12/2000 | Battocchio |
| 6,167,295 A | 12/2000 | Cosman |
| 6,179,831 B1 | 1/2001 | Bliweis |
| 6,195,579 B1 | 2/2001 | Carroll et al. |
| 6,206,873 B1 | 3/2001 | Paolini et al. |
| 6,206,885 B1 | 3/2001 | Ghahremani et al. |
| 6,206,890 B1 | 3/2001 | Truwit |
| 6,226,680 B1 | 5/2001 | Boucher et al. |
| 6,241,725 B1 | 6/2001 | Cosman |
| 6,246,200 B1 | 6/2001 | Blumenkranz et al. |
| 6,246,896 B1 | 6/2001 | Dumoulin et al. |
| 6,246,912 B1 | 6/2001 | Sluijter et al. |
| 6,254,043 B1 | 7/2001 | Schwarzler |
| 6,263,229 B1 | 7/2001 | Atalar et al. |
| 6,267,769 B1 | 7/2001 | Truwit |
| 6,267,770 B1 | 7/2001 | Truwit |
| 6,280,384 B1 | 8/2001 | Loeffler |
| 6,283,958 B1 | 9/2001 | Vogl et al. |
| 6,283,988 B1 | 9/2001 | Laufer et al. |
| 6,286,795 B1 | 9/2001 | Johnson |
| 6,293,282 B1 | 9/2001 | Lemelson |
| 6,320,928 B1 | 11/2001 | Vaillant et al. |
| 6,321,266 B1 | 11/2001 | Yokomizo et al. |
| 6,332,891 B1 | 12/2001 | Himes |
| 6,334,847 B1 | 1/2002 | Fenster et al. |
| 6,353,445 B1 | 3/2002 | Babula et al. |
| 6,355,028 B2 | 3/2002 | Castaneda et al. |
| 6,368,329 B1 | 4/2002 | Truwit |
| 6,368,330 B1 | 4/2002 | Hynes et al. |
| 6,397,098 B1 | 5/2002 | Uber, III et al. |
| 6,398,778 B1 | 6/2002 | Gu et al. |
| 6,409,722 B1 | 6/2002 | Hoey et al. |
| 6,413,253 B1 | 7/2002 | Koop et al. |
| 6,413,263 B1 | 7/2002 | Lobdill et al. |
| 6,416,520 B1 | 7/2002 | Kynast et al. |
| 6,418,337 B1 | 7/2002 | Torchia et al. |
| 6,419,648 B1 | 7/2002 | Vitek et al. |
| 6,423,057 B1 | 7/2002 | He et al. |
| 6,423,077 B2 | 7/2002 | Carol et al. |
| 6,425,867 B1 | 7/2002 | Vaezy et al. |
| 6,440,127 B2 | 8/2002 | McGovern et al. |
| 6,447,505 B2 | 9/2002 | McGovern et al. |
| 6,451,015 B1 | 9/2002 | Rittman, III et al. |
| 6,454,774 B1 | 9/2002 | Fleckenstein |
| 6,461,314 B1 | 10/2002 | Pant et al. |
| 6,464,690 B1 | 10/2002 | Castaneda et al. |
| 6,464,691 B1 | 10/2002 | Castaneda et al. |
| 6,464,694 B1 | 10/2002 | Massengill |
| 6,468,238 B1 | 10/2002 | Hawkins et al. |
| 6,488,697 B1 | 12/2002 | Ariura et al. |
| 6,491,699 B1 | 12/2002 | Henderson et al. |
| 6,501,978 B2 | 12/2002 | Wagshul et al. |
| 6,506,154 B1 | 1/2003 | Ezion et al. |
| 6,506,171 B1 | 1/2003 | Vitek et al. |
| 6,507,747 B1 | 1/2003 | Gowda et al. |
| 6,510,241 B1 | 1/2003 | Vaillant et al. |
| 6,522,142 B1 | 2/2003 | Freundlich |
| 6,522,913 B2 | 2/2003 | Swanson et al. |
| 6,529,765 B1 | 3/2003 | Franck et al. |
| 6,542,767 B1 | 4/2003 | McNichols et al. |
| 6,543,272 B1 | 4/2003 | Vitek |
| 6,544,248 B1 | 4/2003 | Bass |
| 6,544,257 B2 | 4/2003 | Nagase et al. |
| 6,549,800 B1 | 4/2003 | Malar et al. |
| 6,551,274 B2 | 4/2003 | Heiner |
| 6,554,826 B1 | 4/2003 | Deardorff |
| 6,558,375 B1 | 5/2003 | Sinofsky et al. |
| 6,559,644 B2 | 5/2003 | Froundlich et al. |
| 6,575,969 B1 * | 6/2003 | Rittman, III ....... A61B 18/1482 606/41 |
| 6,577,888 B1 | 6/2003 | Chan et al. |
| 6,579,281 B2 | 6/2003 | Palmer et al. |
| 6,582,381 B1 | 6/2003 | Yehezkeli et al. |
| 6,582,420 B2 | 6/2003 | Castaneda et al. |
| 6,585,665 B1 | 7/2003 | Chapman et al. |
| 6,589,174 B1 | 7/2003 | Chopra et al. |
| 6,591,128 B1 | 7/2003 | Wu et al. |
| 6,603,988 B2 | 8/2003 | Dowlatshahi |
| 6,606,091 B2 | 8/2003 | Liang et al. |
| 6,606,513 B2 | 8/2003 | Lardo et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,623,490 B1 | 9/2003 | Crane et al. |
| 6,626,854 B2 | 9/2003 | Friedman et al. |
| 6,628,980 B2 | 9/2003 | Atalar et al. |
| 6,631,499 B1 | 10/2003 | Tsujii |
| 6,645,162 B2 | 11/2003 | Friedman et al. |
| 6,666,833 B1 | 12/2003 | Friedman et al. |
| 6,671,535 B1 | 12/2003 | McNichols et al. |
| 6,675,033 B1 | 1/2004 | Lardo et al. |
| 6,675,037 B1 | 1/2004 | Tsekos |
| 6,684,097 B1 | 1/2004 | Panel et al. |
| 6,695,871 B1 | 2/2004 | Maki et al. |
| 6,701,176 B1 | 3/2004 | Halperin et al. |
| 6,701,181 B2 | 3/2004 | Tang et al. |
| 6,705,994 B2 | 3/2004 | Vortman et al. |
| 6,716,215 B1 | 4/2004 | David et al. |
| 6,731,966 B1 | 5/2004 | Spigelman et al. |
| 6,735,461 B2 | 5/2004 | Vitek et al. |
| 6,741,883 B2 | 5/2004 | Gildenberg |
| 6,752,812 B1 | 6/2004 | Truwit |
| 6,755,849 B1 | 6/2004 | Gowda et al. |
| 6,770,031 B2 | 8/2004 | Hynynen et al. |
| 6,773,408 B1 | 8/2004 | Acker et al. |
| 6,782,288 B2 | 8/2004 | Truwit et al. |
| 6,790,180 B2 | 9/2004 | Vitek |
| 6,801,643 B2 | 10/2004 | Pieper |
| 6,823,216 B1 | 11/2004 | Salomir et al. |
| 6,825,838 B2 | 11/2004 | Smith et al. |
| 6,843,793 B2 | 1/2005 | Brock et al. |
| 6,845,193 B2 | 1/2005 | Loeb et al. |
| 6,893,447 B2 | 5/2005 | Dominguez et al. |

(56) References Cited

U.S. PATENT DOCUMENTS

| | | |
|---|---|---|
| 6,898,454 B2 | 5/2005 | Atalar et al. |
| 6,902,569 B2 | 6/2005 | Parmer et al. |
| 6,904,307 B2 | 6/2005 | Karmarkar et al. |
| 6,986,764 B2 | 1/2006 | Davenport et al. |
| 7,033,367 B2 | 4/2006 | Ghahremani et al. |
| 7,072,704 B2 | 7/2006 | Bucholz |
| 7,074,233 B1 | 7/2006 | Gowda et al. |
| 7,097,641 B1 | 8/2006 | Arless et al. |
| 7,123,255 B2 | 10/2006 | Frousett et al. |
| 7,128,711 B2 | 10/2006 | Medan et al. |
| 7,133,714 B2 | 11/2006 | Karmarkar et al. |
| 7,163,542 B2 | 1/2007 | Ryan |
| 7,164,940 B2 | 1/2007 | Hareyama et al. |
| 7,166,458 B2 | 1/2007 | Ballerstadt et al. |
| 7,167,741 B2 | 1/2007 | Torchia et al. |
| 7,167,760 B2 | 1/2007 | Dawant et al. |
| 7,175,596 B2 | 2/2007 | Vitek et al. |
| 7,226,414 B2 | 6/2007 | Ballerstadt et al. |
| 7,228,165 B1 | 6/2007 | Sullivan |
| 7,229,451 B2 | 6/2007 | Day et al. |
| 7,235,084 B2 | 6/2007 | Skakoon et al. |
| 7,235,089 B1 | 6/2007 | McGuckin, Jr. |
| 7,236,812 B1 | 6/2007 | Ballerstadt et al. |
| 7,236,816 B2 | 6/2007 | Kumar et al. |
| 7,270,656 B2 | 9/2007 | Gowda et al. |
| 7,274,847 B2 | 9/2007 | Gowda et al. |
| 7,280,686 B2 | 10/2007 | Hornegger et al. |
| 7,292,719 B2 | 11/2007 | Amon |
| 7,315,167 B2 | 1/2008 | Bottcher |
| 7,321,374 B2 | 1/2008 | Naske |
| 7,344,529 B2 | 3/2008 | Torchia et al. |
| RE40,279 E | 4/2008 | Sluijter et al. |
| 7,366,561 B2 | 4/2008 | Mills et al. |
| 7,371,210 B2 | 5/2008 | Brock et al. |
| 7,377,900 B2 | 5/2008 | Vitek et al. |
| 7,412,141 B2 | 8/2008 | Gowda et al. |
| 7,450,985 B2 | 11/2008 | Meloy |
| 7,463,801 B2 | 12/2008 | Brekke et al. |
| 7,479,139 B2 | 1/2009 | Cytron et al. |
| 7,489,133 B1 | 2/2009 | Keidl et al. |
| 7,494,489 B2 | 2/2009 | Roh |
| 7,507,244 B2 | 3/2009 | Dinkler |
| 7,519,210 B2 | 4/2009 | Hirsch et al. |
| 7,521,930 B2 | 4/2009 | Li et al. |
| 7,535,794 B2 | 5/2009 | Prus et al. |
| 7,551,953 B2 | 6/2009 | Lardo et al. |
| 7,561,906 B2 | 7/2009 | Atalar et al. |
| 7,599,729 B2 | 10/2009 | Atalar et al. |
| 7,602,190 B2 | 10/2009 | Piferi et al. |
| 7,609,927 B2 | 10/2009 | Gowda et al. |
| 7,611,462 B2 | 11/2009 | Vortman et al. |
| 7,631,233 B2 | 12/2009 | Parris et al. |
| 7,634,119 B2 | 12/2009 | Tsougarakis et al. |
| 7,652,410 B2 | 1/2010 | Prus |
| 7,659,719 B2 | 2/2010 | Vaughan et al. |
| 7,661,162 B2 | 2/2010 | Soerensen et al. |
| 7,699,780 B2 | 4/2010 | Vitek et al. |
| 7,702,140 B2 | 4/2010 | Hirsch et al. |
| 7,706,858 B1 | 4/2010 | Green et al. |
| 7,717,853 B2 | 5/2010 | Nita |
| 7,736,371 B2 | 6/2010 | Schoepp |
| 7,778,682 B2 | 8/2010 | Kumar et al. |
| 7,792,566 B2 | 9/2010 | Roland et al. |
| 7,794,469 B2 | 9/2010 | Kao et al. |
| 7,801,587 B2 | 9/2010 | Webber et al. |
| 7,848,788 B2 | 12/2010 | Tulley et al. |
| 7,876,939 B2 | 1/2011 | Yankelevitz et al. |
| 7,925,328 B2 | 4/2011 | Urquhart et al. |
| 7,957,783 B2 | 6/2011 | Atalar et al. |
| 8,002,706 B2 | 8/2011 | Vortman et al. |
| 8,022,705 B2 | 9/2011 | Bogdanov |
| RE42,856 E | 10/2011 | Karmarkar et al. |
| 8,029,471 B1 | 10/2011 | Khan-Sahibzada et al. |
| 8,034,569 B2 | 10/2011 | Jackson et al. |
| 8,055,351 B2 | 11/2011 | Atalar et al. |
| 8,060,182 B2 | 11/2011 | He et al. |
| 8,068,893 B2 | 11/2011 | Guttman et al. |
| 8,088,067 B2 | 1/2012 | Vortman et al. |
| 8,094,900 B2 | 1/2012 | Steines et al. |
| 8,099,150 B2 | 1/2012 | Piferi et al. |
| 8,100,132 B2 | 1/2012 | Markstroem |
| 8,108,028 B2 | 1/2012 | Karmarkar |
| 8,114,068 B2 | 2/2012 | Rheinwald et al. |
| 8,116,843 B2 | 2/2012 | Dai et al. |
| 8,157,828 B2 | 4/2012 | Piferi |
| 8,165,658 B2 | 4/2012 | Waynik et al. |
| 8,175,677 B2 | 5/2012 | Sayler et al. |
| 8,190,237 B2 | 5/2012 | Driemel |
| 8,195,272 B2 | 6/2012 | Piferi et al. |
| 8,208,993 B2 | 6/2012 | Piferi et al. |
| 8,211,095 B2 | 7/2012 | Gowda et al. |
| 8,216,854 B2 | 7/2012 | Ballerstadt et al. |
| 8,221,427 B2 | 7/2012 | Roh |
| 8,224,420 B2 | 7/2012 | Mu et al. |
| 8,233,701 B2 | 7/2012 | Frakes et al. |
| 8,235,901 B2 | 8/2012 | Schmidt et al. |
| 8,251,908 B2 | 8/2012 | Vortman et al. |
| 8,267,938 B2 | 9/2012 | Murphy |
| 8,270,698 B2 | 9/2012 | Geiger |
| 8,285,097 B2 | 10/2012 | Griffin |
| 8,287,537 B2 | 10/2012 | Dinkler, II |
| 8,298,245 B2 | 10/2012 | Li et al. |
| 8,314,052 B2 | 11/2012 | Jackson |
| 8,315,689 B2 | 11/2012 | Jenkins et al. |
| 8,320,990 B2 | 11/2012 | Vij |
| 8,340,743 B2 | 12/2012 | Jenkins et al. |
| RE43,901 E | 1/2013 | Freundlich et al. |
| 8,343,138 B2 | 1/2013 | Asfora |
| 8,364,217 B2 | 1/2013 | Ballerstadt et al. |
| 8,368,401 B2 | 2/2013 | Levy et al. |
| 8,369,930 B2 | 2/2013 | Jenkins et al. |
| 8,374,677 B2 | 2/2013 | Piferi et al. |
| 8,380,277 B2 | 2/2013 | Atalar et al. |
| 8,387,220 B2 | 3/2013 | Ishikura et al. |
| 8,396,532 B2 | 3/2013 | Jenkins et al. |
| 8,404,495 B2 | 3/2013 | Ballerstadt et al. |
| 8,409,099 B2 | 4/2013 | Vitek et al. |
| 8,414,597 B2 | 4/2013 | Kao et al. |
| 8,425,424 B2 | 4/2013 | Zadicario et al. |
| 8,433,421 B2 | 4/2013 | Atalar et al. |
| 8,482,285 B2 | 7/2013 | Grissom et al. |
| 8,520,932 B2 | 8/2013 | Cool et al. |
| 8,548,561 B2 | 10/2013 | Vortman et al. |
| 8,548,569 B2 | 10/2013 | Piferi et al. |
| 8,608,672 B2 | 12/2013 | Vortman et al. |
| 8,617,073 B2 | 12/2013 | Prus et al. |
| RE44,726 E | 1/2014 | Parris et al. |
| RE44,736 E | 1/2014 | Karmarkar et al. |
| 8,644,906 B2 | 2/2014 | Piferi et al. |
| 8,649,842 B2 | 2/2014 | Atalar et al. |
| 8,661,873 B2 | 3/2014 | Medan et al. |
| 8,688,226 B2 | 4/2014 | Atalar et al. |
| 8,728,092 B2 | 5/2014 | Qureshi et al. |
| 8,737,712 B2 | 5/2014 | Geiger |
| 8,979,871 B2 | 3/2015 | Tyc et al. |
| 9,333,038 B2 | 5/2016 | Torchia et al. |
| 9,387,042 B2 | 7/2016 | Torchia et al. |
| 2001/0003798 A1 | 6/2001 | McGovern et al. |
| 2002/0019641 A1 | 2/2002 | Truwit |
| 2002/0042605 A1 | 4/2002 | Castaneda et al. |
| 2002/0052610 A1 | 5/2002 | Skakoon et al. |
| 2002/0087148 A1 | 7/2002 | Brock et al. |
| 2002/0103459 A1 | 8/2002 | Sparks et al. |
| 2002/0169460 A1 | 11/2002 | Foster et al. |
| 2002/0177843 A1 | 11/2002 | Anderson et al. |
| 2003/0023236 A1 | 1/2003 | Gowda et al. |
| 2003/0060813 A1 | 3/2003 | Loeb et al. |
| 2003/0171741 A1 | 9/2003 | Ziebol et al. |
| 2003/0187371 A1 | 10/2003 | Vortman et al. |
| 2004/0059265 A1* | 3/2004 | Candy .............. G10K 11/34 601/2 |
| 2004/0073100 A1 | 4/2004 | Ballerstadt et al. |
| 2004/0075031 A1 | 4/2004 | Crain et al. |
| 2004/0082984 A1 | 4/2004 | Osorio et al. |

(56) References Cited

U.S. PATENT DOCUMENTS

| | | |
|---|---|---|
| 2004/0122446 A1 | 6/2004 | Solar |
| 2004/0123870 A1 | 7/2004 | Stamper et al. |
| 2004/0133190 A1 | 7/2004 | Hobart et al. |
| 2004/0134884 A1 | 7/2004 | Wei et al. |
| 2004/0158237 A1* | 8/2004 | Abboud ............... A61B 18/02 606/21 |
| 2004/0167542 A1 | 8/2004 | Solar et al. |
| 2004/0167543 A1 | 8/2004 | Mazzocchi et al. |
| 2004/0249261 A1 | 12/2004 | Torchia et al. |
| 2004/0267284 A1 | 12/2004 | Parmer et al. |
| 2005/0070920 A1 | 3/2005 | Solar et al. |
| 2005/0154378 A1 | 7/2005 | Teague et al. |
| 2006/0009749 A1 | 1/2006 | Weckwerth et al. |
| 2006/0089626 A1 | 4/2006 | Vlegele et al. |
| 2006/0122590 A1 | 6/2006 | Bliweis et al. |
| 2006/0122629 A1 | 6/2006 | Skakoon |
| 2006/0175484 A1 | 8/2006 | Wood et al. |
| 2006/0192319 A1 | 8/2006 | Solar |
| 2006/0195119 A1 | 8/2006 | Mazzocchi et al. |
| 2006/0206105 A1 | 9/2006 | Chopra et al. |
| 2006/0212044 A1 | 9/2006 | Bova et al. |
| 2006/0229641 A1 | 10/2006 | Gupta et al. |
| 2006/0241393 A1 | 10/2006 | Liu et al. |
| 2006/0265022 A1 | 11/2006 | John et al. |
| 2006/0287647 A1 | 12/2006 | Torchia et al. |
| 2007/0016039 A1 | 1/2007 | Vortman et al. |
| 2007/0043342 A1 | 2/2007 | Kleinberger |
| 2007/0088416 A1 | 4/2007 | Atalar et al. |
| 2007/0100346 A1 | 5/2007 | Wyss et al. |
| 2007/0106305 A1 | 5/2007 | Kao et al. |
| 2007/0149977 A1 | 6/2007 | Heavener |
| 2007/0191867 A1 | 8/2007 | Mazzocchi et al. |
| 2007/0197918 A1 | 8/2007 | Vitek et al. |
| 2007/0208352 A1 | 9/2007 | Henderson et al. |
| 2007/0225562 A1 | 9/2007 | Spivey et al. |
| 2007/0238978 A1 | 10/2007 | Kumar et al. |
| 2007/0239062 A1 | 10/2007 | Chopra et al. |
| 2007/0250077 A1 | 10/2007 | Skakoon et al. |
| 2007/0270717 A1 | 11/2007 | Tang et al. |
| 2007/0282404 A1 | 12/2007 | Cottrell et al. |
| 2008/0002927 A1 | 1/2008 | Furnish |
| 2008/0027463 A1 | 1/2008 | Labadie et al. |
| 2008/0033278 A1 | 2/2008 | Assif |
| 2008/0033292 A1 | 2/2008 | Shafran |
| 2008/0046122 A1 | 2/2008 | Manzo et al. |
| 2008/0077159 A1 | 3/2008 | Madhani et al. |
| 2008/0097187 A1 | 4/2008 | Gielen et al. |
| 2008/0114340 A1 | 5/2008 | Fox et al. |
| 2008/0123921 A1 | 5/2008 | Gielen et al. |
| 2008/0123922 A1 | 5/2008 | Gielen et al. |
| 2008/0195085 A1 | 8/2008 | Loeb |
| 2008/0208034 A1 | 8/2008 | Yang et al. |
| 2008/0242978 A1 | 10/2008 | Simon et al. |
| 2008/0243142 A1 | 10/2008 | Gildenberg |
| 2008/0243218 A1 | 10/2008 | Bottomley et al. |
| 2008/0255583 A1 | 10/2008 | Gielen et al. |
| 2008/0262584 A1 | 10/2008 | Bottomley et al. |
| 2008/0269588 A1 | 10/2008 | Csavoy et al. |
| 2008/0269602 A1 | 10/2008 | Csavoy et al. |
| 2008/0287917 A1 | 11/2008 | Cunningham |
| 2008/0306375 A1 | 12/2008 | Sayler et al. |
| 2009/0012509 A1 | 1/2009 | Csavoy et al. |
| 2009/0018446 A1 | 1/2009 | Medan et al. |
| 2009/0048588 A1 | 2/2009 | Peng et al. |
| 2009/0048606 A1 | 2/2009 | Tipirneni et al. |
| 2009/0082783 A1 | 3/2009 | Piferi |
| 2009/0088623 A1 | 4/2009 | Vortman et al. |
| 2009/0099045 A1 | 4/2009 | Jackson et al. |
| 2009/0112082 A1 | 4/2009 | Piferi et al. |
| 2009/0118610 A1 | 5/2009 | Karmarkar et al. |
| 2009/0124398 A1 | 5/2009 | Thompson |
| 2009/0131783 A1 | 5/2009 | Jenkins et al. |
| 2009/0148493 A1 | 6/2009 | Ballerstadt et al. |
| 2009/0171184 A1 | 7/2009 | Jenkins et al. |
| 2009/0192487 A1 | 7/2009 | Broaddus et al. |
| 2009/0198309 A1 | 8/2009 | Gowda et al. |
| 2009/0204111 A1 | 8/2009 | Bissig et al. |
| 2009/0234368 A1 | 9/2009 | Gore |
| 2009/0240242 A1 | 9/2009 | Neuberger |
| 2009/0264876 A1 | 10/2009 | Roy et al. |
| 2009/0266760 A1 | 10/2009 | Jackson et al. |
| 2009/0275130 A1 | 11/2009 | Navran et al. |
| 2009/0287199 A1 | 11/2009 | Hanley et al. |
| 2009/0308400 A1 | 12/2009 | Wilson et al. |
| 2009/0326525 A1 | 12/2009 | Hixon et al. |
| 2010/0016930 A1 | 1/2010 | Gowda et al. |
| 2010/0022951 A1 | 1/2010 | Ferrera et al. |
| 2010/0030076 A1 | 2/2010 | Vortman et al. |
| 2010/0041938 A1 | 2/2010 | Stoianovici et al. |
| 2010/0042112 A1 | 2/2010 | Qureshi et al. |
| 2010/0079580 A1 | 4/2010 | Waring, IV |
| 2010/0082035 A1 | 4/2010 | Keefer |
| 2010/0087336 A1 | 4/2010 | Jackson et al. |
| 2010/0146713 A1 | 6/2010 | Medan et al. |
| 2010/0179425 A1 | 7/2010 | Zadicario |
| 2010/0198052 A1 | 8/2010 | Jenkins et al. |
| 2010/0241036 A1 | 9/2010 | Vortman et al. |
| 2010/0305580 A1 | 12/2010 | Henderson et al. |
| 2010/0312094 A1 | 12/2010 | Guttman et al. |
| 2010/0312095 A1 | 12/2010 | Jenkins et al. |
| 2010/0312096 A1 | 12/2010 | Guttman et al. |
| 2010/0318002 A1 | 12/2010 | Prus et al. |
| 2011/0009734 A1 | 1/2011 | Foley et al. |
| 2011/0009828 A1 | 1/2011 | Prechtel et al. |
| 2011/0034800 A1 | 2/2011 | Vitek et al. |
| 2011/0040172 A1 | 2/2011 | Carpentier et al. |
| 2011/0046472 A1 | 2/2011 | Schmidt et al. |
| 2011/0046475 A1 | 2/2011 | Assif et al. |
| 2011/0066032 A1 | 3/2011 | Vitek et al. |
| 2011/0092848 A1 | 4/2011 | Hibner et al. |
| 2011/0118715 A1 | 5/2011 | Zerfas |
| 2011/0137147 A1 | 6/2011 | Skliar et al. |
| 2011/0141759 A1 | 6/2011 | Smith |
| 2011/0166447 A1 | 7/2011 | Windolf et al. |
| 2011/0175615 A1 | 7/2011 | Grissom et al. |
| 2011/0190787 A1 | 8/2011 | Sahni |
| 2011/0217665 A1 | 9/2011 | Walsh et al. |
| 2011/0224576 A1 | 9/2011 | Jackson et al. |
| 2011/0226260 A1 | 9/2011 | Eder et al. |
| 2011/0230753 A1 | 9/2011 | Mahon et al. |
| 2011/0237930 A1 | 9/2011 | Donaldson et al. |
| 2011/0238139 A1 | 9/2011 | Gowda et al. |
| 2011/0251528 A1 | 10/2011 | Canney et al. |
| 2011/0260728 A1 | 10/2011 | Biber et al. |
| 2011/0267059 A1 | 11/2011 | Shvartsberg et al. |
| 2011/0270075 A1 | 11/2011 | Vitek et al. |
| 2011/0270136 A1 | 11/2011 | Vitek et al. |
| 2011/0270366 A1 | 11/2011 | Mahon et al. |
| 2011/0295161 A1 | 12/2011 | Chopra et al. |
| 2011/0301450 A1 | 12/2011 | Hue et al. |
| 2011/0306054 A1 | 12/2011 | Jackson et al. |
| 2011/0319747 A1 | 12/2011 | Schmidt et al. |
| 2011/0319748 A1 | 12/2011 | Bronskill et al. |
| 2011/0319910 A1 | 12/2011 | Roelle et al. |
| 2012/0015359 A1 | 1/2012 | Jackson et al. |
| 2012/0029396 A1 | 2/2012 | Vortman et al. |
| 2012/0053573 A1 | 3/2012 | Alksnis |
| 2012/0059243 A1 | 3/2012 | Vortman et al. |
| 2012/0059335 A1 | 3/2012 | Bobo Sr. |
| 2012/0065629 A1 | 3/2012 | Elkins et al. |
| 2012/0070058 A1 | 3/2012 | Raju et al. |
| 2012/0071746 A1 | 3/2012 | Vortman et al. |
| 2012/0095364 A1 | 4/2012 | Bobo Sr. |
| 2012/0101412 A1 | 4/2012 | Vortman et al. |
| 2012/0108459 A1 | 5/2012 | Jackson et al. |
| 2012/0121533 A1 | 5/2012 | Jackson |
| 2012/0165225 A1 | 6/2012 | Stepanov et al. |
| 2012/0191020 A1 | 7/2012 | Vitek et al. |
| 2012/0197112 A1 | 8/2012 | McNichols |
| 2012/0245573 A1 | 9/2012 | Gowda et al. |
| 2013/0006095 A1 | 1/2013 | Jenkins et al. |
| 2013/0018430 A1 | 1/2013 | Murphy |
| 2013/0030408 A1 | 1/2013 | Piferi et al. |
| 2013/0034915 A1 | 2/2013 | Ballerstadt et al. |

(56) References Cited

U.S. PATENT DOCUMENTS

| | | |
|---|---|---|
| 2013/0035582 A1 | 2/2013 | Radulescu et al. |
| 2013/0041356 A1 | 2/2013 | Smith et al. |
| 2013/0053678 A1 | 2/2013 | Vitek et al. |
| 2013/0053867 A1 | 2/2013 | Gowda et al. |
| 2013/0060253 A1 | 3/2013 | Couture et al. |
| 2013/0085342 A1 | 4/2013 | Stefanchik et al. |
| 2013/0090639 A1 | 4/2013 | Atias et al. |
| 2013/0102883 A1 | 4/2013 | Piferi et al. |
| 2013/0116543 A1 | 5/2013 | Jenkins et al. |
| 2013/0119984 A1 | 5/2013 | Levy et al. |
| 2013/0123598 A1 | 5/2013 | Jenkins et al. |
| 2013/0131496 A1 | 5/2013 | Jenkins et al. |
| 2013/0150704 A1 | 6/2013 | Vitek et al. |
| 2013/0150756 A1 | 6/2013 | Vitek et al. |
| 2013/0157871 A1 | 6/2013 | Jackson |
| 2013/0158577 A1 | 6/2013 | Mahon et al. |
| 2013/0163841 A1 | 6/2013 | Geiger |
| 2013/0184563 A1 | 7/2013 | Driemel |
| 2013/0190607 A1 | 7/2013 | Biber et al. |
| 2013/0217950 A1 | 8/2013 | Partanen et al. |
| 2013/0245243 A1 | 9/2013 | Jackson |
| 2013/0245741 A1 | 9/2013 | Atalar et al. |
| 2013/0274778 A1 | 10/2013 | Mercier et al. |
| 2013/0325012 A1 | 12/2013 | Piferi et al. |
| 2014/0024909 A1 | 1/2014 | Vij et al. |
| 2014/0024925 A1 | 1/2014 | Piferi |
| 2014/0024927 A1 | 1/2014 | Piferi |
| 2014/0034377 A1 | 2/2014 | Vij |
| 2014/0046167 A1 | 2/2014 | Vij et al. |
| 2014/0046343 A1 | 2/2014 | Okazaki et al. |
| 2014/0066750 A1 | 3/2014 | Piferi et al. |
| 2014/0066953 A1 | 3/2014 | Keating et al. |
| 2014/0112095 A1 | 4/2014 | Medan et al. |
| 2014/0128881 A1 | 5/2014 | Tyc et al. |
| 2015/0148659 A1 | 5/2015 | Vahala |
| 2015/0265306 A1 | 9/2015 | Andrews et al. |
| 2015/0265353 A1 | 9/2015 | Andrews et al. |
| 2015/0265365 A1 | 9/2015 | Andrews et al. |
| 2015/0265366 A1 | 9/2015 | Andrews et al. |

FOREIGN PATENT DOCUMENTS

| | | |
|---|---|---|
| CA | 2370222 A1 | 10/2000 |
| CA | 2398967 A1 | 8/2001 |
| CA | 2.404352 A1 | 10/2001 |
| CA | 2403822 A1 | 10/2001 |
| CA | 2404352 A1 | 10/2001 |
| CA | 2482291 A1 | 10/2002 |
| CA | 2.587691 A1 | 5/2006 |
| CA | 2587691 A1 | 5/2006 |
| CA | 2606824 A1 | 11/2006 |
| CA | 2623453 A1 | 4/2007 |
| CA | 2679498 A1 | 9/2008 |
| CA | 2681367 A1 | 9/2008 |
| CA | 2695494 A1 | 12/2008 |
| CA | 2700523 A1 | 4/2009 |
| CA | 2700529 A1 | 4/2009 |
| CA | 2700531 A1 | 4/2009 |
| CA | 2700577 A1 | 4/2009 |
| CA | 2700607 A1 | 4/2009 |
| CA | 2704739 A1 | 4/2009 |
| CA | 2.648973 C | 7/2009 |
| CA | 2252431 C | 7/2009 |
| CA | 2648973 C | 7/2009 |
| CA | 2715015 A1 | 9/2009 |
| CA | 2748053 A1 | 4/2010 |
| CA | 2753397 A1 | 9/2010 |
| CA | 2372.001 C | 10/2010 |
| CA | 2372001 C | 10/2010 |
| CA | 2764677 A1 | 12/2010 |
| CA | 1317641 | 5/2011 |
| CA | 2487140 C | 9/2011 |
| CA | 2800238 A1 | 9/2011 |
| CA | 2482202 C | 7/2012 |
| CA | 2849106 A1 | 4/2013 |
| CA | 2575313 C | 7/2013 |
| CA | 2548.226 C | 1/2014 |
| CA | 2548226 C | 1/2014 |
| CN | 2620289 Y | 6/2004 |
| CN | 2748071 Y | 12/2005 |
| CN | 101040772 A | 9/2007 |
| CN | 101194853 A | 6/2008 |
| DE | 26 21 909 A1 | 12/1977 |
| DE | 2621909 A1 | 12/1977 |
| EP | 0 610 991 A2 | 8/1994 |
| EP | 0610991 A2 | 8/1994 |
| EP | 0 614 651 A1 | 9/1994 |
| EP | 0614651 A1 | 9/1994 |
| EP | 0 755 697 A2 | 1/1997 |
| EP | 0755697 A2 | 1/1997 |
| EP | 0844581 A2 | 5/1998 |
| EP | 1 046 377 A2 | 10/2000 |
| EP | 1046377 A2 | 10/2000 |
| EP | 0 844 581 B1 | 7/2007 |
| EP | 1 829 764 | 9/2007 |
| EP | 1 829 764 A2 | 9/2007 |
| EP | 1 455 672 81 | 5/2008 |
| EP | 1455672 B1 | 5/2008 |
| EP | 1 985 330 A1 | 10/2008 |
| JP | 54-88120 | 7/1979 |
| JP | 59-42165 | 3/1984 |
| JP | 60-154698 | 8/1985 |
| JP | 7-308393 | 11/1995 |
| JP | 7-328028 | 12/1995 |
| JP | 9-038220 | 2/1997 |
| JP | 10-155805 | 6/1998 |
| JP | 10-258066 | 9/1998 |
| JP | 11-253562 | 9/1999 |
| JP | 2000-000319 | 1/2000 |
| JP | 2000-000319 A | 1/2000 |
| JP | 2000-126316 | 5/2000 |
| JP | 2000-126316 A | 5/2000 |
| JP | 2002-543865 | 12/2002 |
| JP | 2002-543865 A | 12/2002 |
| JP | 54-88120 B2 | 5/2014 |
| JP | 59-42165 B2 | 6/2016 |
| WO | 90/05494 A1 | 5/1990 |
| WO | WO 90/05494 | 5/1990 |
| WO | 1992/010142 A1 | 6/1992 |
| WO | WO 1992/010142 | 6/1992 |
| WO | 93/20769 A1 | 10/1993 |
| WO | WO 93/20769 | 10/1993 |
| WO | 94/04220 A1 | 3/1994 |
| WO | WO 94/04220 | 3/1994 |
| WO | 1994/023308 A1 | 10/1994 |
| WO | WO 1994/023308 | 10/1994 |
| WO | 95/29737 A1 | 11/1995 |
| WO | WO 95/29737 | 11/1995 |
| WO | 1997/040396 A1 | 10/1997 |
| WO | WO 1997/040396 | 10/1997 |
| WO | 98/23214 A1 | 6/1998 |
| WO | WO 98/23214 | 6/1998 |
| WO | 98/51229 A1 | 11/1998 |
| WO | 98/52465 A1 | 11/1998 |
| WO | WO 98/51229 | 11/1998 |
| WO | WO 98/52465 | 11/1998 |
| WO | 99/51156 A1 | 10/1999 |
| WO | WO 99/51156 | 10/1999 |
| WO | 00/23000 A1 | 4/2000 |
| WO | WO 00/23000 | 4/2000 |
| WO | 2000/028895 A1 | 5/2000 |
| WO | WO 2000/028895 | 5/2000 |
| WO | 2000/032102 A1 | 6/2000 |
| WO | WO 2000/032102 | 6/2000 |
| WO | 2000/062672 A1 | 10/2000 |
| WO | 2000/064003 A2 | 10/2000 |
| WO | WO 2000/062672 | 10/2000 |
| WO | WO 2000/064003 | 10/2000 |
| WO | 00/67640 A2 | 11/2000 |
| WO | WO 00/67640 | 11/2000 |
| WO | 2001/006925 A1 | 2/2001 |
| WO | WO 2001/006925 | 2/2001 |
| WO | 2001/025810 A1 | 4/2001 |
| WO | WO 2001/025810 | 4/2001 |

(56) References Cited

FOREIGN PATENT DOCUMENTS

| | | |
|---|---|---|
| WO | 2001/035825 A1 | 5/2001 |
| WO | WO 2001/035825 | 5/2001 |
| WO | 2001/040819 A1 | 6/2001 |
| WO | WO 2001/040819 | 6/2001 |
| WO | 2001/056469 A2 | 8/2001 |
| WO | WO 2001/056469 | 8/2001 |
| WO | 2001/065490 A2 | 9/2001 |
| WO | WO 2001/065490 | 9/2001 |
| WO | 01/076498 A3 | 10/2001 |
| WO | 2001/073461 A2 | 10/2001 |
| WO | 2001/074241 A2 | 10/2001 |
| WO | WO 01/076498 A3 | 10/2001 |
| WO | WO 2001/073461 | 10/2001 |
| WO | WO 2001/074241 | 10/2001 |
| WO | 2001/080708 A2 | 11/2001 |
| WO | 2001/080709 A2 | 11/2001 |
| WO | 2001/082806 A1 | 11/2001 |
| WO | WO 2001/080708 | 11/2001 |
| WO | WO 2001/080709 | 11/2001 |
| WO | WO 2001/082806 | 11/2001 |
| WO | 2002/000093 A2 | 1/2002 |
| WO | 2002/000298 A1 | 1/2002 |
| WO | WO 2002/000093 | 1/2002 |
| WO | WO 2002/000298 | 1/2002 |
| WO | 2002/009812 A1 | 2/2002 |
| WO | WO 2002/009812 | 2/2002 |
| WO | 2002/024075 A1 | 3/2002 |
| WO | 2002/024094 A2 | 3/2002 |
| WO | WO 2002/024075 | 3/2002 |
| WO | WO 2002/024094 | 3/2002 |
| WO | 2002/043804 A1 | 6/2002 |
| WO | 2002/043805 A1 | 6/2002 |
| WO | 2002/044753 A2 | 6/2002 |
| WO | 2002/045073 A2 | 6/2002 |
| WO | WO 2002/043804 | 6/2002 |
| WO | WO 2002/043805 | 6/2002 |
| WO | WO 2002/044753 | 6/2002 |
| WO | WO 2002/045073 | 6/2002 |
| WO | 2002/051501 A1 | 7/2002 |
| WO | WO 2002/051501 | 7/2002 |
| WO | 2002/058791 A1 | 8/2002 |
| WO | WO 2002/058791 | 8/2002 |
| WO | 2002/083016 A1 | 10/2002 |
| WO | 2002/084316 A1 | 10/2002 |
| WO | 2002/085216 A1 | 10/2002 |
| WO | WO 2002/083016 | 10/2002 |
| WO | WO 2002/084316 | 10/2002 |
| WO | WO 2002/085216 | 10/2002 |
| WO | 2002/097466 A1 | 12/2002 |
| WO | 2002/103380 A1 | 12/2002 |
| WO | WO 2002/097466 | 12/2002 |
| WO | WO 2002/103380 | 12/2002 |
| WO | 2003/011160 A2 | 2/2003 |
| WO | WO 2003/011160 | 2/2003 |
| WO | 2003/017843 A1 | 3/2003 |
| WO | WO 2003/017843 | 3/2003 |
| WO | 2003/042707 A2 | 5/2003 |
| WO | WO 2003/042707 | 5/2003 |
| WO | 2003/048702 A1 | 6/2003 |
| WO | 2003/052444 A1 | 6/2003 |
| WO | WO 2003/048702 | 6/2003 |
| WO | WO 2003/052444 | 6/2003 |
| WO | 03/094759 A1 | 11/2003 |
| WO | 2003/097162 A2 | 11/2003 |
| WO | WO 03/094759 A1 | 11/2003 |
| WO | WO 2003/097162 | 11/2003 |
| WO | 2003/102614 A1 | 12/2003 |
| WO | WO 2003/102614 | 12/2003 |
| WO | 2004/056421 A1 | 7/2004 |
| WO | WO 2004/056421 | 7/2004 |
| WO | 2004/075722 A2 | 9/2004 |
| WO | WO 2004/075722 A2 | 9/2004 |
| WO | 2004/105624 A1 | 12/2004 |
| WO | 2004/103472 A1 | 12/2004 |
| WO | WO 2004/103472 | 12/2004 |
| WO | WO 2004/105624 | 12/2004 |
| WO | 2005/046451 A2 | 5/2005 |
| WO | 2005/046753 A2 | 5/2005 |
| WO | WO 2005/046451 A2 | 5/2005 |
| WO | WO 2005/046753 | 5/2005 |
| WO | 2006/014966 A2 | 2/2006 |
| WO | 2006/018686 A1 | 2/2006 |
| WO | WO 2006/014966 | 2/2006 |
| WO | WO 2006/018686 | 2/2006 |
| WO | 2006/021851 A1 | 3/2006 |
| WO | WO 2006/021851 | 3/2006 |
| WO | 2006/055554 A2 | 5/2006 |
| WO | WO 2006/055554 | 5/2006 |
| WO | 2006/119492 A2 | 11/2006 |
| WO | WO 2006/119492 | 11/2006 |
| WO | 2006/136912 A1 | 12/2006 |
| WO | WO 2006/136912 | 12/2006 |
| WO | 2007/047966 A2 | 4/2007 |
| WO | WO 2007/047966 | 4/2007 |
| WO | 2007/056458 A2 | 5/2007 |
| WO | 2007/060474 A1 | 5/2007 |
| WO | WO 2007/056458 A2 | 5/2007 |
| WO | WO 2007/060474 A1 | 5/2007 |
| WO | 2007/064937 A1 | 6/2007 |
| WO | WO 2007/064937 | 6/2007 |
| WO | 2007/085892 A2 | 8/2007 |
| WO | WO 2007/085892 | 8/2007 |
| WO | 2007/129166 A2 | 11/2007 |
| WO | WO 2007/129166 | 11/2007 |
| WO | 2008/015520 A1 | 2/2008 |
| WO | 2008/015521 A2 | 2/2008 |
| WO | 2008/015522 A1 | 2/2008 |
| WO | 2008/015523 A2 | 2/2008 |
| WO | WO 2008/015520 | 2/2008 |
| WO | WO 2008/015521 | 2/2008 |
| WO | WO 2008/015522 | 2/2008 |
| WO | WO 2008/015523 | 2/2008 |
| WO | 2008/070685 A2 | 6/2008 |
| WO | WO 2008/070685 | 6/2008 |
| WO | 2008/109864 A2 | 9/2008 |
| WO | 2008/115383 A2 | 9/2008 |
| WO | 2008/115426 A1 | 9/2008 |
| WO | WO 2008/109864 | 9/2008 |
| WO | WO 2008/115383 | 9/2008 |
| WO | WO 2008/115426 | 9/2008 |
| WO | WO-2008/134509 A1 | 11/2008 |
| WO | WO-2008/142686 A2 | 11/2008 |
| WO | 2008/153975 A2 | 12/2008 |
| WO | WO 2008/153975 | 12/2008 |
| WO | 2009/007847 A2 | 1/2009 |
| WO | WO 2009/007847 | 1/2009 |
| WO | 2009/042130 A2 | 4/2009 |
| WO | 2009/042131 A1 | 4/2009 |
| WO | 2009/042135 A2 | 4/2009 |
| WO | 2009/042136 A1 | 4/2009 |
| WO | 2009/042152 A1 | 4/2009 |
| WO | 2009/042155 A2 | 4/2009 |
| WO | 2009/042160 A1 | 4/2009 |
| WO | 2009/044276 A2 | 4/2009 |
| WO | WO 2009/042130 | 4/2009 |
| WO | WO 2009/042131 | 4/2009 |
| WO | WO 2009/042135 | 4/2009 |
| WO | WO 2009/042136 | 4/2009 |
| WO | WO 2009/042152 | 4/2009 |
| WO | WO 2009/042155 | 4/2009 |
| WO | WO 2009/042160 | 4/2009 |
| WO | WO 2009/044276 | 4/2009 |
| WO | 2009/067205 A1 | 5/2009 |
| WO | WO 2009/067205 | 5/2009 |
| WO | 2009/117069 A2 | 9/2009 |
| WO | WO 2009/117069 | 9/2009 |
| WO | 2009/124301 A1 | 10/2009 |
| WO | WO 2009/124301 | 10/2009 |
| WO | 2009/135198 A1 | 11/2009 |
| WO | WO 2009/135198 | 11/2009 |
| WO | WO-2010/017641 A1 | 2/2010 |
| WO | 2010/030373 A2 | 3/2010 |
| WO | WO 2010/030373 | 3/2010 |
| WO | 2010/034099 A1 | 4/2010 |

(56) References Cited

FOREIGN PATENT DOCUMENTS

| | | |
|---|---|---|
| WO | WO 2010/034099 | 4/2010 |
| WO | 2010/058292 A2 | 5/2010 |
| WO | 2010/058293 A2 | 5/2010 |
| WO | WO 2010/058292 | 5/2010 |
| WO | WO 2010/058293 | 5/2010 |
| WO | 2010/082135 A1 | 7/2010 |
| WO | WO 2010/082135 | 7/2010 |
| WO | 2010/087961 A2 | 8/2010 |
| WO | WO 2010/087961 | 8/2010 |
| WO | 2010/110929 A2 | 9/2010 |
| WO | WO 2010/110929 | 9/2010 |
| WO | 2010/119340 A1 | 10/2010 |
| WO | WO 2010/119340 | 10/2010 |
| WO | 2010/141102 A1 | 12/2010 |
| WO | 2010/143072 A1 | 12/2010 |
| WO | 2010/144402 A2 | 12/2010 |
| WO | 2010/144405 A2 | 12/2010 |
| WO | 2010/144419 A2 | 12/2010 |
| WO | 2010/148083 A2 | 12/2010 |
| WO | 2010/148088 A2 | 12/2010 |
| WO | WO 2010/141102 | 12/2010 |
| WO | WO 2010/143072 | 12/2010 |
| WO | WO 2010/144402 | 12/2010 |
| WO | WO 2010/144405 | 12/2010 |
| WO | WO 2010/144419 | 12/2010 |
| WO | WO 2010/148083 | 12/2010 |
| WO | WO 2010/148088 | 12/2010 |
| WO | 2011/013001 A1 | 2/2011 |
| WO | 2011/015949 A1 | 2/2011 |
| WO | 2011/021106 A2 | 2/2011 |
| WO | WO 2011/013001 | 2/2011 |
| WO | WO 2011/015949 | 2/2011 |
| WO | WO 2011/021106 | 2/2011 |
| WO | 2011/024074 A2 | 3/2011 |
| WO | 2011/028505 A1 | 3/2011 |
| WO | WO 2011/024074 | 3/2011 |
| WO | WO 2011/028505 | 3/2011 |
| WO | 2011/045669 A2 | 4/2011 |
| WO | WO 2011/045669 | 4/2011 |
| WO | 2011/058437 A1 | 5/2011 |
| WO | WO 2011/058437 | 5/2011 |
| WO | 2011/087495 A1 | 7/2011 |
| WO | 2011/090990 A2 | 7/2011 |
| WO | WO 2011/087495 | 7/2011 |
| WO | WO 2011/090990 | 7/2011 |
| WO | 2011/112249 A1 | 9/2011 |
| WO | 2011/112251 A1 | 9/2011 |
| WO | 2011/115664 A2 | 9/2011 |
| WO | WO 2011/112249 | 9/2011 |
| WO | WO 2011/112251 | 9/2011 |
| WO | WO 2011/115664 | 9/2011 |
| WO | 2011/130107 A2 | 10/2011 |
| WO | WO 2011/130107 | 10/2011 |
| WO | 2011/135455 A2 | 11/2011 |
| WO | 2011/135458 A2 | 11/2011 |
| WO | WO 2011/135455 | 11/2011 |
| WO | WO 2011/135458 | 11/2011 |
| WO | 2012/014074 A2 | 2/2012 |
| WO | WO 2012/014074 | 2/2012 |
| WO | 2012/038826 A1 | 3/2012 |
| WO | WO 2012/038826 | 3/2012 |
| WO | 2012/052847 A1 | 4/2012 |
| WO | WO 2012/052847 | 4/2012 |
| WO | WO-2012/057915 A1 | 5/2012 |
| WO | 2012/112829 A2 | 8/2012 |
| WO | 2012/116265 A2 | 8/2012 |
| WO | WO 2012/112829 | 8/2012 |
| WO | WO 2012/116265 | 8/2012 |
| WO | WO2013063027 A1 | 10/2012 |
| WO | 2012/154961 A2 | 11/2012 |
| WO | 2012147614 A1 | 11/2012 |
| WO | WO 2012/147614 A1 | 11/2012 |
| WO | WO 2012/154961 | 11/2012 |
| WO | 2013/028811 A1 | 2/2013 |
| WO | WO 2013/028811 | 2/2013 |
| WO | 2013/030671 A1 | 3/2013 |
| WO | WO 2013/030671 | 3/2013 |
| WO | 2013/049108 A2 | 4/2013 |
| WO | WO 2013/049108 | 4/2013 |
| WO | 2013/117991 A1 | 8/2013 |
| WO | 2013/117992 A1 | 8/2013 |
| WO | WO 2013/117991 | 8/2013 |
| WO | WO 2013/117992 | 8/2013 |
| WO | 2013/181008 A1 | 12/2013 |
| WO | WO 2013/181008 | 12/2013 |
| WO | 2014/014585 A1 | 1/2014 |
| WO | WO 2014/003855 A1 | 1/2014 |
| WO | WO-2014/003855 A1 | 1/2014 |
| WO | WO 2014/014585 | 1/2014 |
| WO | WO 2014003855 | * 1/2014 ............ A61B 19/00 |
| WO | 2014/039481 A1 | 3/2014 |
| WO | WO 2014/039481 | 3/2014 |
| WO | WO-2016/149125 A1 | 9/2016 |

OTHER PUBLICATIONS

Supplementary European Search Report, issued by the European Patent Office, regarding corresponding patent application Serial No. EP 16773825.1; dated Feb. 11, 2019; 8 pages.

Partial Supplementary European Search Report, issued by the European Patent Office, regarding corresponding patent application Serial No. EP16773825.1, dated Sep. 12, 2018. 14 pages.

Office Action dated Jul. 5, 2016 in Chinese Patent Application No. 201380043974.1.

U.S. Office Action dated Jun. 27, 2016 in U.S. Appl. No. 14/661,310, filed Mar. 18, 2015.

Lubowitz, "Thermal chondroplasty using the Smith & Nephew Dyonics Glider Articular Cartilage Probe," https://www.smith-nephew.com/global/surgicaltechniques/sports%20med/dyonics~lider_pre-shapedprobe_tg_10600072a.pdf, Jul. 2006, pp. 1-8.

International Search Report and Written Opinion dated Jun. 17, 2016 in PCT/US2016/024168 filed Mar. 25, 2016.

International Search Report and Written Opinion dated Jun. 10, 2013, in PCT/US13/32273.

Office Action dated Dec. 27, 2013, in Israeli Patent Application No. 210878.

International Preliminary Report on Patentability dated Feb. 15, 2011, in PCT/CA2009/01137, 8 pages.

International Preliminary Report on Patentability dated Feb. 15, 2011, in PCT/CA2009/01138, 5 pages.

Office Action dated Oct. 25, 2011, in Brazilian Patent Application No. PI-0214951-6 (English translation).

Office Action dated May 28, 2013, in Brazilian Patent Application No. PI-0214951-6 (English translation).

Office Action dated Nov. 1, 2012, in Japanese Patent Application No. 2011-522361 (with English-language translation).

Combined Chinese OA and Search Report dated Mar. 13, 2013, in Chinese Patent Application No. 200980131609.X.

Kahn et al., "MRI-Guided Laser-Induced Interstitial Thermotherapy of Cerebral Neoplasms," Journal of Computer Assisted Tomography, vol. 18, No. 4, pp. 519-532, Jul./Aug. 1994, Raven Press, Ltd., New York, NY.

Kahn et al., "In Vivo MRI Thermometry Using a Phase-Sensitive Sequence: Preliminary Experience During MRI-Guided Laser-Induced Interstitial Thermotherapy of Brain Tumors," Journal of Magnetic Resonance Imaging, vol. 8, No. 1, pp. 160-164, Williams & Wilkins, 1998, Baltimore, MD.

McNichols et al., "MR Thermometry-Based Feedback Control of Laser Interstitial Thermal Therapy at 980 nm," Lasers in Surgery and Medicine, 2004, 34: 48-55, Wiley-Liss, Inc.

Schwarzmaier et al., "MR-guided laser-induced interstitial thermotherapy of recurrent glioblastoma multiforme: Preliminary results in 16 patients," European Journal of Radiology, vol. 59, Issue 2, pp. 208-215, Aug. 2006.

Office Action dated Oct. 8, 2012, in Chinese Patent Application No. 200980131600.9 (with English-language translation).

Office Action dated Jul. 17, 2013, in Japanese Patent Application No. 2011-522361 (with English-language translation).

(56) References Cited

OTHER PUBLICATIONS

Office Action dated Jul. 29, 2013, in Japanese Patent Application No. 2011-522360 (with English-language translation).
Jerome Shaunnessey, Petition for General Supervisory Review by the Director under 37 CFR 1.181, Jul. 2014, 6 pages.
International Search Report dated Aug. 3, 2012 in PCT/IB2012/051716.
Office Action dated Nov. 1, 2012, in Japanese Patent Application No. 2011-522360 (with English Translation).
Castro et al. "Interstitial laaser phototherapy assisted by magnetic resonance imaging: A new technique for monitoring laser-tissue interaction" The Laryngoscope, vol. 100, Issue , pp. 541-547, May 1990 (abstract only).
Nabavi et al. "Neurosurgical procedures in a 0.5 tesla, open-configuration intraoperative MRI: planning, visualization, and navigation" Automedica, vol. 00, pp. 1-35, 2001.
T. Menovsky, et al., "Interstitial Laser Thermotherapy in Neurosurgery: A Review", Acta Neurochir (Wien) (1996) 138:1019-1026, 8 pages.
Ferenc A. Jolesz M.D., et al., "MRI-Guided Laser-Induced Interstitial Thermotherapy: Basic Principles", Harvard Medical School and Brigham and Women's Hospital, Department of Radiology, appears in: SPIE Institute on Laser-Induced Interstitial Thermotherapy (LITT), Jun. 22-23, 1995, 17 pages.
Thorsten Harth, et al., "Determination of Laser-Induced Temperature Distributions Using Echo-Shifted TurboFLASH", MRM 38:238-245 (1997), 8 pages.
Lawrence P. Panych, et al., "Effects Related to Temperature Changes during MR Imaging", JMRI, vol. 2, No. 1, Jan./Feb. 1992, pp. 69-74.
John De Poorter, "Noninvasive MRI Thermometry with the Proton Resonance Frequency Method: Study of Susceptibility Effects", MRM 34:359-367 (1995), 9 pages.
Ron Corbett, et al., "Noninvasive Measurements of Human Brain Temperature Using Volume-Localized Proton Magnetic Resonance Spectroscopy", Journal of Cerebral Blood Flow and Metabolism, vol. 17, No. 4, 1997, pp. 363-369.
Waldemar Wlodarczyk, et al., "Comparison of four magnetic resonance methods for mapping small temperature changes", Phys. Med. Biol. 44, 1999, pp. 607-624.
Carpentier, et al. "Real-Time Magnetic Resonance-Guided Laser Thermal Therapy For Focal Metastatic Brain Tumors", Operative Neurogurgery 1, vol. 63, 2008, pp. 21-39.
Carpentier, et al. "MR-Guided Laser Induced Thermal Therapy (LITT) for Recurrent Glioblastomas", Lasers in Surgery and Medicine, vol. 44, pp. 361-368, 2012.
Carpentier, et al. "Laser Thermal Therapy: Real-time MRI-guided and Computer-controlled Procedures for Metastatic Brain Tumors", Lasers in Surgery and Medicine, vol. 43, pp. 943-950, 2011.
Gewiese, et al. "Magenetic Resonance Imaging-Controlled Laser-Induced Interstitial Thermotherapy", Investigative Radiology, vol. 29, No. 3, pp. 345-351, 1994.
Ferenc A. Jolesz, MD, et al., "MR Imaging of Laser-Tissue Interactions", Magnetic Resonance Imaging, Radiology 1988; 168, pp. 249-253.
Yoshimi Anzai, MD, et al., "Nd:YAG Interstitial Laser Phototherapy Guided by Magnetic Resonance Imaging in an Ex Vivo Model: Dosimetry of Laser-MR-Tissue Interaction", Laryngoscope 101: Jul. 1991, pp. 755-760.
Harvey E. Cline, et al., "MR-Guided Focused Ultrasound Surgery", Journal of Computer Assisted Tomography, Nov./Dec. 1992, vol. 16, No. 6, pp. 956-965.
Harvey E. Cline, PhD, et al., "Focused US System for MR Imaging-guided Tumor Ablation" Magnetic Resonance Imaging, Radiology 1995; Mar. 1995, vol. 194, No. 3, pp. 731-737.
Kullervo Hynynen, PhD, et al., "A Clinical, Noninvasive, MR Imaging-monitored Ultrasound Surgery Method", Imaging & Therapeutic Technology, RadioGraphics 1996; Jan. 1996, vol. 16, No. 1, pp. 185-195.
Nobuhiko Hata, et al., "Computer-Assisted Intra-Operative Magnetic Resonance Imaging Monitoring of Interstitial Laser Therapy in the Brain: A Case Report", Journal of Biomedical Optics, Jul. 1998, vol. 3, No. 3, pp. 304-311.
Joachim Kettenbach, MD, et al., "Monitoring and Visualization Techniques for MR-Guided Laser Ablations in an Open MR System" Journal of Magnetic Resonance Imaging, Jul./Aug. 1998, vol. 8, No. 4, pp. 933-943.
Ferenc A. Jolesz, MD, et al., "Integration of Interventional MRI with Computer-Assisted Surgery", Journal of Magnetic Resonance Imaging, Jan. 2001;13(1), pp. 69-77.
Frederic C. Vimeux, et al., "Real-Time Control of Focused Ultrasound Heating Based on Rapid MR Thermometry", Investigative Radiology, Mar. 1999, vol. 34(3), pp. 190-193.
J. Delannoy, et al., "Hyperthermia system combined with a magnetic resonance imaging unit", Medical Physics, vol. 17, No. 5, Sep./Oct. 1990, pp. 855-860.
Zientara, Gary P., et al. "MRI monitoring of laser ablation using optical flow." Journal of Magnetic Resonance Imaging 8.6 (1998): 1306-1318.
Alan R. Bleier, et al., "Real-Time Magnetic Resonance Imaging of Laser Heat Deposition in Tissue", Magnetic Resonance in Medicine 21, 1991, pp. 132-137.
Kullervo Hynynen, et al., "Focused Ultrasound Thermal Surgery Guided and Monitored by Magnetic Resonance Imaging", Interventional Radiology, 1997, vol. 2, Third Edition, pp. 1811-1816 (with cover pages).
Ferenc A. Jolesz, "MR-guided thermal ablation of brain tumors", Interventional MR: Techniques and Clinical Experience, 1998, pp. 123-129 (with cover pages).
F.A. Jolesz, et al., "Image-Guided Neurosurgery with Intraoperative MRI", Interventional Magnetic Resonance Imaging, 1998, pp. 253-260 (with cover pages).
Kullervo Hynynen, et al., "Principles of MR-Guided Focused Ultrasound", Chapter 25, Interventional MRI, 1999, pp. 237-243 (with cover pages).
Masoud Panjehpour, PhD et al., "Nd:YAG Laser-Induced Interstitial Hyperthermia Using a Long Frosted Contact Probe", Lasers in Surgery and Medicine 10, 1990, pp. 16-24.
S. Bosman, et al., "Effect of percutaneous interstitial thermal laser on normal liver of pigs: sonographic and histopathological correlations", Br. J. Surg., May 1991, vol. 78, No. 5, pp. 572-575.
M. Fan, M.D., et al., "Interstitial 1.06 Nd:YAG Laser Thermotherapy for Brain Tumors Under Real-Time Monitoring of MRI: Experimental Study and Phase I Clinical Trial", Journal of Clinical Laser Medicine & Surgery, vol. 10, No. 5, 1992, pp. 355-361.
Office Action issued in Chinese Patent Application No. 200980131609.X dated Jan. 10, 2014.
Office Action dated Aug. 22, 2013, in Chinese Patent Application No. 200980131600.9 (with English-language translation).
Vogl et al. "Internally Cooled Power Laser for MR-guided Interstitial Laser-induced Thermotherapy of Liver Lesions: Initial Clinical Results," Radiology, vol. 209, No. 2. 1998, 381-385.
International Search Report dated Jul. 27, 2015 in PCT/US2015/021228 filed Mar. 18, 2015.
Written Opinion dated Jul. 27, 2015 in PCT/US2015/021228 filed Mar. 18, 2015.
Chinese Office Action dated Apr. 23, 2020 for Corresponding Appln No. CN201680020426.0, 15 pages.
Information about Related Patents and Patent Applications, see section 4 of the accompanying Information Disclosure Statement Letter, which concerns Related Patents and Patent Applications.
Lubowiiz, "Thermal chondroplasty using the Smith & Nephew Dyonics Glider Articular Carttilage Probe", Smith & Nephew (Jul. 2006), pp. 1-8.
International Search Reprot and Written Opinion dated Jun. 10, 2013, in Application No. PCT/US13/32273.
International Preliminary Reporton Patentability dated Feb. 15, 2011, in Application No. PCT/CA2009/001138 (5 pages).
Kahn et al., "MRI-Guided Laser-Induced Interstitial Thermotherapy of Cerebral Neoplasms," Journal of Computer Assisted Tomography (Jul./Aug. 1994), 18(4):519-532.

(56) References Cited

OTHER PUBLICATIONS

Kahn et al., "MRI-Guided Laser-Induced Interstitial Thermotherapy of Cerebral Neoplasms," J of Comp Assisted Tomography (Jul./Aug. 1994), 18(4):519-532.
Vogl et al., "Internally Cooled Power Laser for MR-guided Interstitial Laser-induced Thermotherapy of Liver Lesions Initial Clinical Results", in Radiology, 1998, 209: pp. 381-385.
Mcnichols et al., "MR Thermometry-Based Feedback Control of Laser Interstitial Thermal Therapy at 980 nm," Lasers in Surgery and Medicine (2004), 34:48-55.
Schwarzmaier et al., "MR-guided laser-induced interstitial thermotherapy of recurrent glioblastoma multiforme Preliminary results in 16 patients," European Journal of Radiology (Aug. 2006), 59(2):208-215.
International Search Report, dated Aug. 3, 2012 in Application No. PCT/IB2012/051716.
Supplementary European Search Report dated Oct. 18, 2013, in European Patent Application No. 09806277.1.
Castro et al. "Interstitial laaser phototherapy assisted by magnetic resonance imaging: A new technique for monitoring laser-tissue interaction" The Larvnaoscooe (May 1990), vol. 100(DD):541-547 (abstract only).
Nabavi et al. "Neurosurgical procedures in a 0.5 tesla, open-configuration intraoperative MRI: planning, visualization, and navigation" Automedica, vol. oo; pp. 1-35, 2001.
Menovsky et al., "Interstitial Laser Thermotherapy in Neurosurgery: A Review", Acta Neurochir (Wien) (1996) 138:1019-1026.
Jolesz M.D., et al., "MRI-Guided Laser-Induced Interstitial Thermotherapy: Basic Principles", Harvard Medical School and Brigham and Women's Hospital, Department of Radiology, appears in: SPIE Institute on Laser-Induced nterstitial Thermotherapy (LITT), Jun. 22-23, 1995 (17 pages).
Harth, et al., "Determination of Laser-Induced Temperature Distributions Using Echo-Shifted TurboFLASH", MRM (1997), 38:238-245.
Panych, et al., "Effects Related to Temperature Changes during MR Imaging", JMRI, (Jan./Feb. 1992,) 2(1):69-74.
De Poorter, "Noninvasive MRI Thermometry with the Proton Resonance Frequency Method: Study of Susceptibility Effects", MRM (1995), 34:359-367.
Corbett, et al., "Noninvasive Measurements of Human Brain Temperature Using Volume-Localized Proton Magnetic Resonance Spectroscopy", Journal of Cerebral Blood Flow and Metabolism (1997), 17(4):363-369.
Wlodarczyk, et al., "Comparison of four magnetic resonance methods for mapping small temperature changes", Phys. Med. Biol. (1999), 44:607-624.
Carpentier et al. "Real-Time Magnetic Resonance-Guided Laser Thermal Therapy For Focal Metastatic Brain Tumors", Operative Neurogurgery 1 (2008), 63:21-39.
Canney, et al. "A Multi-element Interstitial Ultrasound Applicator for the Thermal Therapy of Brain Tumors", Acoustical Society of America, Pt. 2, Aug. 2013, pp. 1647-1655.
Carpentier, et al. "MR-Guided Laser Induced Thermal Therapy (LITT) for Recurrent Glioblastomas", Lasers in Surgery and Medicine (2012), 44:361 368.
Carpentier, et al. "Laser Thermal Therapy: Real-time MRI-guided and Computer-controlled Procedures for Metastatic Brain Tumors", Lasers in Surgery and Medicine(2011), 43:943-950.
Gewiese, et al. "Magenetic Resonance Imaging-Controlled Laser-Induced Interstitial Thermotherapy", Investigative Radiology (1994), 29(3):345-351.
Jolesz, MD, et al., "MR Imaging of Laser-Tissue Interactions", Magnetic Resonance Imaging, Radiology (1988) 168:249-253.
Anzai, MD, et al., "Nd:YAG Interstitial Laser Phototherapy Guided by Magnetic Resonance Imaging in an Ex Vivo Model: Dosimetry of Laser-MR-Tissue Interaction", Laryngoscope 101: Jul. 1991, pp. 755-760.
Cline, et al., "MR-Guided Focused Ultrasound Surgery", Journal of Computer Assisted Tomography, (Nov./Dec. 1992), 16(6):956-965.
Cline, PhD, et al.. "Focused US System for MR Imaging-guided Tumor Ablation" Magnetic Resonance Imaging, Radiology 1995; 194(3):731-737.
Hynynen, PhD, et al, "A Clinical, Noninvasive, MR Imaging-monitored Ultrasound Surgery Method". Imaging & Therapeutic Technology, RadioGraphics 1996, 16(1):185-195.
Hata, et al., "Computer-Assisted Intra-Operative Magnetic Resonance Imaging Monitoring of Interstitial Laser Therapy in the Brain: A Case Report", Journal of Biomedical Optics. (Jul. 1998), 3(3):304-311.
Kettenbach, MD, et al., "Monitoring and Visualization Techniques for MR-Guided Laser Ablations in an Open MR System" Journal of Magnetic Resonance Imaging (Jul./Aug. 1998), 8(4):933-943.
Jolesz, MD, et al., "Integration of Interventional MRI with Computer-Assisted Surgery", Journal of Magnetic Resonance Imaging (Jan. 2001), 13(1):69-77.
Vimeux, et al., "Real-Time Control of Focused Ultrasound Heating Based on Rapid MR Thermometry", Investigative Radiology (Mar. 1999), 34(3):190-193.
Delannoy, et al., "Hyperthermia system combined with a magnetic resonance imaging unit", Medical Physics (Sep./Oct. 1990), 17(5):855-860.
Zientara et al. "MRI monitoring of laser ablation using optical flow." Journal of Magnetic Resonance Imaging 8.6 (1998), pp. 1306-1318.
Bleier, et al., "Real-Time Magnetic Resonance Imaging of Laser Heat Deposition in Tissue", Magnetic Resonance in Medicine (1991), 21:132-137.
Hynynen et al., "Focused Ultrasound Thermal Surgery Guided and Monitored by Magnetic Resonance Imaging", Interventional Radiology, Third Edition (1997), 2:1811-1816 (with cover pages).
Jolesz, "MR-guided thermal ablation of brain tumors", Interventional MR: Techniques and Clinical Experience (1998), pp. 123-129 (with cover pages).
Jolesz et al., "Image-Guided Neurosurgery with Intraoperative MRI", Interventional Magnetic Resonance Imaging (1998), pp. 253-260 (with cover pages).
Hynynen et al., "Principles of MR-Guided Focused Ultrasound", Interventional MRI (1999), Chapter 25, pp. 237-243 (with cover pages).
Panjehpour, PhD et al., "Nd:YAG Laser-Induced Interstitial Hyperthermia Using a Long Frosted Contact Probe", Lasers in Surgery and Medicine (1990), 10:16-24.
Bosman et al., "Effect of percutaneous interstitial thermal laser on normal liver of pigs: sonographic and histopathological correlations", Br. J. Surg. (May 1991), 78(5):572-575.
Fan, M.D., et al., "Interstitial 1.06 Nd:YAG Laser Thermotherapy for. Brain Tumors Under Real-Time Monitoring of MRI: Experimental Study and Phase I Clinical Trial", Journal of Clinical Laser Medicine & Surgery (1992), 10(5):355-361.
International Search Report and Written Opinion dated Jul. 27, 2015 in Application No. PCT/US2015/021228.

\* cited by examiner

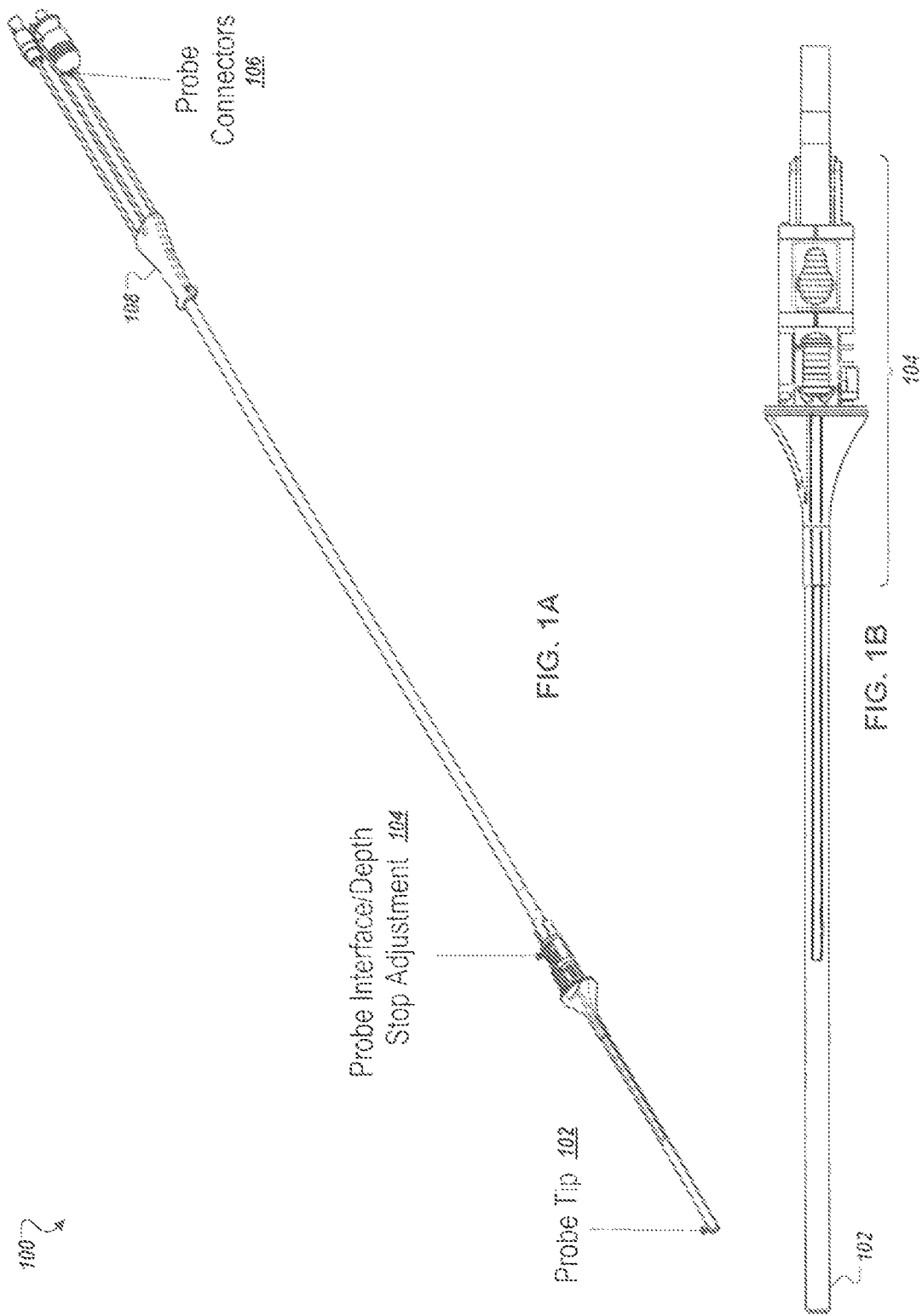

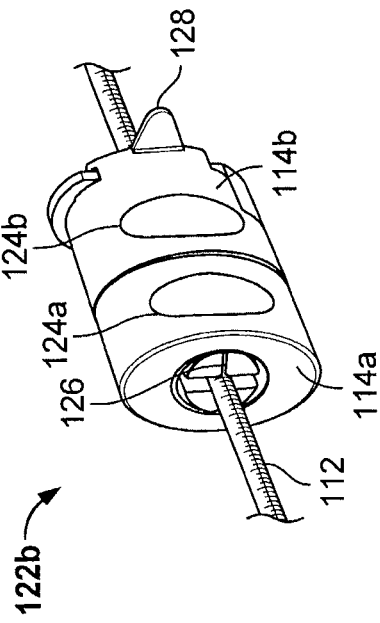
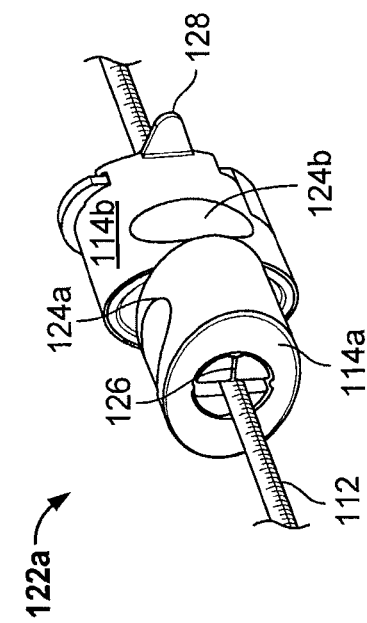
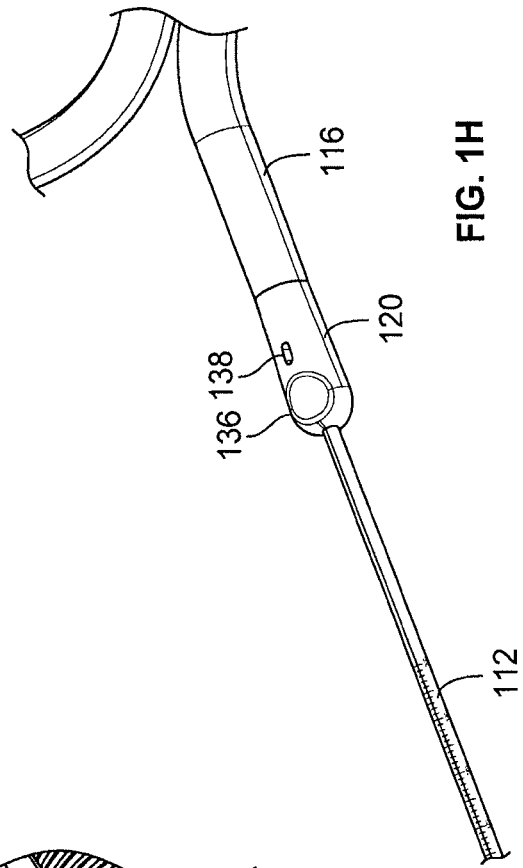
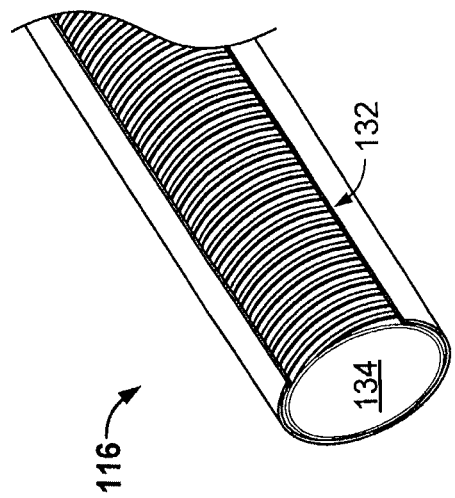

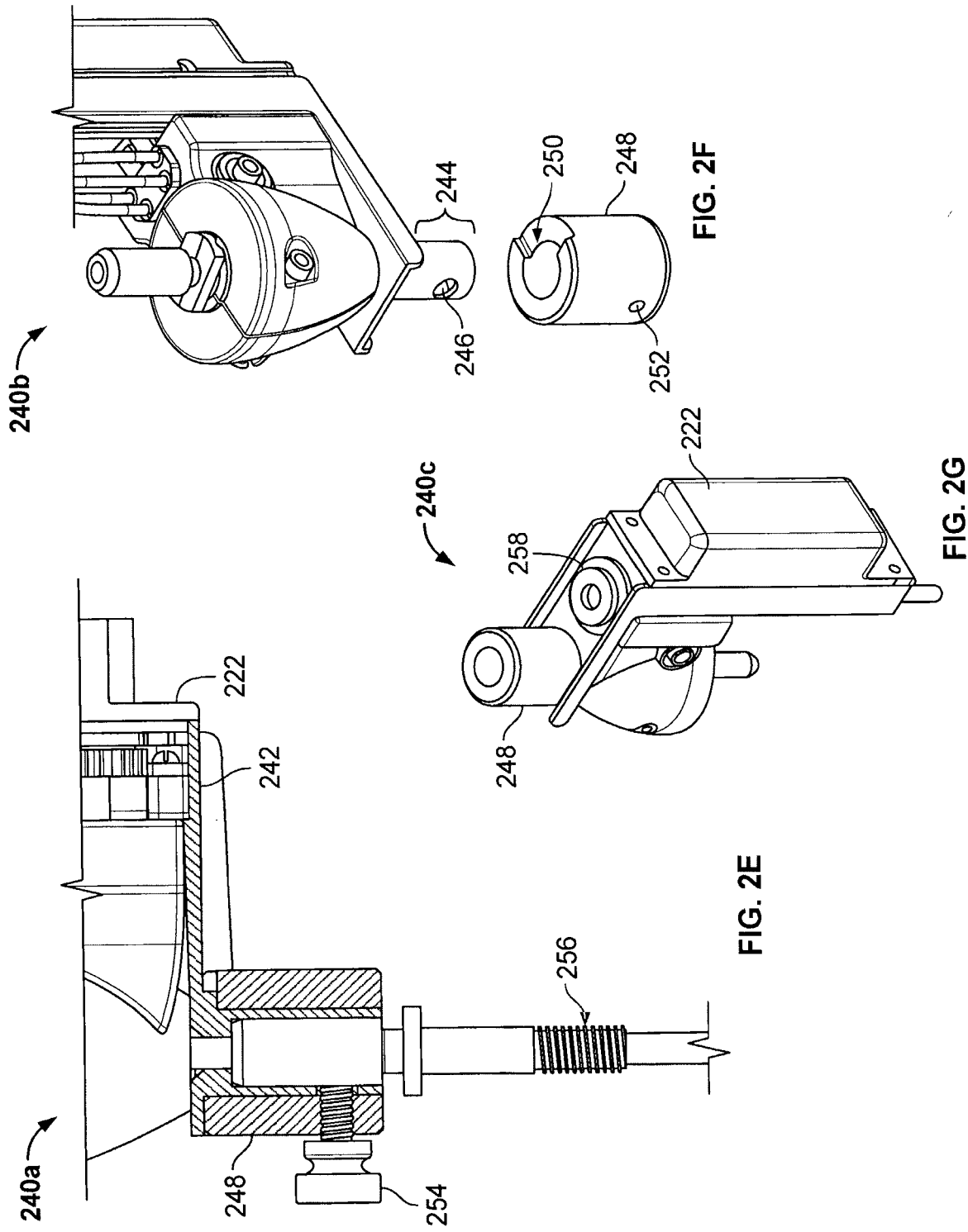

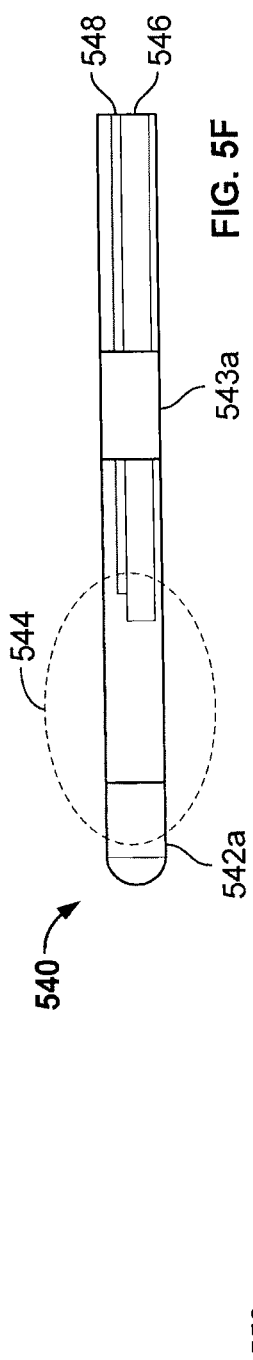
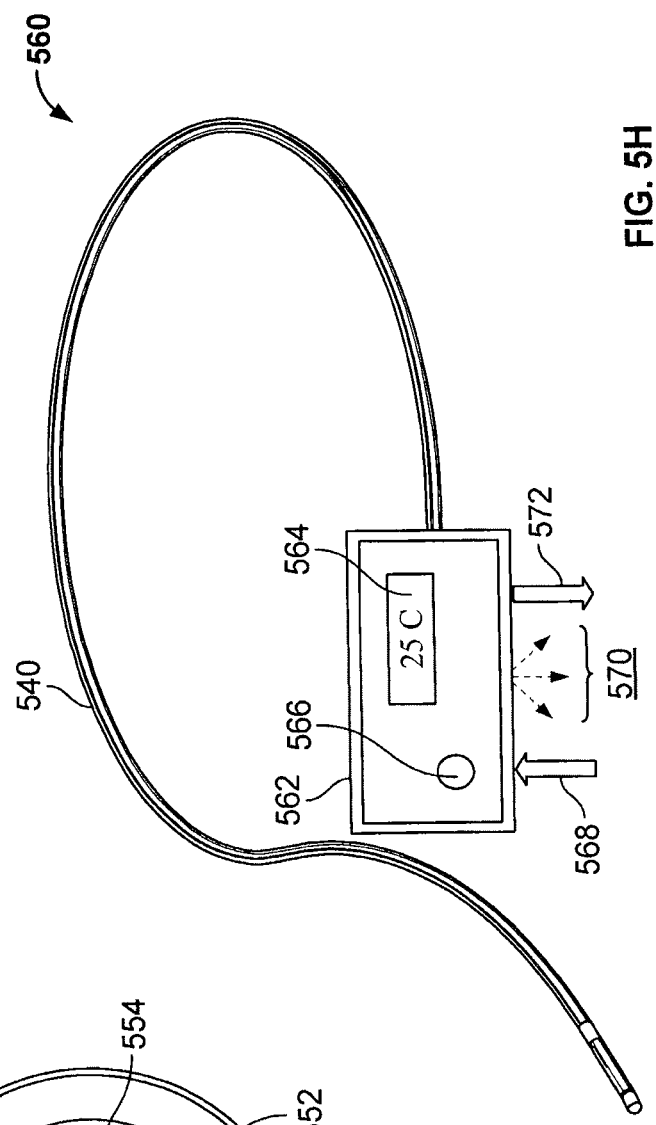
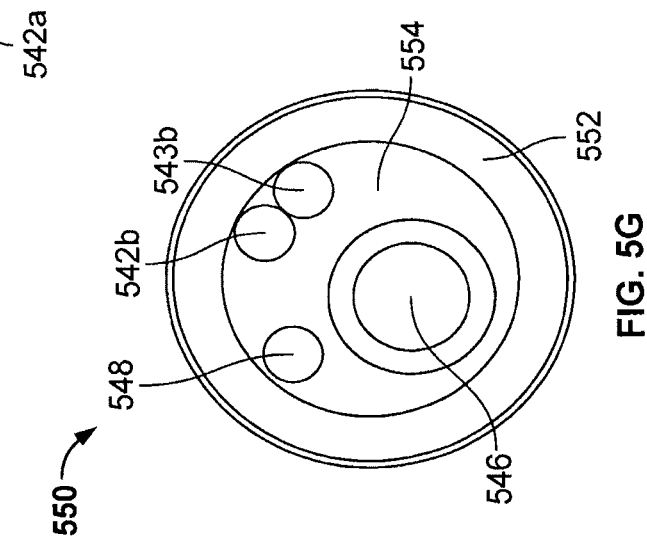

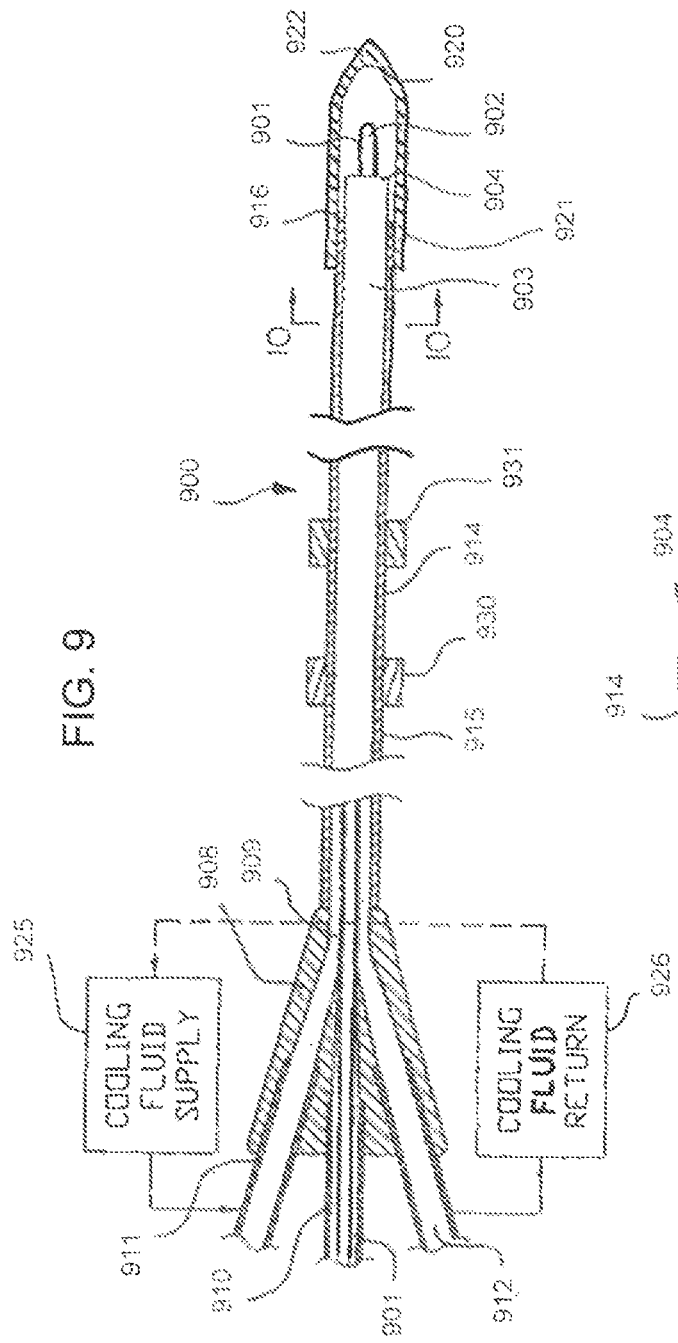
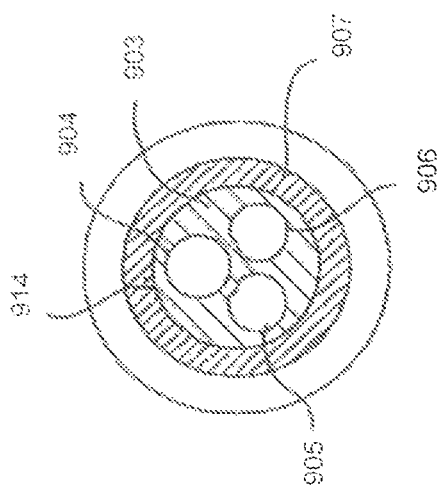
FIG. 9
FIG. 10

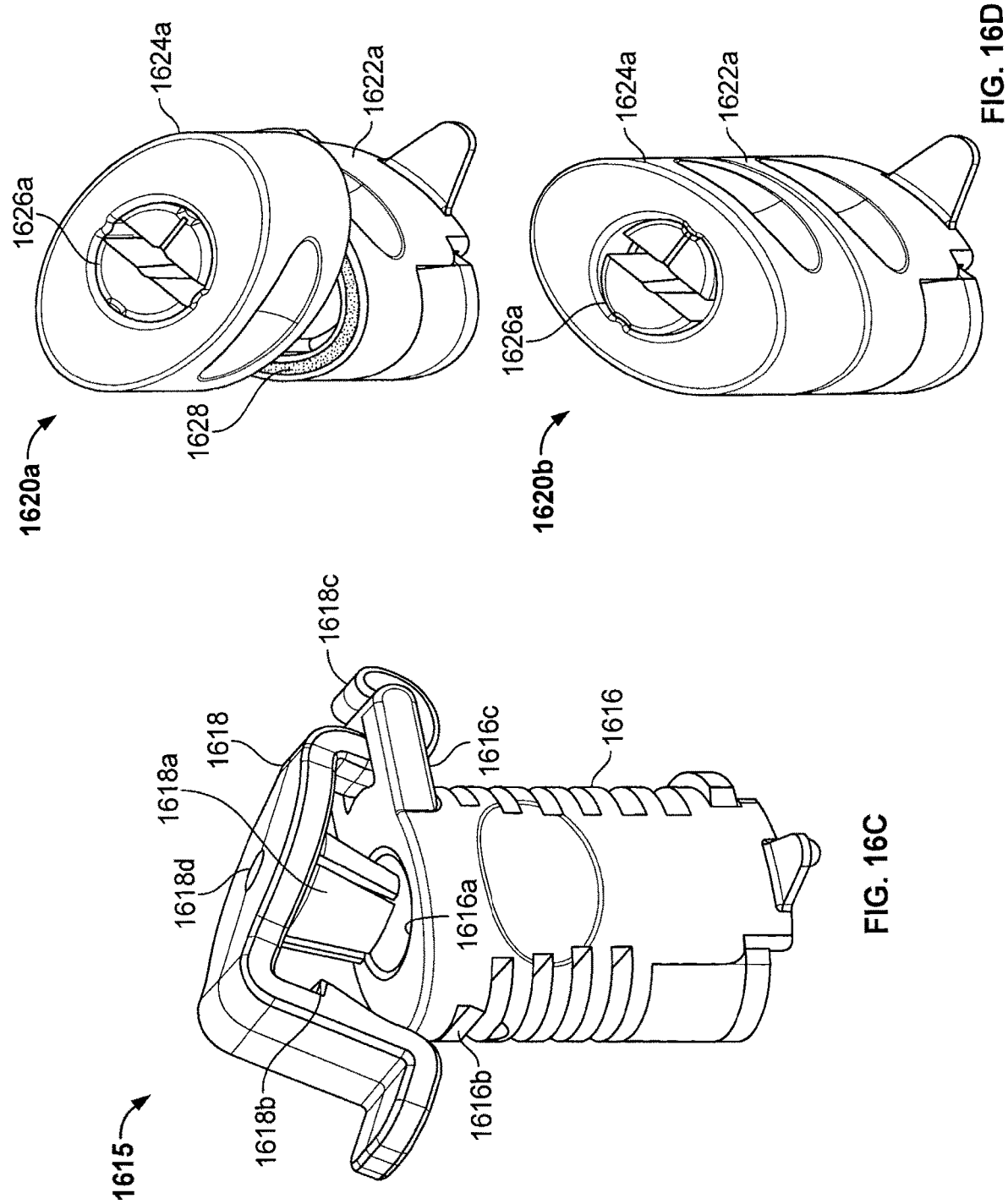

CRYOTHERAPY, THERMAL THERAPY, TEMPERATURE MODULATION THERAPY, AND PROBE APPARATUS THEREFOR

CROSS REFERENCE TO RELATED APPLICATIONS

This application is a continuation of U.S. patent application Ser. No. 14/841,109, filed on Aug. 31, 2015, allowed; which claims priority to U.S. Provisional patent application Ser. No. 62/141,612, filed Apr. 1, 2015; the entireties of which are incorporated by reference herein.

BACKGROUND OF THE INVENTION

Tumors, such as brain tumors, may be treated by heat (also referred to as hyperthermia or thermal therapy). In particular, it is known that above 57.degree. C. all living tissue is almost immediately and irreparably damaged and killed through a process called coagulation necrosis or ablation. Malignant tumors, because of their high vascularization and altered DNA, are more susceptible to heat-induced damage than normal tissue. Various types of energy sources may be used, such as laser, microwave, radiofrequency, electric, and ultrasound sources. Depending upon the application and the technology, the heat source may be extracorporeal (i.e., outside the body), extrastitial (i.e., outside the tumor), or interstitial (i.e., inside the tumor). One example treatment of a tissue includes interstitial thermal therapy (ITT), which is a process designed to heat and destroy a tumor from within the tumor itself. In this type of therapy, energy may be applied directly to the tumor rather than passing through surrounding normal tissue, and energy deposition can be more likely to be extended throughout the entire tumor.

Further, tumors and other abnormal cellular masses may be treated using a cryosurgical or cryotherapy technique where extreme cold conditions are applied to damage or destroy tissue. In one example, a coolant, such as liquid nitrogen or liquid argon, may be circulated within a probe device (cryoprobe) while in contact with tumorous tissue to freeze tissue within the vicinity of the cryoprobe.

BRIEF SUMMARY OF THE INVENTION

In one aspect, the present disclosure relates to a variable length probe apparatus having a variable length probe structure including a probe and an adjustable depth stop to facilitate access to both shallow and deep targeted tissue areas. The variable length probe apparatus may be configured to accommodate lesions located at varying depths by repositioning over the adjustable depth stop. The probe portion, in some embodiments, is connected to an umbilical sheath for carrying inputs and outputs (e.g., energy, control signals, cooling gas or fluid, and/or heating gas or fluid) between the probe and a control unit. A transitional part configured for ease of grasping and manipulation of the probe may be disposed at the junction of the probe and the flexible umbilical sheath. The adjustable depth stop may be configured to connect to or otherwise rest upon a probe follower for remote rotational and/or linear positioning of the variable length probe apparatus.

In one aspect, the present disclosure relates to temperature modulation probes configured for modulated application of thermal therapy and cryotherapy using at least one thermal therapy-generating element as well as at least one cryotherapy-generating element disposed within the temperature modulation probe. In use, the temperature modulation probe supplies a modulated temperature output pattern to a target tissue, varying between at least one warmer temperature applied at least in part by the thermal therapy-generating element and at least one colder temperature applied at least in part by the cryotherapy-generating element.

In one aspect, the present disclosure relates to methods for supplying temperature modulation therapy to a tissue using a temperature modulation probe. The method may include identifying a modulation pattern, monitoring temperature(s) of the target tissue, and, where needed, adjusting the modulation pattern in real time to effect a desired temperature or temperature profile goal. The method may include continuously supplying therapy to a tissue while automatically adjusting a probe position in a rotational and/or linear direction.

In one aspect, the present disclosure relates to focal laser probes including a shortened lens region for focusing the laser and reducing manufacturing costs. A focal laser probe may be designed, for example, by exposing only a forward directed tip of the laser fiber and shortening the capsule portion of the respective probe to avoid stray energy transmission, for example due to internal reflections. Focal laser probes may be used for providing focal thermal therapy through at least one of ablation, coagulation, cavitation, vaporization, necrosis, carbonization, and reversible thermal cellular damage. The focal emission supplied by focal laser probes provides precision to protect surrounding tissues during thermal therapy, while resulting in minimal edema which encourages immediate therapeutic benefit.

In one aspect, the present disclosure relates to cryogenic therapy probes configured for interstitial cryoablation of a tissue. Cryogenic therapy probes can include internal thermal monitoring and real time adjustment of pressure, flow, and/or temperature delivery parameters for adjusting an emission temperature and/or emission pattern. Cryogenic therapy probes may employ Joule-Thomson cooling. An aperture of a fluid delivery tube may be designed for different directional deployment depending upon a desired use for a particular cryogenic therapy probe, such as a side-firing cryogenic therapy probe or a focal cryogenic therapy probe. In some embodiments, an adjustable aperture may be mechanically or electrically adjusted to control flow rate, pressure, and/or deployment patterns (e.g., ranging from focal to diffuse).

In one aspect, the present disclosure relates to probes, probe sheaths, and probe sleeves incorporating one or more recording elements. A recording element may include an electrocardiography (ECG) wire and/or an electroencephalography (EEG) wire. A recording element may be used for lesion localization and assessment at the time of cryotherapy, thermal therapy, or temperature modulation therapy. A recording element may be used to provide positioning and monitoring during functional neurosurgery. In the example of epileptic symptoms, the recording element may be used to confirm positioning of therapeutic energy for treatment of seizure activity. A recording element may be used to confirm disruption of the blood-brain barrier. A recording element may be used for monitoring biorhythms while performing an operation or other therapy. A recording element may be used to apply local tissue stimulation responsive to detection of an abnormal event to regulate cellular behaviors during treatment. A recording element may be used to effect deep brain stimulation during a neurosurgical operation.

In one aspect, the present disclosure relates to recording instruments incorporating one or more recording elements for monitoring internal electrical signals and identifying abnormalities. The recording instruments, for example, may be designed for in vivo deployment for hours or days while monitoring and analyzing signals such as deep brain signals. For signal analysis, leads disposed between recording element contact surfaces and along a shaft of the recording instrument may deliver recorded signals from the contact surfaces to a controller external to the patient for analysis. In one example, a recording instrument includes a cooling tube for delivery of cooling gas or fluid to a cooling zone region of the recording instrument. Further to this example, a temperature sensor such as a thermocouple may be disposed within or adjacent to the cooling zone region of the recording instrument for monitoring a temperature of the recording instrument. The temperature sensor, in a particular example, may provide temperature data to a thermal readout external to the patient. In an additional particular example, the temperature sensor may provide temperature data to a controller external to the patient for controlling cooling gas or fluid delivery to the cooling zone region.

In one aspect, the present disclosure relates to reduced profile probe designs. Reducing the profile of a probe is desirable for achieving minimally invasive surgery, performing surgical operations upon small bodies such as infants, juveniles and animals, and reaching otherwise difficult-to-reach in situ locations without negatively impacting surrounding tissues. A reduced profile probe, for example, can allow entry into small and narrow spaces in the brain while reducing patient injury. A low profile probe may include multiple internal lumens. Low profile probes may be configured with selected materials, lumen structures, and layer structures to provide desired and/or selected mechanical properties including straightness, rigidity, torque strength, column strength, tensile strength, kink resistance, and thermal properties such as thermal stability and thermal stress capacity. Low profile probe dimensions may vary, in some examples, based upon the style of the low profile probe (e.g., thermal therapy, cryotherapy, temperature modulation therapy), the anticipated probe deployment (e.g., intracranial, spinal, cardiac, etc.), the required thermal tolerances of the low profile probe, and/or the required structural tolerances of the probe (e.g., flexible vs. rigid). The following are examples of low profile probe dimensions: the inner shaft of a low profile probe may have an outer diameter of 2.0 mm, within a tolerance of 0.03 mm and an inner diameter of 1.5 mm, within a tolerance of 0.03 mm; the outer shaft may have an outer diameter of 2.25 mm, within a tolerance of 0.03 mm and an inner diameter of 2.07 mm, within a tolerance of 0.03 mm; the shaft may have an outer diameter of approximately 2.1 mm, approximately 2.2 mm, or less than approximately 3.2 mm. In additional examples, the shaft of various low profile probe designs may have an outer diameter of approximately 1.0 mm or approximately 1.2 mm.

With any of the apparatus described within, it may be understood that materials used for manufacture may be selected, in some embodiments, for compatibility with thermal imaging systems, such as Magnetic Resonance Imaging. Thermal imaging-compatible materials, in some examples, may include polymeric material such as nylon, ethylenetetrafluoroethylene, polyamines, polyimides, and other plastics, quartz, sapphire, crystal structures, and/or glass-type structures. Additionally, small amounts of thermal-imaging tolerant (non-ferromagnetic) metal materials such as titanium and titanium alloys may be included, for example in various connectors for stabilizing positioning of neurosurgical instruments relative to introduction equipment. In further embodiments, material selection may be based in part upon compatibility with various imaging or neurosurgical treatment modalities such as, in some examples, radiofrequency (RF), high-intensity focused ultrasound (HiFU), microwave, and/or cryogenic energy.

In some embodiments, the present disclosure describes a system for deploying at least one signal recording electrode proximate a tissue during interstitial therapy to the tissue, the system including: an interstitial therapy instrument including a tip region and a shaft region, where the interstitial therapy instrument includes at least one therapy generating element, where the at least one therapy generating element includes one of a) a thermal therapy-generating element for thermal therapy emission via the tip region and b) a cryotherapy-generating element for cryogenic therapy emission via the tip region; and at least one signal recording element configured for deployment proximate to the tip region, where the at least one signal recording element includes one of an electrocardiography recording element, an electroencephalography recording element, and a stereo electroencephalography recording element.

In some embodiments, the system includes a controller including processing circuitry and a memory having instructions stored thereon, where the instructions, when executed by the processing circuitry, cause the processing circuitry to, while the interstitial therapy instrument is positioned proximate a tissue, receive signal recordings from the at least one signal recording element, analyze the signal recordings to identify an abnormal signal pattern, and responsive to identifying the abnormal signal pattern, cause at least one of i) adjustment of an emissive output of a first therapy generating element of the at least one therapy generating element, ii) adjustment of a therapeutic profile for delivering therapy to the tissue via the interstitial therapy instrument, iii) adjustment of a linear position of the interstitial probe, iv) adjustment of a rotational position of the interstitial therapy instrument, and v) output of at least one of visual information and audible information regarding the abnormal signal pattern for the attention of an operator. The instructions may cause the processing circuitry to, prior to receiving the signal recordings, cause extension of at least a first signal recording element of the at least one signal recording element along the tip region of the interstitial therapy instrument. The first signal recording element may be extended from the shaft portion of the interstitial therapy instrument. The instructions may cause the processing circuitry to, after receiving the signal recordings and prior to adjusting the emissive output of the first therapy generating element, cause retraction of the first signal recording element such that the first signal recording element will not interfere with the first therapy generating element. Identifying the abnormal signal pattern may include identifying a signal pattern associated with a lesion. The instructions may cause the processing circuitry to, before receiving the signal recordings, cause emission of the cryotherapy-generating element directed to the tissue; receive initial signal recordings from the at least one signal recording element, analyze the initial signal recordings to identify a hibernation pattern; and cause cessation of emission of the cryotherapy-generating element; where the signal recordings are captured while the tissue is warming.

In some embodiments, the system includes a flexible sleeve, where the flexible sleeve surrounds the interstitial therapy instrument and includes the at least one signal recording element. The system may include a guide sheath including a number of lumens, where the interstitial probe is disposed within a first lumen of the number of lumens and a first signal recording element of the at least one signal recording element is disposed within a second lumen of the number of lumens.

In some embodiments, the at least one signal recording element includes at least three signal recording elements. The at least three signal recording elements may be provided as rings surrounding a circumference of the interstitial therapy instrument. The rings may be formed along the shaft region of the interstitial therapy instrument.

In some embodiments, the present disclosure describes a focal laser induced interstitial thermal therapy probe for treatment of a tissue, including: a transparent lens capsule; a laser fiber including a sheath portion and an exposed tip, where the exposed tip is disposed within the transparent lens capsule; a shaft portion fixed to the transparent lens capsule, where the laser fiber extends along the shaft portion; and a cooling supply tube disposed within the shaft portion for delivering at least one of a cooling fluid and a cooling gas to the transparent lens capsule; where the exposed tip is configured to direct focal energy through a tip portion of the transparent lens capsule in a forward direction, and the length of the transparent lens capsule is configured to minimize energy transmissions outside of the forward direction. The tip portion of the transparent lens capsule may be substantially flat in shape. The exposed tip may be substantially flat in shape.

In some embodiments, the present disclosure describes a system for providing interstitial cryotherapy to a tissue, the system including: an interstitial cryogenic probe, including a shaft region and a tip region, where a distal end of the tip region is affixed to a proximal end of the shaft region. The system may include an injection tube disposed within the shaft region for delivering a refrigerant to the tip region, and a temperature sensor disposed within the shaft region. The system may include a controller including processing circuitry and a non-transitory computer readable medium having instructions stored thereon for controlling emission of the interstitial cryogenic probe, where the instructions, when executed by the processing circuitry, cause the processing circuitry to, during cryotherapy of the tissue, receive temperature signals from the temperature sensor, and responsive to the temperature signals, adjust at least one of a pressure, a flow rate, and a temperature of refrigerant delivered to the injection tube. The temperature sensor may be a thermocouple. The injection tube and tip region may be configured for Joule-Thomson cooling. The interstitial cryogenic probe may include a vacuum return lumen to direct evaporated refrigerant towards the shaft region of the interstitial cryogenic probe. An orifice of the injection tube may be configured for side-firing emission of refrigerant. The interstitial cryogenic probe may include a porous plug at an orifice of the injection tube. Adjusting the flow rate may include modulating the flow of refrigerant in an on-off pattern.

In some embodiments, the present disclosure describes an interstitial probe for performing temperature modulation therapy to a tissue, the interstitial probe including: a shaft region; a tip region; at least one thermal therapy-generating element for thermal therapy emission via the tip region; at least one cryotherapy-generating element for cryogenic therapy emission via the tip region; processing circuitry disposed within the shaft region; and a memory disposed within the shaft region, the memory having instructions stored thereon for causing emission of a number of thermal modulation patterns, where each thermal modulation pattern of the number of thermal modulation patterns includes at least one higher thermal output corresponding to activation of a first thermal therapy element of the at least the thermal therapy-generating element for a first time interval, and at least one lower thermal output corresponding to activation of a first cryogenic therapy element of the at least one cryogenic therapy element for a second time interval different than the first time interval. The instructions, when executed by the processing circuitry, may cause the processing circuitry to receive selection of a first thermal modulation pattern of the number of thermal modulation patterns, and activate temperature modulation therapy utilizing the modulation pattern. The memory may include a programmable memory element, the interstitial probe further including at least one communication connection for programming the programmable memory element with one or more additional thermal modulation patterns.

In some embodiments, the present disclosure describes a low profile interstitial probe for effecting at least one of thermal therapy and cryotherapy to a tissue, the low profile interstitial probe including a shaft, including at least one outer layer and at least one inner layer, where an outermost layer of the at least one outer layer has a first set of mechanical properties including at least two of the following: straightness, rigidity, torque strength, column strength, tensile strength, kink resistance, thermal stability, and thermal stress capacity, and an approximate outer diameter of less than 3.2 mm, and an innermost layer of the at least one inner layer has a second set of mechanical properties including at least two of the following: straightness, rigidity, torque strength, column strength, tensile strength, kink resistance, thermal stability, and thermal stress capacity, and an approximate maximum inner diameter of at least 1.5 mm; The low profile interstitial probe may include a transparent lens capsule through which energy is delivered to the tissue during treatment, where a distal end of the transparent lens capsule is connected to a proximal end of the shaft region; and an energy emission element may be disposed at least in part within the transparent lens.

The low profile interstitial probe may include a number of lumens formed within the innermost layer, where the maximum inner diameter corresponds to a widest diameter measurable between two or more adjacent lumens. A first lumen of the number of lumens may be configured to carry an energy emission medium to the energy emission element; and a second lumen of the number of lumens may be configured to deliver cooling gas to the transparent lens capsule.

The outermost layer may be configured to act a protective barrier in case of breakage of a layer of the shaft directly abutting an inner surface of the outermost layer. The outermost layer may be a thin-walled polyether ether keretone (PEEK) plastic; and the outermost layer may partially overlap the transparent lens capsule. The outermost layer may be linearly aligned with the remaining layers of the at least one outer layer and the at least one inner layer to provide a counterbore region, where a distal portion of the transparent lens capsule is permanently affixed to the counterbore region. The transparent lens capsule may be composed of machined sapphire.

The foregoing general description of the illustrative implementations and the following detailed description thereof are merely exemplary aspects of the teachings of this disclosure, and are not restrictive.

BRIEF DESCRIPTION OF THE DRAWINGS

A more complete appreciation of this disclosure and many of the attendant features thereof will be readily obtained as the same becomes better understood by reference to the following detailed description when considered in connection with the accompanying drawings, wherein:

FIGS. 1A and 1B illustrate components of an example probe;

FIGS. 1E and 1F illustrate an example depth locking element for use with the variable length probe of FIGS. 1C and 1D;

FIG. 1G illustrates an example cut-away view of a flexible umbilical portion of the variable length probe of FIGS. 1C and 1D;

FIG. 1H illustrates an example transition element positioned between the variable length probe and the flexible umbilical of the variable length probe apparatus of FIGS. 1C and 1D;

FIGS. 2E-2G illustrate an example probe follower with a low profile design;

FIGS. 5F through 5H illustrate example options for designing a recording instrument;

FIG. 9 is a longitudinal cross-sectional view through an alternative form of a probe that provides a flow of cooling fluid to the end of the probe for cooling the surrounding tissue;

FIG. 10 is a cross-sectional view along the lines 10-10 of FIG. 9;

FIGS. 16A through 16H illustrate alternative depth locking element configurations for use with the variable length probe of FIGS. 1C and 1D.

DETAILED DESCRIPTION OF THE INVENTION

Figure 1C:
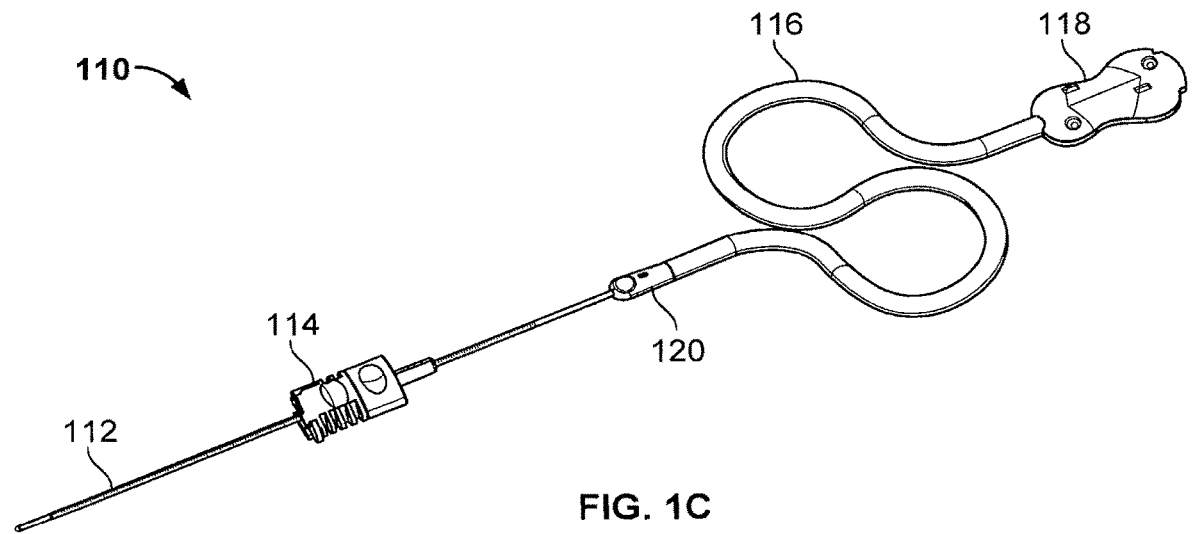
FIGS. 1C and 1D illustrate components of an example variable length probe apparatus.

In the drawings, like reference numerals designate identical or corresponding parts throughout the several views. Further, as used herein, the words "a," "an" and the like generally carry a meaning of "one or more," unless stated otherwise.

Further, in individual drawings figures, the components/features shown are drawn to scale to exemplify a particular implementation. For some drawings, components/features are drawn to scale across separate drawing figures. However, for other drawings, components/features are shown magnified with respect to one or more other drawings.

Measurements and ranges described herein relate to exemplary implementations and can identify a value or values within a range of 1%, 2%, 3%, 4%, 5%, or, preferably, 1.5% of the specified value(s) in some implementations.

FIGS. 1A and 1B illustrate exemplary aspects of a probe. Types of probes that can be utilized with the components and procedures discussed herein include laser, radiofrequency (RF), high-intensity focused ultrasound (HiFu), microwave, cryogenic, chemical release, which may include photodynamic therapy (PDT), and drug releasing probes.

Further probes can include temperature modulation probes including at least one thermal therapy-generating element (e.g., RF, HiFu, microwave, laser, electrical heat, heating fluid or supercritical fluid, heating gas, etc.) and at least one cryotherapy-generating element (e.g., cooling gas, cooling fluid, etc.). Each of the at least one thermal therapy-generating element and the at least one cryotherapy-generating element may be configured to emit respective thermal or cryo energy in a side-firing, focal, or diffuse manner. In a particular example, a temperature modulation probe includes a circumferentially emitting thermal therapy-generating element and a circumferentially emitting cryotherapy-generating element.

The temperature modulation probes of the present disclosure may be designed for insertion into a body cavity, insertion into vascular system, or interstitial deployment.

Treatments in accordance with the descriptions provided in this disclosure include treatments that ablate a tissue to destroy, inhibit and/or stop one or more or all biological functions of the tissue. Ablation agents include, but are not limited to, laser, RF, HiFu, microwave, cryogenic, PDT and drug or chemical release. A corresponding probe and/or another instrument, such as a needle, fiber or intravenous line can be utilized to effect treatment by one or more of these ablation agents. Treatments in accordance with the descriptions provided in this disclosure include treatments that create temporary or permanent physical-biological effects to tissue including freezing freeze-thawing, hyperthermia, coagulation, and/or vaporization of tissues. The temporary or permanent physical-biological effects can include alterations in biological function of cells, tissues, and/or body fluids. In a particular example, the treatment may cause the cells, tissues, and/or body fluids to be more receptive or sensitive to additional therapies or manipulations such as, in some examples, radiation therapy or chemotherapy. In a further example, the treatment may cause hemostasis, reduction or dissolution of thrombi or emboli, alteration of functional membranes including the blood-brain barrier, and/or renal filtration. The physical-biological effects may be caused directly by temperature change to the cells, tissues, and/or body fluids or indirectly (e.g., downstream) from the temperature change, such as alterations in heat shock proteins or immune reaction or status.

Figure 7A:
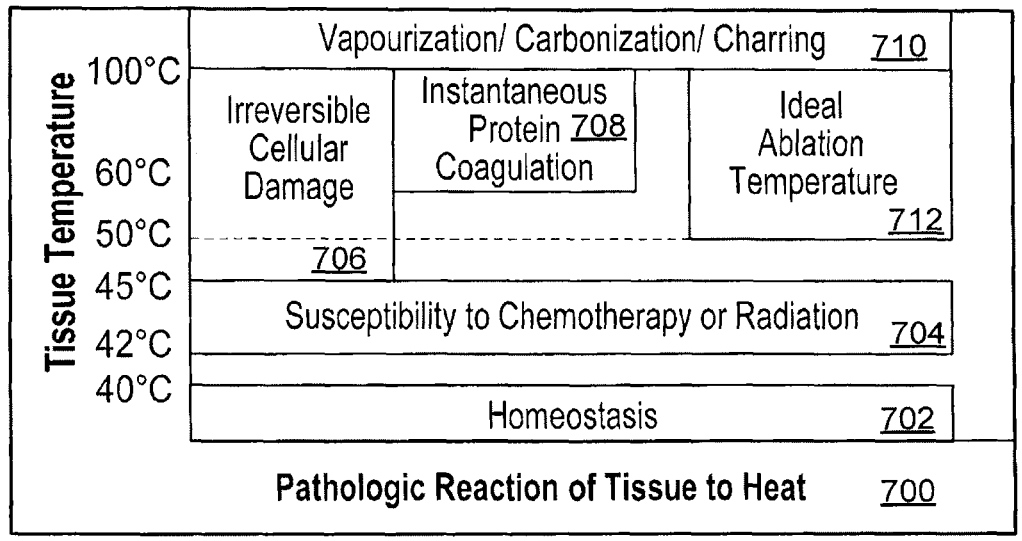
FIG. 7A is a graph of example temperature ranges for causing various effects on tissue via thermal therapy.

Turning to FIG. 7A, a graph 700 illustrates example temperature ranges for causing various effects on tissue via thermal therapy, such as homeostasis 702 (up to 40.degree. C.), susceptibility to chemotherapy or radiation 704 (about 42.degree. C. to 45.degree. C.), irreversible cellular damage 706 (about 45.degree. C. to 100.degree. C.), instantaneous protein coagulation 708 (about 55.degree. C. to 100.degree. C.), and vaporization/carbonization/charring 710 (above 100.degree. C.). The ranges represent estimated bands of opportunity for causing the various effects 702-710 upon tissue, while more precise temperature ranges depend upon a number of factors such as tissue type, tissue location, baseline temperature. Further, the graph 700 illustrates an "ideal" ablation temperature range 712 of approximately 50.degree. C. to 100.degree. C. The ideal ablation temperature range 712, starting about 5 degrees hotter than irreversible cellular damage range 706, may be representative of a range in which there is desired degree of confidence that therapy will cause total cellular death without unwanted tissue damage (vaporization/carbonization/charring 710).

Figure 7B:
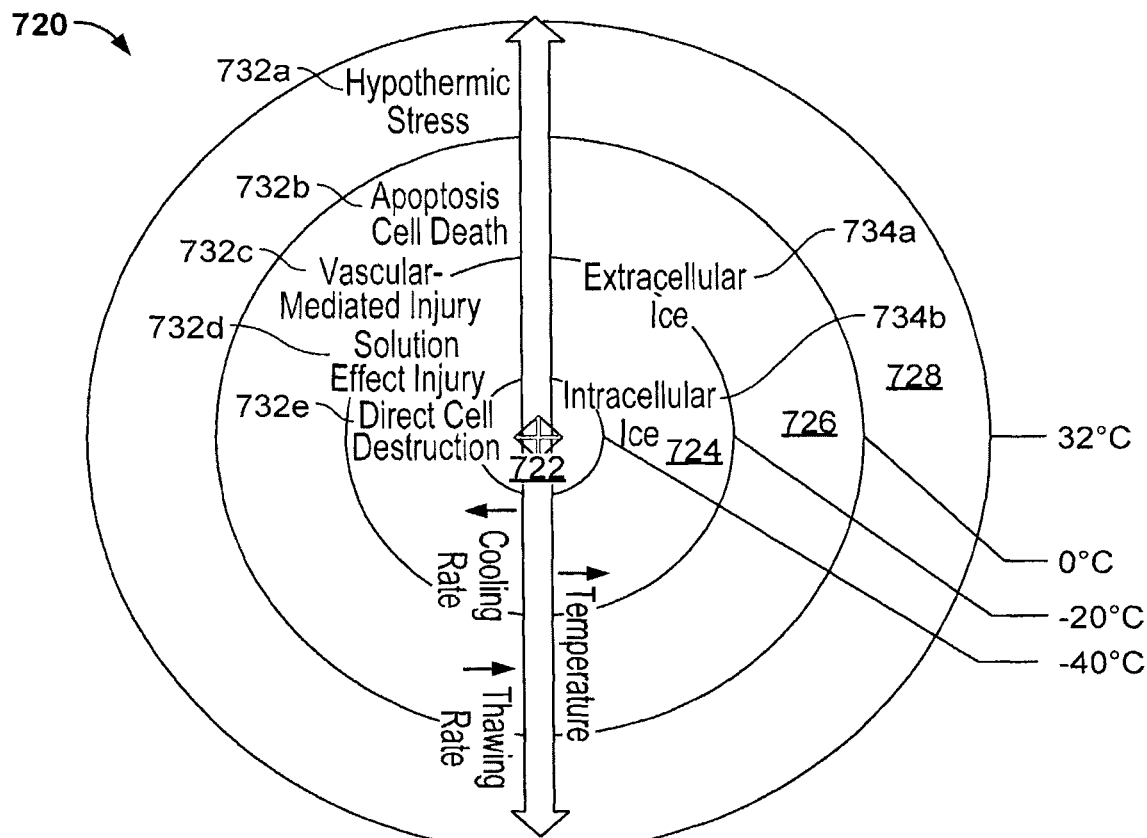
FIG. 7B is a graph of example temperature ranges for causing various effects on tissue via cryotherapy.

Turning to FIG. 7B, a graph 720 illustrates example temperature ranges for causing various effects on tissue via cryotherapy. For example, within a first thermal band 722 (up to −40.degree. C.) as well as a second thermal band 724 (−40.degree. C. to −20.degree. C.), direct cell destruction 732e may occur during cooling 730a, while intercellular ice 734b may develop. Also within the second thermal band 724, solution effect injury 732d may occur and extracellular ice 734a may develop. The solution effect injury 732d and extracellular ice 734a carries over into a third thermal band 726 (between −20.degree. C. and 0.degree. C.). Also shared between the second thermal band 724 and the third thermal band 726, vascular-mediated injury 732c may occur. Within the third thermal band 726, apoptosis cell death 732b may occur. Finally, within a fourth thermal band (0.degree. C. to 32.degree. C.), hypothermic stress may result.

An energy output pattern of a temperature modulation probe includes a modulated output pattern, varying between at least one warmer temperature applied at least in part by one or more thermal therapy-generating elements and at least one cooler temperature applied at least in part by one or more cryotherapy-generating elements. In certain embodiments, a particular energy output pattern may be developed based upon the type of thermal therapy-generating elements and cryotherapy-generating element included within the probe, an emission style of the probe tip (e.g., side-firing, focal tip, diffuse tip, etc.), and/or the depth of the region of interest or the targeted tissue area (e.g., based in part on the shape of a tumor region, etc.).

An energy output pattern of a probe, such as a laser probe or HIFU probe, in certain embodiments, includes a pulsed output pattern. For example, a higher power density may be achieved without causing tissue scorching by pulsing a high power laser treatment for x seconds with y seconds break between (e.g., allowing for tissue in the immediate vicinity to cool down by only activating the cryotherapy-generating element). In a particular example, the energy output pattern of a probe may include a ten Watt output of the thermal therapy-generating element for two seconds while maintaining activation of the cryotherapy-generating element, followed by a one second period of inactivity of the thermal therapy-generating element while maintaining activation of the cryotherapy-generating element. Conversely, the thermal therapy-producing element may remain activated, in some pulsed output patterns, while modulating activation of the cryotherapy-generating element.

An energy output pattern of a probe, in certain embodiments, includes a refined temperature modulated pattern, where both the thermal therapy-generating element(s) and the cryotherapy-generating element(s) is/are constantly activated, while power levels, emission levels, flow rates, and/or energy levels are varied between the elements to cycle between cooler and warmer output.

In certain embodiments, a particular energy output pattern may be developed based upon the type of probe (e.g., laser, HIFU, etc.), an emission style of the probe tip (e.g., side-firing, diffuse tip, etc.), and/or the depth of the ROI or the targeted tissue area (e.g., based in part on the shape of a tumor region, etc.).

In certain embodiments, a treatment pattern includes effecting treatment while concurrently or simultaneously moving the probe (e.g., linearly and/or rotationally). For example, a thermal therapy, cryotherapy, or temperature modulation probe may be automatically rotated (e.g., using a commander and follower as described in relation to FIG. 2A) while an emission pattern and/or modulation pattern is simultaneously or concurrently adjusted to effect treatment to a desired depth based upon a particular geometry of the region of interest.

An example probe apparatus 100 is shown in FIG. 1A and FIG. 1B. A probe tip 102 indicates an insertion end of the probe apparatus 100. A probe interface/depth stop adjustment 104 provides an interface for cabling, as well as for alignment with the probe driver and/or the stereotactic miniframe. An end opposite the insertion end includes probe connectors 106 for energy delivery, cooling, etc. extending from a probe interface boot 108. FIG. 1B is an enlarged view of the probe interface 104 to probe tip 102 portion of the probe apparatus 100 shown in FIG. 1A.

In an example embodiment of probe apparatus as discussed in relation to FIG. 1A and FIG. 1B, turning to FIG. 1C, a variable length probe apparatus 110 has a variable length probe structure including a probe 112 and an adjustable depth stop 114 to facilitate access to both shallow and deep targeted tissue areas; that is, the same probe 112 can accommodate lesions located at varying depths by repositioning over the adjustable depth stop 114. Beyond the probe 112 is a flexible umbilical sheath 116 for carrying inputs and outputs (e.g., energy, control signals, cooling gas or fluid, and/or heating gas or fluid) between the probe 112 and a control unit (not illustrated). At the junction of the probe 112 and the flexible umbilical sheath 116 is a transitional part 120 configured for ease of grasping and manipulation of the probe 112 when positioning the probe 112 in a target tissue region. The general design of the variable length probe apparatus 110 shown in FIG. 1C contains elements shown in FIG. 1A and FIG. 1B, such as a probe interface boot 118 which would lead to the probe connectors 106 illustrated in FIG. 1A. Further, the probe 112 may be designed to achieve the desired and/or selected thermal and/or mechanical properties discussed throughout in relation to the various probe designs, such as the probe apparatus 110 of FIG. 1C, the probe apparatus 224 of FIG. 2B, the probe 300 of FIG. 3A, the probe 320 of FIG. 3B, the probe 400 of FIG. 4, the probe 500 of FIG. 5, the probe 510 of FIGS. 5B and 5C, the probe 530 of FIGS. 5D and 5E, the probe 900 of FIG. 9, the probe of FIG. 11, the probe 1300 of FIG. 13A, the probe 1400 of FIG. 14A, and/or the probe 1500 of FIG. 15A. In some embodiments, the variable length probe apparatus 110 is capable of remote operation, for example using a probe driver apparatus such as the probe driver discussed in relation to FIG. 2A.

Figure 1D:
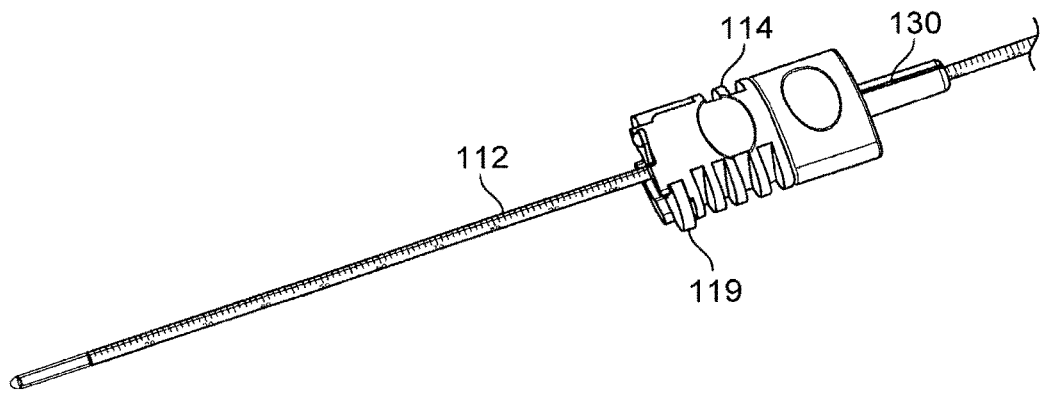

As illustrated in FIG. 1D, an enlarged view of the probe 112 and the adjustable depth stop 114 demonstrates measured gradations (e.g., centimeters, millimeters, inches, etc.) printed along the shaft of the probe 112. An operator may align the measured gradations with the adjustable depth stop 114, for example, by sliding a position of the adjustable depth stop 114 along the shaft of the probe 112 until the desired depth measurement aligns with the probe end of the adjustable depth stop 114. In another example, the operator may align the desired depth measurement with the sheath end of the probe 112 (e.g., for clearer visibility). In this example, the gradations may be applied to the shaft of the probe 112 to compensate for a length of the adjustable depth stop 114. In a further embodiment (not illustrated), the adjustable depth stop 114 may include a window (e.g., cut-out portion, clear portion, or clear, magnified portion) for aligning a desired depth measurement while slidably positioning the adjustable depth stop 114. In this example, the gradations may be applied to the shaft of the probe 112 to compensate for the portion of the length of the adjustable depth stop 114 from the probe end to the depth selection window.

Instead or in addition to the printed gradations, in other embodiments, the shaft of the probe 112 may include a series of mating points for mating with the adjustable depth stop 114. For example, the shaft of the probe 112 may include a series of bumps (e.g., every 5 millimeters, 10 millimeters, etc.) and the adjustable depth stop 114 may include one or more mating depressions for engaging with at least one of the series of bumps. The mating points, for example, may be used to more precisely align the adjustable depth stop 114 with a particular depth setting.

Using the adjustable depth stop 114 with the guidance of the printed gradations upon the shaft of the probe 112, an operator may modify the probe length in situ. For example, during a patient operation, after applying a procedure at a first selected depth, an operator may vary the length or depth relatively rapidly to a second selected depth. To allow for varying the probe length of the probe 112 in-situ while controlling the internal deployment of the probe tip, the shaft of the probe 112 may be configured with a selected kink resistance value, in addition to column strength and/or torque strength and/or tensile strength and/or thermal stability.

In some embodiments, the probe apparatus 110 is compatible with a low profile trajectory guide (e.g., as described in U.S. patent application Ser. No. 14/661,194 entitled "Image-Guided Therapy of a Tissue" and filed Mar. 18, 2015 and U.S. patent application Ser. No. 14/661,212, entitled "Image-Guided Therapy of a Tissue" and filed Mar. 18, 2015, the contents of each of which is incorporated herein by reference in its entirety) and a minibolt (as described in U.S. Provisional Patent Application No. 62/132,970 entitled "Apparatus and Methods for Neurological Intervention" and filed Mar. 13, 2015, the contents of which is incorporated herein by reference in its entirety). The probe-side end of the adjustable depth stop 114, in some examples, may be designed to fit over and/or mate with a minibolt mounted to the skull of a patient or a probe driver (as described in U.S. patent application Ser. No. 14/659,488 filed Mar. 16, 2015, U.S. patent application Ser. No. 14/661,194 filed Mar. 18, 2015, and U.S. patent application Ser. No. 14/661,212 filed Mar. 18, 2015, each being entitled "Image-Guided Therapy of a Tissue," the contents of each of which are incorporated herein by reference in their entireties). For example, the adjustable depth stop 114, as illustrated in the enlarged view of FIG. 1D, can include a latch 119 for releasably attaching the adjustable depth stop 114 to the minibolt or probe driver. In another example illustrated in FIG. 16H, an adjustable depth stop may include a thumb screw 1660 for releasably attaching the adjustable depth stop to the minibolt or probe driver. In some embodiments, the adjustable depth stop 114 has a compact width, to provide more clearance within a magnetic resonance (MR) bore to allow easy operation.

Turning to FIGS. 1E and 1F, enlarged views of the adjustable depth stop 114 illustrate both an unlocked position view 122a of FIG. 1E and a locked position view 122b of FIG. 1F. As illustrated in FIG. 1E, in the unlocked position, a probe-end portion 114b of the adjustable depth stop 114 is rotated about 90 degrees offset from a sheath-end portion 114a. When in the unlocked position 122a of FIG. 1E, for example, the adjustable depth stop 114 may be slid along the shaft of the probe 112. If, instead, the adjustable depth stop 114 is mated with another piece of equipment during in situ positioning of the probe 112, the shaft of the probe 112 may be slid within the adjustable depth stop 114 for in-situ repositioning. In another example, while in the unlocked position 122a of FIG. 1E, the adjustable depth stop 114 may be removed from the probe 112. In this manner, the adjustable depth stop 114 may be used with various probes.

Figure 16B:
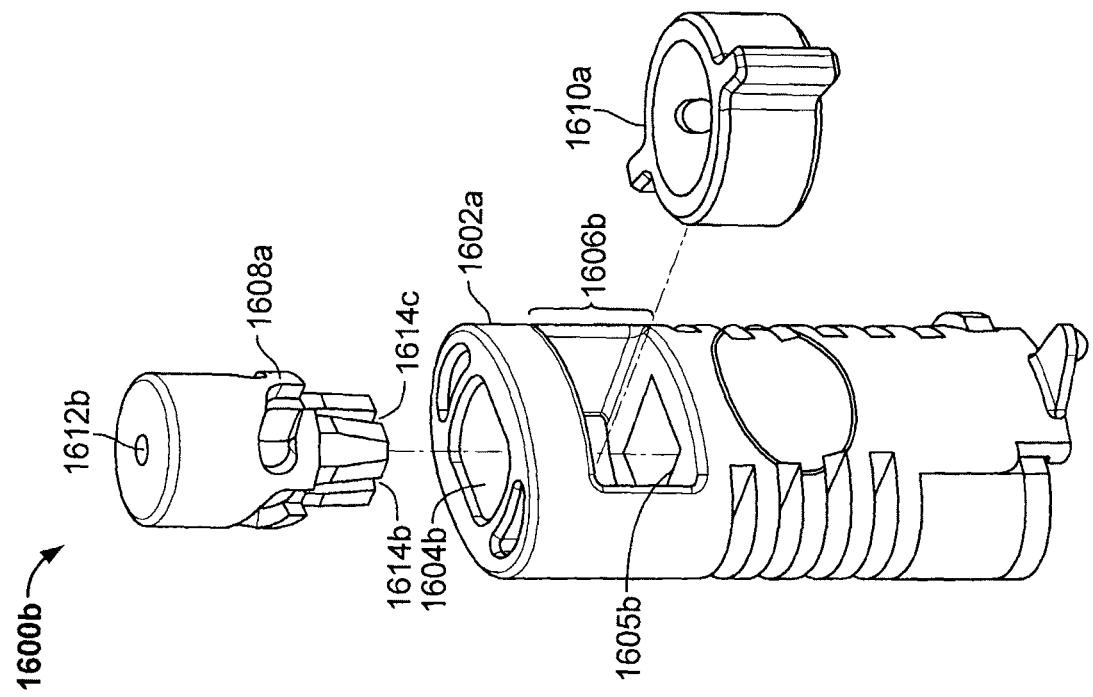
Figure 16A:
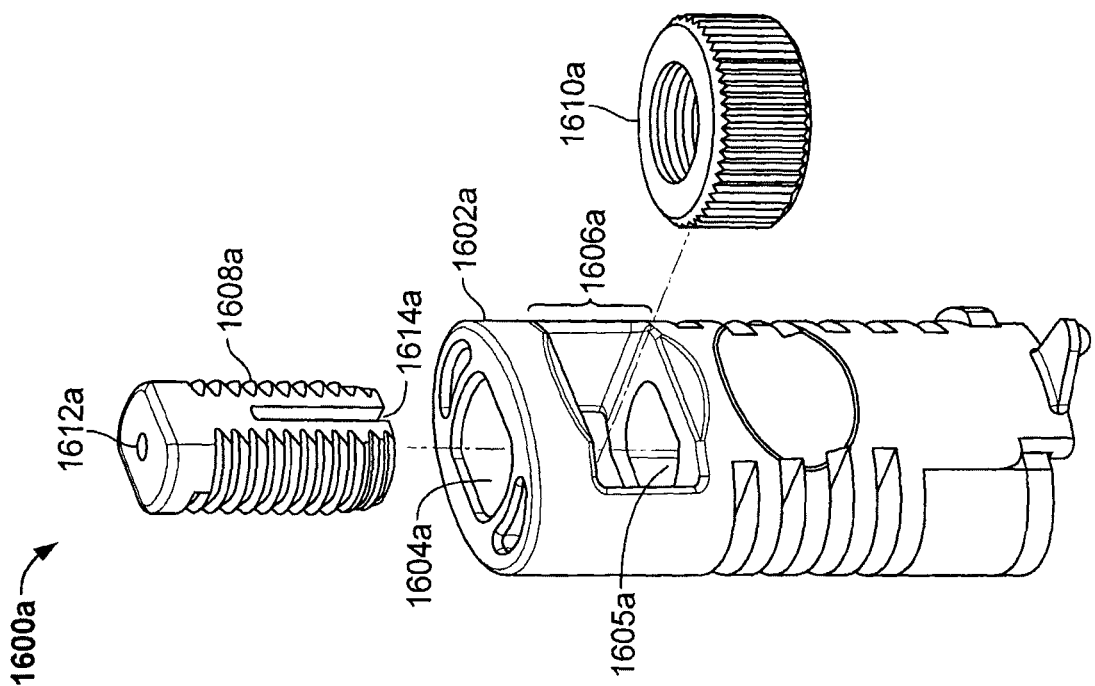

FIGS. 16A through 16H illustrate additional depth locking element configurations for use with the variable length probe of FIGS. 1C and 1D. Turning to FIGS. 16A and 16B, a body section 1602a, 1602b of a twist compression jaw style depth locking element 1600a, 1600b includes a vertical opening 1604a, 1604b aligned above a tapered hole or depression 1605a, 1605b as well as a horizontal slot 1606a, 1606b. A nut section 1620a, 1620b fits within the slot 1606a, 1606b, and a jaw section 1608a, 1608b slides through the vertical opening 1604a, 1604b to enter a center opening of the nut section 1620a, 1620b. In use, a probe, inserted through a lengthwise opening 1612a, 1612b of the jaw section 1608a, 1608b while the jaw section 1608, 1608b is nested within the center opening of the nut section 1620a, 1620b via the vertical opening 1604a, 1604b. The jaw section 1608a, 1608b and the nut section 1610a, 1610b include mated features (e.g., threads as illustrated in relation to nut section 1610a of FIG. 16A, slots and grooves as illustrated in relation to nut section 1610b of FIG. 16B) such that, when the nut 1620a, 1620b is turned, the jaw 1608a, 1608b is drawn downwards into the tapered hole or depression 1605a, 1605b of the body section 1602a, 1602b of the jaw style depth locking element 1600a, 1600b. This causes gap portions 1614a-1614c of the jaw 1608a, 1608b to close, narrowing the lengthwise opening 1612a, 1612b of the jaw portion 1608a, 1608b closest to the tapered hole or depression 1605a, 1605b and clamping onto the probe, applying locking friction against the probe.

Turning to FIG. 16C, a hinged compression jaw style depth locking element 1615 includes a body section 1616 and a latch section 1618 which connects at a hinge portion 1618c to a hinge mount 1616c of the body section 1616. In use, a probe is positioned through a probe opening 1618d of the latch section 1618, and the latch section 1618 is locked to the body section 1616 by pressing a protrusion 1618b of the latch section 1618 into a mating depression 1616b of the body section 1616. In doing so, a jaw 1618a of the latch section 1618 is pressed into a depression 1616a of the body section 1616, causing the gaps of the jaw 1618a to close, thus clamping onto and applying locking friction against the probe.

FIG. 16D illustrates a series of positions of a nonconcentric knob style depth locking element 1620 having a body section 1622 with a jaw 1626. The jaw 1626a has an elliptical shape matching an elliptical opening of a knob section 1624a such that, while in an open position 1602a, the knob 1624a fits over the jaw 1626a. In use, a probe can be positioned within the jaw 1626a along a length of the body section 1622a while the knob section 1624a is positioned over the jaw 1626a in the open position 1620a. An operator may identify the open position 1602a due to a bright band (e.g., red) 1628 being visible. Upon positioning of the probe at the desired depth, the operator may twist the knob 1624a, thus aligning the narrow diameter of the elliptical shape of the knob 1624a with the wide diameter of the elliptical shape of the jaw 1626a. This causes the gaps in the jaw 1626a to close, thus clamping onto and applying friction against the probe.

Figure 16E:
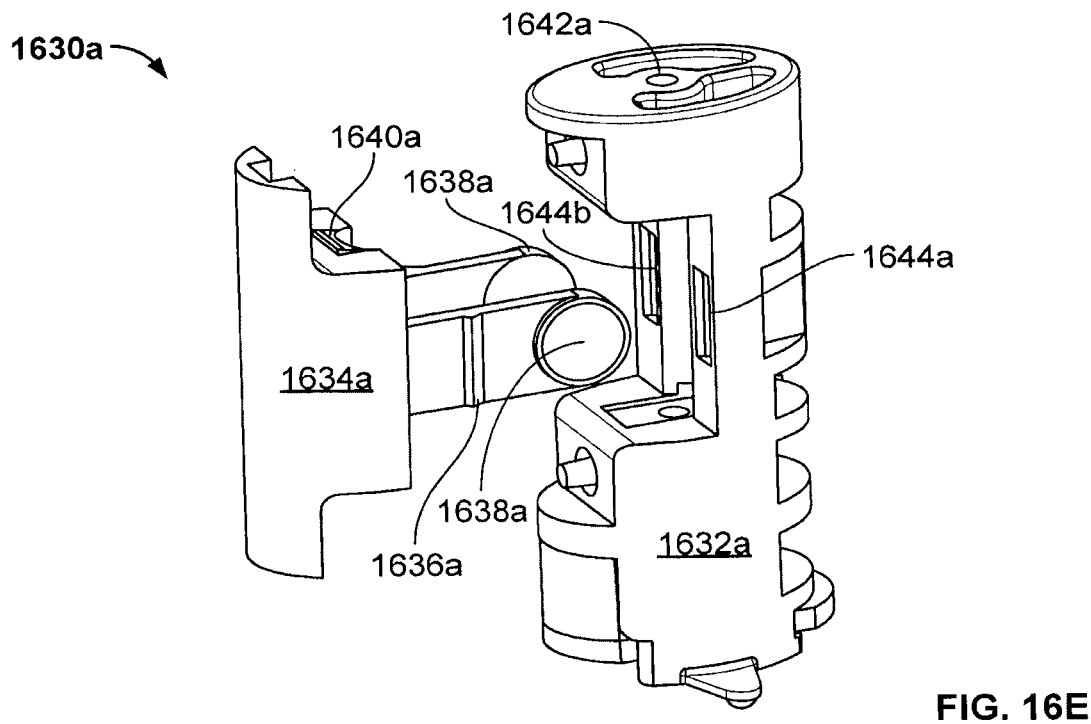
Figure 16F:
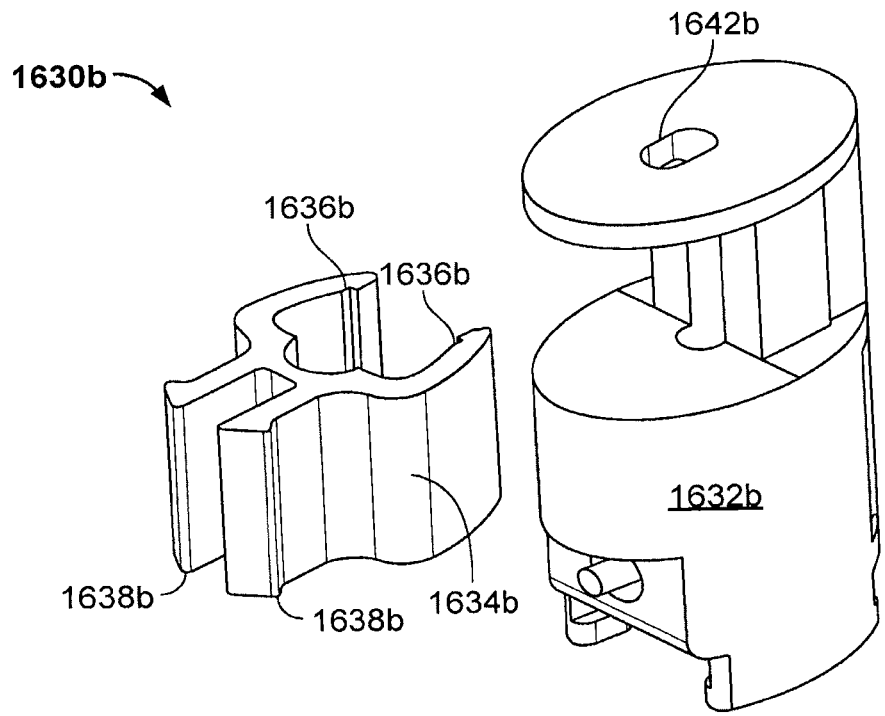
Figure 16H:
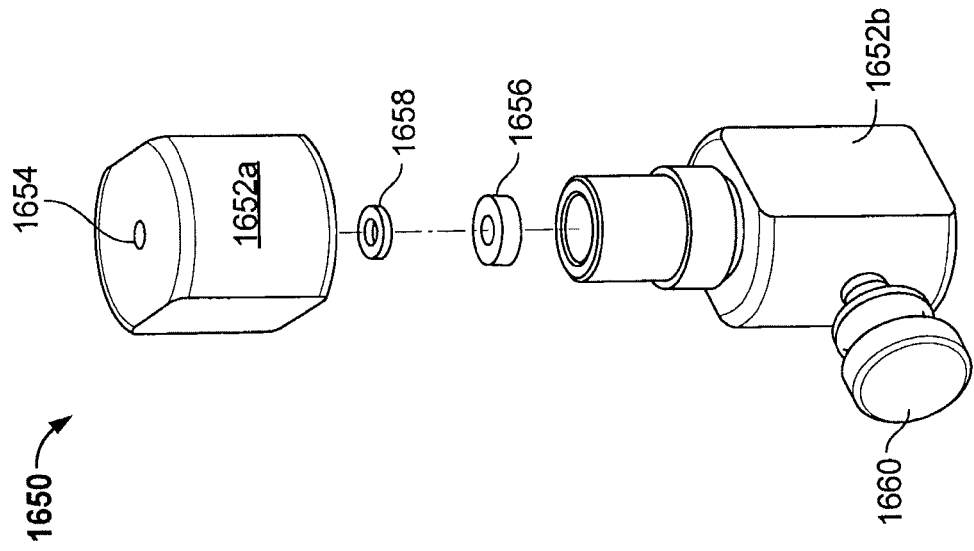
Figure 16G:
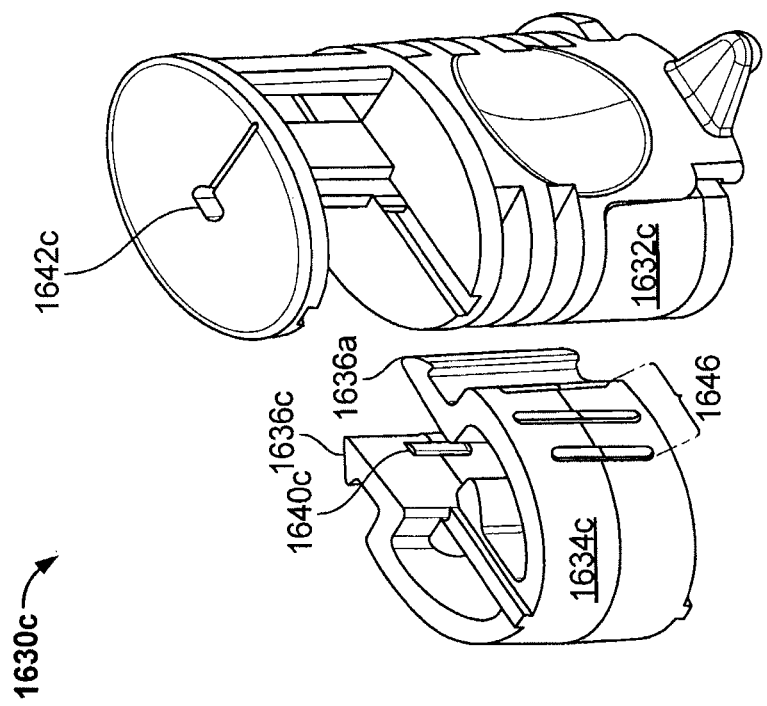

FIGS. 16E through 16G illustrate twin snap style depth locking elements 1630. In a general sense, a twin snap style depth locking element 1630a, 1630b, 1630c functions by positioning a probe through an opening 1642a, 1642b, 1642c and along a length of a body section 1632a, 1632b, 1632c. To releasably attach the twin snap style depth locking element 1630a, 1630b, 1630c to the probe, a locking section 1634a, 1634b, 1634c frictionally snaps onto a mated portion of the body section 1632a, 1632b, 1632c at snaps 1638a. For example, the body section 1644a of the twin snap style depth locking element 1630a of FIG. 16E includes slots 1644a, 1644b for receiving the snaps 1636a of the locking section 1634a.

Twin snap style depth locking elements 1630a and 1630c of FIGS. 16E and 16G additionally include secondary snaps 1640a, 1640c such that the locking section 1634a, 1634c remains connected to the body section 1632a, 1632c when the snaps 1636a, 1636c are disengaged.

To release the probe, for twin snap style depth locking elements 1630a and 1630b of FIGS. 16E and 16F, the operator may squeeze the tabs 1638a, 1638b. For twin snap style depth locking element 1630c of FIG. 16G, the operator may squeeze the locking section at gripping portions 1646 to release. Turning to FIG. 16H, a Touhy Borst style depth locking element 1650 includes body sections 1652a, 1652b configured to releasably thread together. A probe may be positioned through an opening 1654 within the body section 1652a and along a length of the body sections 1652a, 1652b. Upon threading the body sections 1652a, 1652b together, a deformable (e.g., rubber) ring 1656 applies frictional pressure to the probe, locking the Touhy Borst style depth locking element 1650 in place. A washer 1658 reduces friction between the deformable ring 1656 and the upper body section 1652a.

Returning to FIGS. 1E and 1F, the adjustable depth stop 114, in some embodiments, includes features for ease of use and precision positioning. In a first example, each of the portions 114a and 114b include one or more grip indents 124 to enable easier grasp of the portions 114a and 114b when twisting the portions 114a and 114b relative to each other to lock and unlock the adjustable depth stop 114. In a second example, sheath-end portion 114a of the adjustable depth stop 114 may include an alignment marker 126 for aligning the adjustable depth stop 114 with the gradations along the shaft of the probe 112 for precision positioning. The alignment marker 126, in the circumstance of a side-firing probe, may be aligned in the direction of firing of the probe. For example, the gradations on the shaft of the probe 112 may be printed along a line positioned in the direction of firing, such that aligning the alignment marker 126 with the line of the gradations aligns a projection 126 of the probe-end portion 114b of the adjustable depth stop 114 with the side-firing direction of the side-firing probe. In an alternative embodiment, as illustrated in FIG. 1D, a directional marker 130 (e.g., line along the sheath-end portion 114a of the adjustable depth stop 114) may identify a side-firing direction of the side-firing probe.

FIG. 1G illustrates an example enlarged cut-away view of the flexible umbilical sheath 116 of the probe apparatus 100 of FIGS. 1C and 1D. The sheath 116, as illustrated, includes a series of windings 132 and an inner conduit 134. The conduit may be used to carrying inputs and outputs (e.g., energy, control signals, thermocouple wires, a deflection wire, cooling gas or fluid, and/or heating gas or fluid) between the probe 112 of FIGS. 1C and 1D and a control unit (not illustrated). In some examples, the conduit 134 may include one or more tubes, lumens, or other divisions to separate various inputs and outputs directed through the conduit 134. For example, as described in greater detail in relation to FIGS. 10 and 12, the conduit may include a number of lumens or tubes to enable cooling fluid supply to and cooling fluid return from a fluid-cooled probe. The windings 132 provide structure to protect the various components within the conduit 134. In some examples, the windings 132 may be configured to supply a particular kink resistance value, torque strength, and/or tensile strength to the flexible umbilical sheath 116. In one embodiment, the coil structure resulted in optimal kink resistance and a tighter coil (as compared with a looser coil) resulted in better column strength. In another embodiment, one or more of the multiple layers has a braided structure. The flexible umbilical sheath 116 may be designed using non-ferro-magnetic materials for MRI compatibility. For example, the windings 132 may be composed of a polymer or poly-vinyl material. In other examples, the flexible umbilical sheath may be composed of PTFE, PEEK, Polyimide, Polyamide and/or PEBAX, and the winding material may include stainless steel, Nitinol, Nylon, and/or PEEK. The materials of the windings 132 and/or the external covering of the flexible umbilical sheath 116 may be selected in part for thermal stability. In the example of a cryotherapy probe such as the probe described in relation to FIG. 4, the materials of the windings 132 and/or the external covering of the flexible umbilical sheath 116 may be selected to withstand extremely cold temperatures without incurring damage during flexing.

FIG. 1H is an enlarged view of the transitional part 120 positioned between the probe 112 and the flexible umbilical sheath 116 of the variable length probe apparatus 110 of FIGS. 1C and 1D. The transitional part 120 may include one or more indents 136 for grasping the transitional part 120 upon positioning or otherwise manipulating the probe 112. Further, the transitional part 120 may include one or more vents 138 for venting return gasses in a gas-heated or JT fluid-cooled probe.

In some embodiments, a shaft portion of the probe 112 including windings 132 (e.g., at least beginning at a point above the gradations and abutting or extending beyond the transitional part 120, if not continuing throughout the entirety of the shaft portion of the probe 112) may be composed of one or more materials selected at least in part for flexibility of the shaft portion such that the shaft portion may bend away from the skull. Probe shaft materials may include, in one example, polyimide for rigidity in a first shaft portion designed for interstitial deployment, and PTFE for flexibility in a second shaft portion interfacing with the windings 132. Additionally, the first shaft portion and/or the second shaft portion may be composed of multiple layers of material, such as polyimide under an etched layer of PTFE, to provide for better bonding characteristics at the interface between the first shaft portion and the second shaft portion.

Figure 2A:
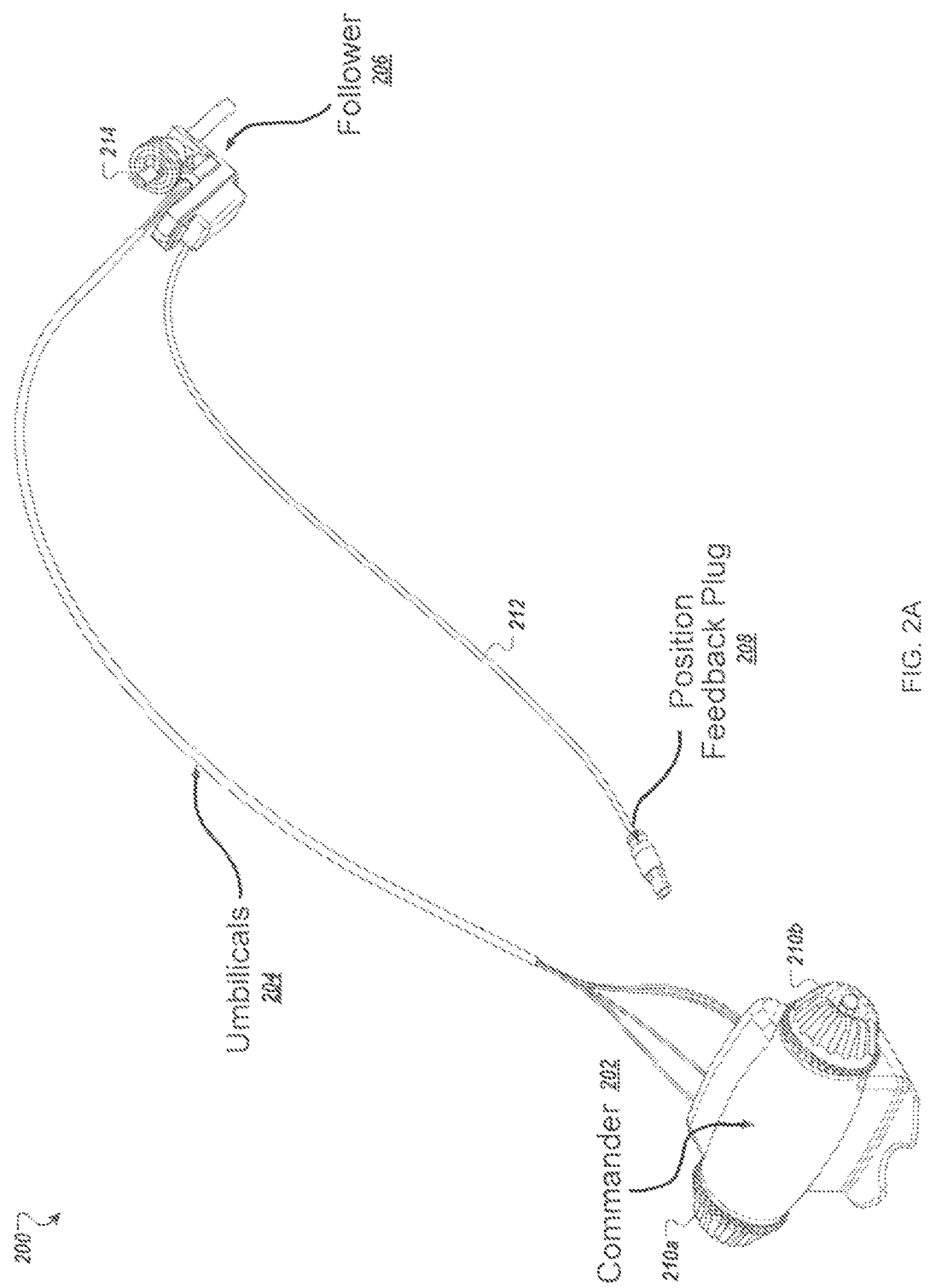
FIG. 2A illustrates an example probe driver.

FIG. 2A illustrates a probe driver 200, which generally includes a commander 202, umbilicals 204, a follower 206, and a position feedback plug 208 that receives position feedback signals, such as potentiometer signals, from the follower 206 via a feedback cable 212. A probe can be inserted into the follower 206, and the follower 206 can control a rotational and longitudinal alignment of the probe.

The probe driver 200 can be mounted to an interface platform, such as the interface platform disclosed in U.S. Pat. No. 8,979,871 to Tyc, entitled "Image-Guided Therapy of a Tissue" and filed Mar. 15, 2013, incorporated by reference in its entirety. The position feedback plug 208, for example, can connect to the interface platform in order to communicate the probe's position to the system. The probe driver 200 is used to rotate or translate (extended or retract) the probe. The probe driver 200 in this illustrated implementation can provide, at a minimum, a translation of 20-80 mm, 30-70 mm, 40-60 mm or 40 mm, with a maximum translation of 60 mm, 80 mm, 100 mm, 120 mm or 60-150 mm. The probe driver 200 in this illustrated implementation can also provide, at a minimum, a rotation of 300.degree.-340.degree., with a maximum rotation of 350.degree., 359.degree., 360.degree., 540.degree., 720.degree. or angles therebetween. Included with the probe driver 200 can be a rotary test tool that can be used during a self-test procedure to simulate an attachment of a probe to the follower 206.

The umbilicals 204 may include sheathed wires that independently control rotational and longitudinal motion of a probe or other device held by the follower 206. Independent control of the rotational and longitudinal motion may be provided, for example, by rotating a respective one of the knobs or dials 210 provided at either side of the commander 202. An example structure for the corresponding mechanisms that provide the rotational and longitudinal motion is described and shown in U.S. Pat. No. 8,728,092, entitled "Stereotactic Drive System" and filed Aug. 13, 2009, the entirety of which is incorporated herein by reference.

In various implementations, the probe driver 200 provides full remote control to an operator that is located either: (1) in the proximity of the imaging apparatus and an interface platform that the probe driver is connected to, or (2) in a remote room, such as a control room, at a workstation, where the workstation sends positioning signals to the interface platform to actuate corresponding movements by the commander 202. Full remote control of the probe driver 200 is thus provided, which reduces procedure time.

Figure 2B:
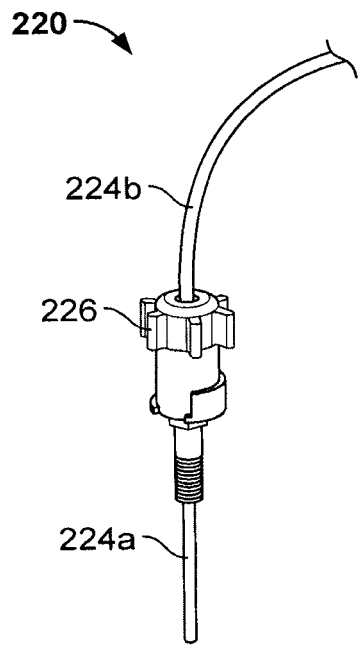
FIGS. 2B-2D illustrate an example probe follower for use with the probe driver of FIG. 2A.
Figure 2C:
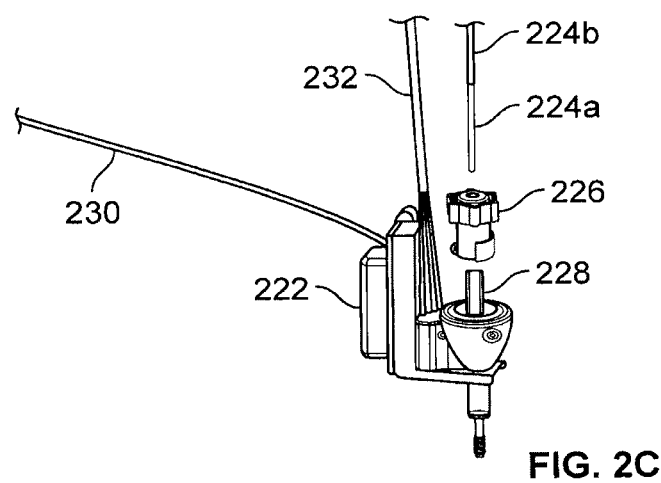
Figure 2D:
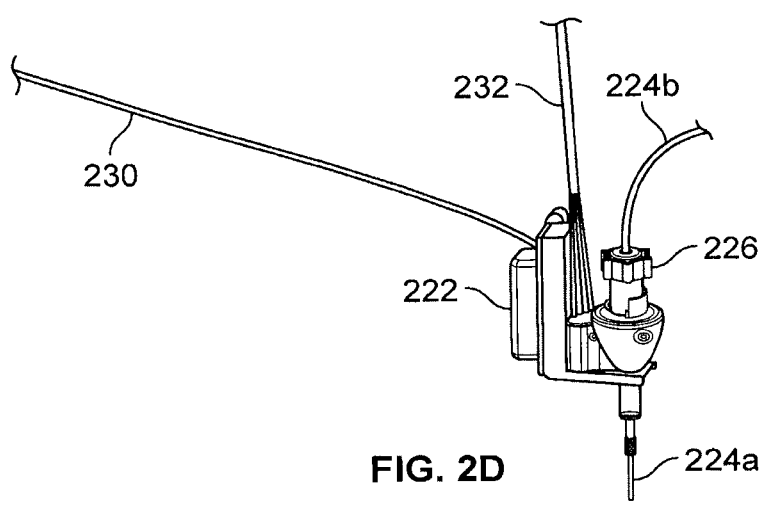

Turning to FIGS. 2B-2D, a series of views illustrate insertion of a variable length probe apparatus 220 into a probe follower 222. Similar to the variable length probe apparatus 110 described above in relation to FIGS. 1C through 1D, as shown in FIG. 2B, the variable length probe apparatus 220 includes a probe portion 224a integrated with or connected to a flexible umbilical sheath 224b. As illustrated, the probe portion 224a is inserted within an adjustable depth stop 226. The adjustable depth stop 226, for example, may be releasable connected to the probe apparatus 220 or slideably integrated with the probe apparatus 220 (e.g., such that it is not configured for removal from the probe 224).

In an implementation illustrated in FIG. 2C, the adjustable depth stop 226 is separated from the probe portion 224a and aligned with a mating protrusion 228 of the probe follower 222. As illustrated in a mating protrusion 214 of the follower 206 of FIG. 2A, for example, the mating protrusion 228 may be a hollow cylinder configured to mate with a larger diameter cylindrical opening of the adjustable depth stop 226. The probe portion 224a, in this example, would be inserted through the cylindrical opening of the mating protrusion 228 of the probe follower 222. For example, as illustrated in FIG. 2D, the adjustable depth stop 226 is mounted upon the probe follower 222 with the flexible umbilical sheath 224 extending above the adjustable depth stop 226 and the probe portion 224a extended out below the probe follower 222. The adjustable depth stop 226, in this configuration, may be mated with the mating protrusion 228 before or after insertion of the probe portion 224a into the adjustable depth stop 226. As with the follower 206, the probe follower 222 includes both a position feedback cable 230 for communicating position signals as well as umbilicals 232 for receiving positioning commands from a commander unit (not illustrated) such as the commander 202 of FIG. 2A.

Multiple different probes can be utilized and swapped into the follower 206 or follower 222 during treatment so as to provide different therapeutic patterns from different probes. For example, a symmetrical ablation probe can be used, followed by a side-fire (asymmetrical) ablation probe. A diffused tip probe can also be utilized.

A process of advancing probe, asymmetrically treating, measuring, advancing probe and repeating is provided, such that the process does not require the interruption of a user-intervention in the surgical room to change probes or probe position.

Further, in some implementations, the follower 222 includes a low profile design with a short stem to enable wider skull access and/or multiple concurrent probe trajectories. FIGS. 2E through 2G illustrate views 240 of the follower 222 with a low profile design. As shown in FIGS. 2E and 2F, a guide rail portion 242 of the follower 222 may have a short stem 244 for ease of interoperability with various skull-mounted probe introduction equipment, such as a bolt-style probe introduction device 256. The short stem 244, in some examples, may be less than 19 mm or between 19 and 32 mm. In some examples, the length of the short stem 244 is less than or about a third the length of the guide rail 242.

As illustrated in FIG. 2E, the follower 222 is mated with a bolt-style probe introduction device 256. Details regarding a bolt-style probe introduction device are provided in U.S. Provisional Patent Application No. 62/132,970 entitled "Apparatus and Methods for Neurological Intervention" and filed Mar. 13, 2015, the contents of which are hereby incorporated by reference in its entirety. The bolt-style probe introduction device 256 may be locked to the follower 222 via a locking mechanism. As shown, the bolt-style probe introduction device 256 is locked to the follower 222 via a hole in the short stem 244 aligned with a thumb screw 254 inserted through a locking sleeve 248. The locking sleeve 248, as illustrated, has a similar length as the short stem 244. In other implementations, the locking sleeve 248 may include an elongated design, for example based upon mating requirements with particular skull-mounted probe introduction equipment. Although described in relation to the thumb screw 254, alternatively, in some examples, a pin and groove design, locking teeth, or clamp lock may be used to lock the bolt-style probe introduction device 256 to the follower 222.

The locking sleeve 248 in some implementations, includes a poka-yoke design 250 such that the locking sleeve 248 naturally aligns with a thread opening 252 of the locking sleeve 248 with the hole 246 of the short stem 244.

The follower 222 with low profile design may be manufactured of thermal imaging compatible materials, such as MRI-compatible materials. Additionally, the locking sleeve 248 and/or thumb screw 254 may be manufactured of thermal imaging compatible materials. In some embodiments, at least a portion of the follower 222 may include imaging system-identifiable material such as a thermal imaging identifiable fiducial marker for use in identifying the location and/or orientation of the follower 222 through medical imaging. In a particular example, a fiducial marker 258, as illustrated in FIG. 2G, may be positioned upon a bottom portion of the guide rail 242. In addition to or in lieu of a fiducial marker 258, in other embodiments, the follower 222 with low profile design may include electronic (e.g., RFID—radio frequency identification) markers and/or visual markers compatible with visual imaging systems.

Figure 3A:
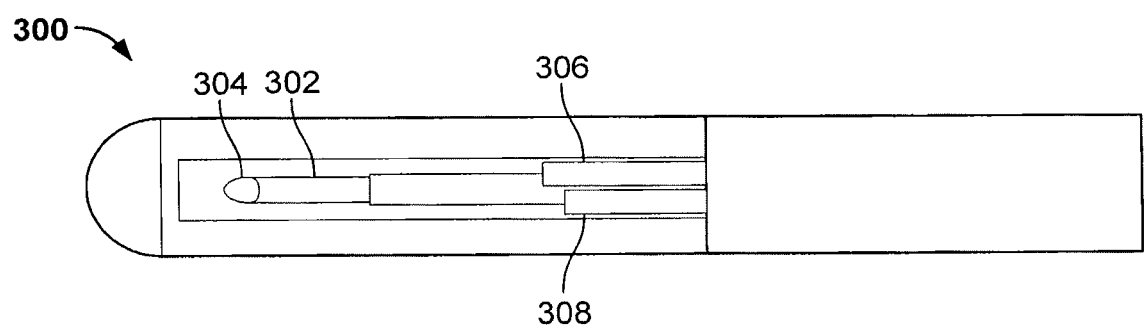
FIG. 3A illustrates an example probe design with built-in thermal modulation.

FIG. 3A illustrates an example temperature modulation probe 300 for modulated application of thermal therapy and cryotherapy using both a thermal therapy-generating element and a cryotherapy-generating element disposed within the temperature modulation probe 300. In use, the temperature modulation probe 300 supplies a modulated temperature output pattern to a target tissue, varying between a warmer temperature applied at least in part by the thermal therapy-generating element and colder temperature applied at least in part by the cryotherapy-generating element. Treatments enabled by the temperature modulation probe 300 may include treatments that create temporary or permanent physical-biological effects to tissue including freezing freeze-thawing, hyperthermia, coagulation, and/or vaporization of tissues. The temporary or permanent physical-biological effects can include alterations in biological function of cells, tissues, and/or body fluids. In a particular example, the treatment may cause the cells, tissues, and/or body fluids to be more receptive or sensitive to additional therapies or manipulations such as, in some examples, radiation therapy or chemotherapy. In a further example, the treatment may cause hemostasis, reduction or dissolution of thrombi or emboli, alteration of functional membranes including the blood-brain barrier, and/or renal filtration. The physical-biological effects may be caused directly by temperature change to the cells, tissues, and/or body fluids or indirectly (e.g., downstream) from the temperature change, such as alterations in heat shock proteins or immune reaction or status. The temperature modulation probe 300 may be designed for insertion into a body cavity, insertion into vascular system, or interstitial deployment.

As illustrated, the temperature modulation probe 300 includes a laser 302 with a side-firing tip 304 as a thermal-therapy generating element. The side-firing tip 304 may further include a side-firing diffuser capable of focal ablation with a lower power density. Examples of side-firing tips and various diffusing patterns for side-firing probes are described in U.S. Pat. No. 8,979,871 to Tyc, entitled "Image-Guided Therapy of a Tissue" and filed Mar. 15, 2013, incorporated by reference in its entirety.

Figure 3B:
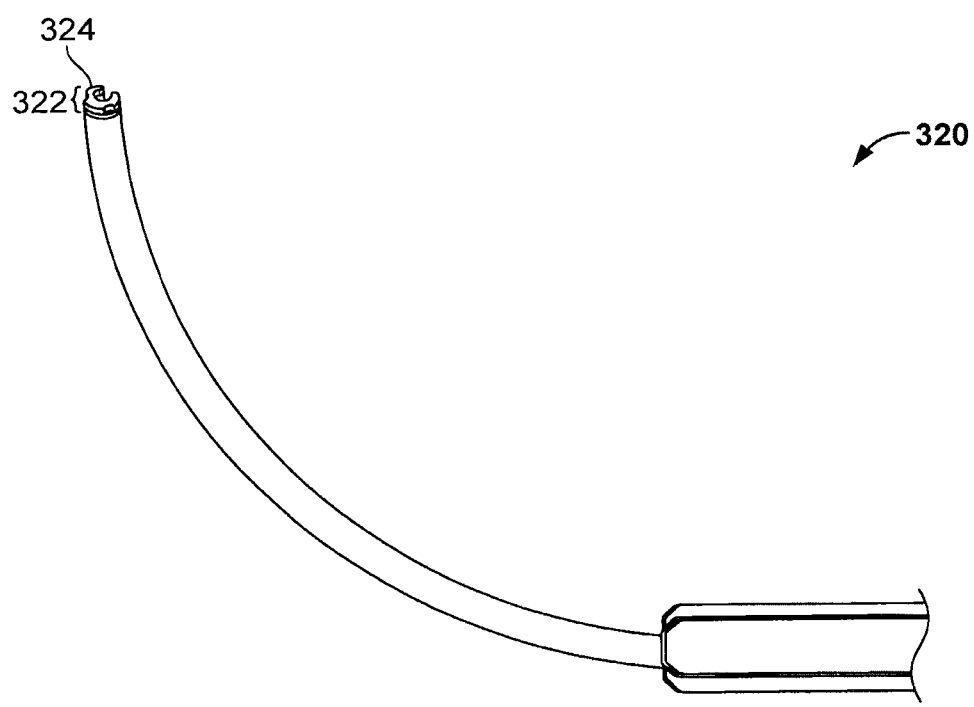
FIG. 3B illustrates an example focal laser fiber.

Although the temperature modulation probe 300 is illustrated with the side-firing laser 302, in other embodiments, the temperature modulation probe 300 includes a forward firing probe tip, such as a probe tip 322 illustrated in relation to the laser probe 320 of FIG. 3B.

In further embodiments, rather than or in addition to the laser fiber 304, the temperature modulation probe 300 may include one or more ultrasound elements and/or ultrasonic transducers capable of focal or diffuse heating using HiFU. The ultrasonic beam of a HIFU probe can be geometrically focused (e.g., using a curved ultrasonic transducer or lens) or electronically focused (e.g., through adjustment of relative phases of the individual elements within an array of ultrasonic transducers). In an ultrasonic transducer array, the focused beam can be directed at particular locations, allowing treatment of multiple locations of a region of interest without mechanical manipulation of the probe. The depth of treatment can be controlled by adjusting the power and/or frequency of the one or more transducers of the HIFU probe. Example HiFU probes are described in U.S. patent application Ser. No. 14/661,170, entitled "Image-Guided Therapy of a Tissue" and filed Mar. 18, 2015, the contents of which are incorporated by reference herein in its entirety.

In additional embodiments, the temperature modulation probe 300 may include a microwave, RF, heating gas, heating fluid, or electrical heat thermal therapy-generating element in lieu of or in addition to the laser 302. A heating fluid thermal therapy-generating element, for example, may circulate a fluid such as helium or hydrogen. Each of the at least one thermal therapy-generating element may be configured to emit thermal energy in a side-firing, focal, or diffuse manner. In a particular example, a temperature modulation probe includes a circumferentially emitting thermal therapy-generating element. The temperature modulation probes of the present disclosure may be designed for insertion into a body cavity, insertion into vascular system, or interstitial deployment.

The temperature modulation probe 300 further includes a cryotherapy-generating element 306 (e.g., cooling gas, cooling fluid, etc.) for supplying cryotherapy to the effected tissue. In some examples, the cryotherapy-generating element 306 may include a flow of fluid such as gaseous carbon dioxide, liquid nitrogen, or liquid argon. The supplied fluid/gas may utilize Joule-Thomson cooling via Joule-Thomson expansion. As described in relation to FIG. 4, for example, a cooling fluid delivery tube with reduced diameter aperture or orifice may be used to deliver a fluid or gas at a predetermined pressure. The restricted orifice or aperture of the fluid delivery tube may be a venturi outlet having a cross-sectional area smaller than a main-body of the cooling tube. Gas or fluid exiting the reduced diameter aperture or orifice, via Joule-Thomson expansion, will expand into an expansion chamber to provide a cooling effect to the tip of the probe 300. Fluids may be provided as a liquid via the fluid delivery tube and, upon expansion into the expansion chamber, the fluid may form a gas, going through an adiabatic gas expansion process through the restricted orifice into the expansion chamber to provide the cooling effect. Alternatively, cooling fluids which do not expand but rather circulate can also be used.

The cryotherapy-generating element 306 may be configured to emit cryotherapeutic energy in a focal, circumferential, or diffuse manner. In some configurations, a probe may include multiple cryotherapy-generating elements 306 and/or multiple supply orifices for a single cryotherapy-generating element 306 to provide a particular deployment shape or pattern. In some examples, multiple orifices may be arranged in a line, a cluster, and/or a circular pattern to form a longer and/or wider cooling pattern at a distal tip of the temperature modulation probe 300. For example, arranging several orifices along the probe tip may provide an ellipsoidal three-dimensional cooling zone extending from the distal tip of the temperature modulation probe 300. In some embodiments, the multiple orifices may be provided via multiple perforations or other openings of a distal tip of the cryotherapy-generating element 306. In other embodiments, each orifice may include a separate venturi nozzles or other release valve, such that the cryotherapy-generating element 306 may produce two or more delivery patterns (e.g., based upon which release valve(s) of a number of release valves is placed in an open position). A controller, such as software and/or firmware, may control the patterning of a multi-nozzle, multi-pattern cryotherapy-generating element 306.

The cryotherapy-generating element 306, in some embodiments, is designed for compatibility with the thermal therapy-generating element. For example, the fluid or gas supplied by the cryotherapy-generating element 306 may be selected to avoid interference with the transmission of heat energy by the thermal therapy-generating element (e.g., will not alter laser light attenuation due to absorption by the coolant fluid).

In some implementations, an energy output pattern of the temperature modulation probe 300 includes simultaneous activation of at least one cryotherapy-generating element and at least one thermal therapy-generating element. For example, emissions of both a cryotherapy-generating element and a thermal therapy-generating element may be combined to refine control of temperature emission of the temperature modulation probe. Modulation may further be achieved by varying output of at least one cryotherapy-generating element relative to at least one thermal therapy-generating element. For example, laser power, pulse timing, RF cycling, HiFU element frequency and/or power, fluid or gas pressure, fluid or gas temperature, and/or flow rate may each be varied to obtain temperature modulating output and/or controlled temperature output.

Figure 4:
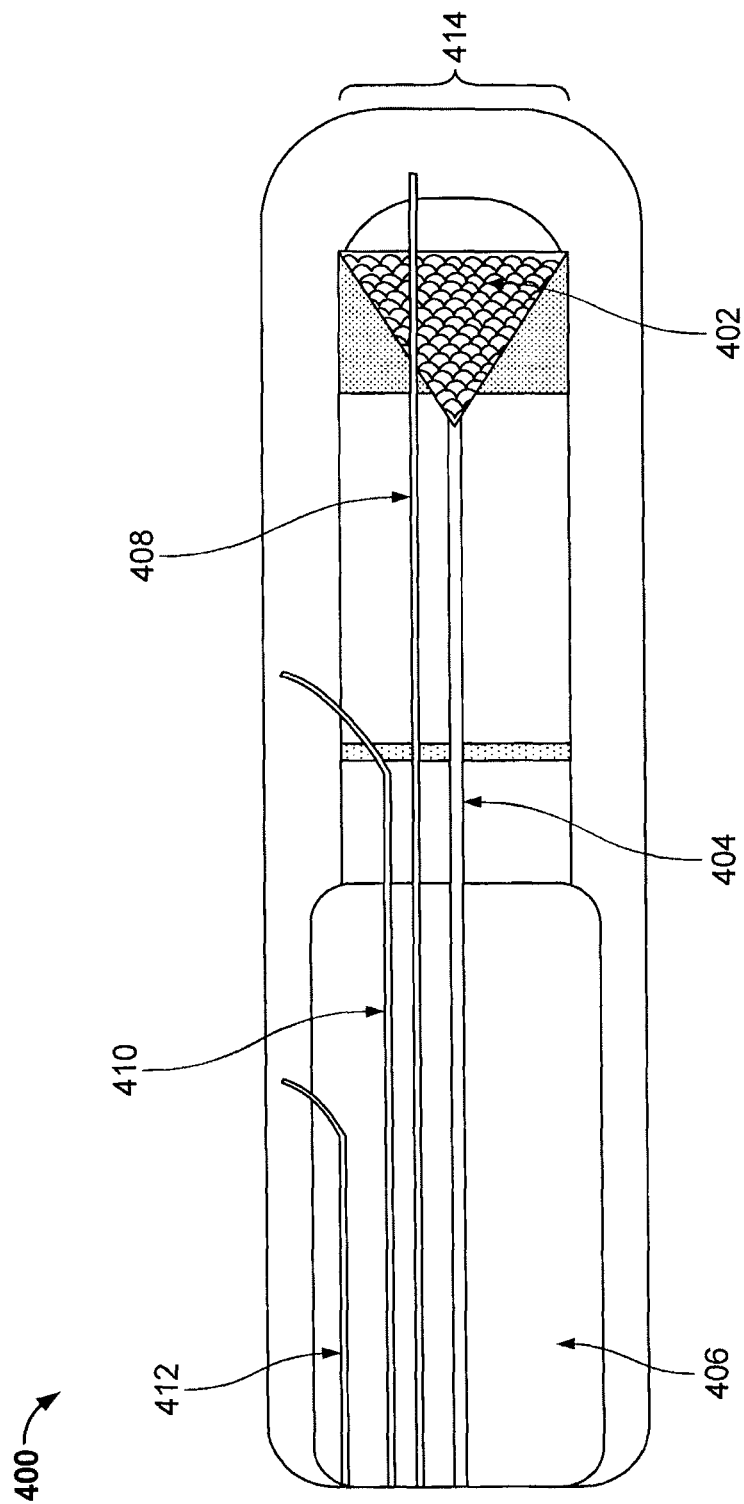
FIG. 4 illustrates an example probe configured for focal cryotherapy.

Temperature production of the temperature modulation probe 300, in some implementations, is refined based upon temperature measurements obtained by a temperature sensor element 308 such as the temperature sensor element 408 described in relation to the probe 400 of FIG. 4.

In some implementations, an on-board processor of the temperature modulation probe 300 controls temperature modulation. Temperature modulation control can be managed by the temperature modulation probe 300, in one example, based upon activation of one or more pre-set patterns programmed into the temperature modulation probe 300. In another example, the temperature modulation probe may maintain or vary a probe temperature (e.g., at the tip of the temperature modulation probe 300) by monitoring temperature measurements gathered by the temperature sensor element 308.

A controller, such as a workstation or computing device, in some implementations, manages temperature modulation of the temperature modulation probe 300 through successively (or concurrently) activating cryotherapy-generating element(s) 306 and thermal therapy-generating element(s) 302 via remotely supplied commands. In additional implementations, the controller may manage temperature modulation of the temperature modulation probe 300 through modifying fluid or gas flow rates, fluid or gas temperatures, laser power and pulse timing, etc.

Further, in some implementations, the controller may manage temperature modulation by modifying output of a fluid or gas within the temperature modulation probe through remotely controlling a release aperture through which the fluid or gas is delivered. For example, as discussed in relation to the probe 400 of FIG. 4, an aperture at the orifice of the gas or liquid injection tube may be remotely controlled.

Figure 6A:
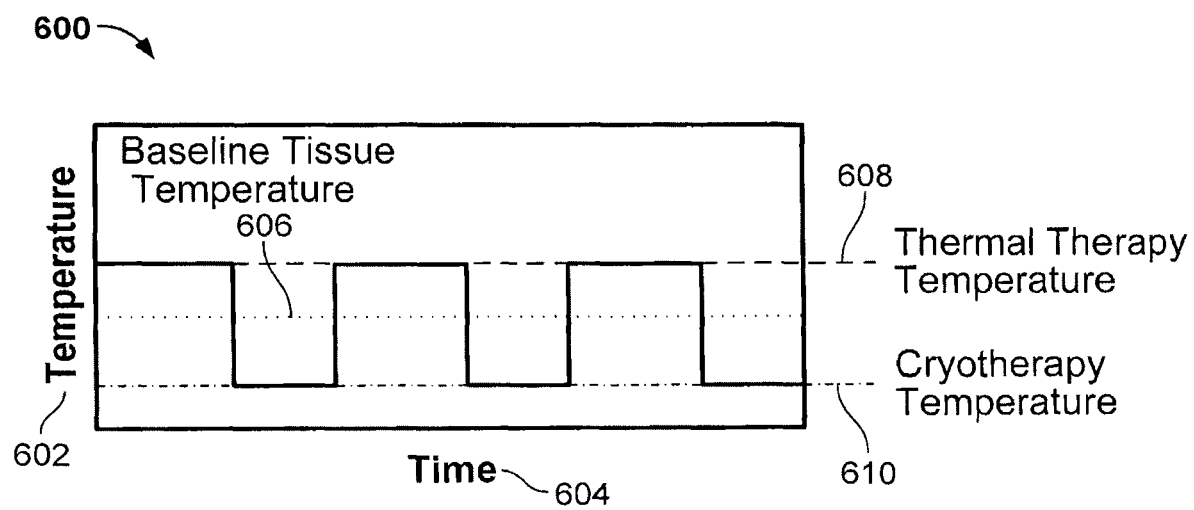
FIG. 6A illustrates a graph of an example modulation pattern for temperature modulation therapy.

Turning to FIG. 6A, a graph 600 illustrates an example modulation pattern for temperature modulation therapy of a tissue using a temperature modulation probe, such as the probe 300 of FIG. 3A. As illustrated, temperature 602 is modulated over a period of time 604 between a thermal therapy temperature 608 above a baseline tissue temperature 606 and a cryotherapy temperature 610 below the baseline tissue temperature 606. Although the time periods of the thermal therapy temperature, in the illustration, appear to be about one third greater than the time periods of cryotherapy temperature, the graph is for illustrative purposes only. In other embodiments, the relative durations of thermal therapy temperature and cryotherapy temperature may vary. In further embodiments, a thermal pattern may include three or more temperature levels. Although illustrated as being modulated about the baseline tissue temperature 606, in yet other embodiments, a thermal pattern may include two or more temperature levels, all above the baseline tissue temperature 606 or, conversely, two or more temperature levels, all below the baseline tissue temperature 606.

The thermal therapy temperature 608 of the example modulation pattern may be applied to the tissue by one or more thermal therapy-generating elements of a temperature modulation probe. In alternative embodiments, the thermal therapy temperature 608 is applied to the tissue by one or more thermal therapy-generating elements of the temperature modulation probe during simultaneous application to the tissue by one or more cryotherapy-generating elements of the temperature modulation probe. In one example, simultaneous application may reduce an overall temperature of the therapy, for example maintaining thermal output in a range of reversible cellular damage or other non-ablative therapy. In another example, simultaneous application may be used to protect tissue within close proximity to the probe from undesirable damage (e.g., charring) while using the thermal therapy-generating elements to cause irreversible cellular damage (e.g., during laser ablation application).

The cryotherapy temperature 610 of the modulation pattern may be applied to the tissue by one or more cryotherapy-generating elements of the temperature modulation probe. Application of a temperature modulation enabled therapy using a temperature modulation probe such as the probe 300 is described in greater detail below in relation to FIG. 8. In alternative embodiments, the cryotherapy temperature 610 is applied to the tissue by one or more cryotherapy-generating elements of the temperature modulation probe during simultaneous application to the tissue by one or more thermal therapy-generating elements of the temperature modulation probe. In one example, simultaneous application may increase an overall temperature of the therapy, for example maintaining thermal output in a range of reversible cellular damage (e.g., when causing hypothermic stress). In another example, simultaneous application may be used to protect tissue within close proximity to the temperature modulation probe from undesirable damage while using the cryotherapy-generating elements to cause irreversible cellular damage (e.g., avoiding intracellular ice development).

Figure 6B:
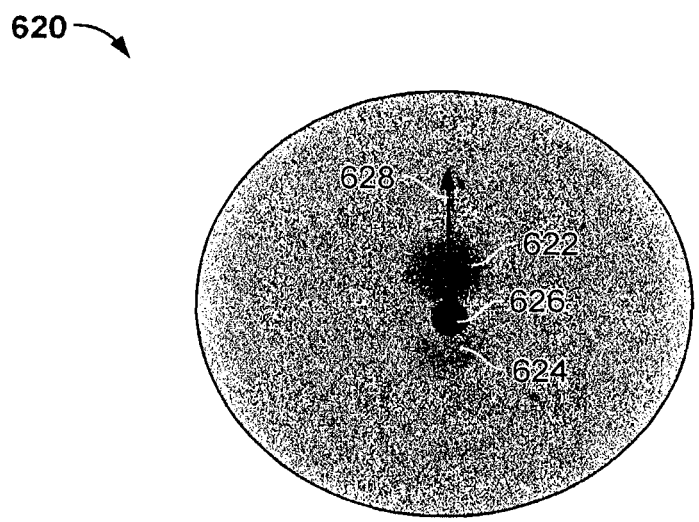
FIG. 6B is a diagram of an example effect upon a tissue caused by temperature modulation therapy by a temperature modulation probe.

FIG. 6B illustrates example effects upon a tissue produced by a temperature modulation probe. Turning to FIG. 6B, a diagram 620 illustrates a heat-exposed region of the tissue 622 (illustrated in red) and a cold-exposed region of the tissue 624 (illustrated in blue) caused by a temperature modulation probe disposed at point 626. The temperature modulation probe 626, for example, includes a side-firing thermal-therapy generating element firing in the direction of arrow 628. The cryotherapy-generating element of the temperature modulation probe may be a diffuse element, causing cryotherapeutic temperatures surrounding the axis of the temperature modulation probe. In a particular example, the effects illustrated in FIG. 6B may be caused by constant diffuse application using a cryotherapy-generating element while modulating application of the thermal therapy-generating element.

Figure 8:
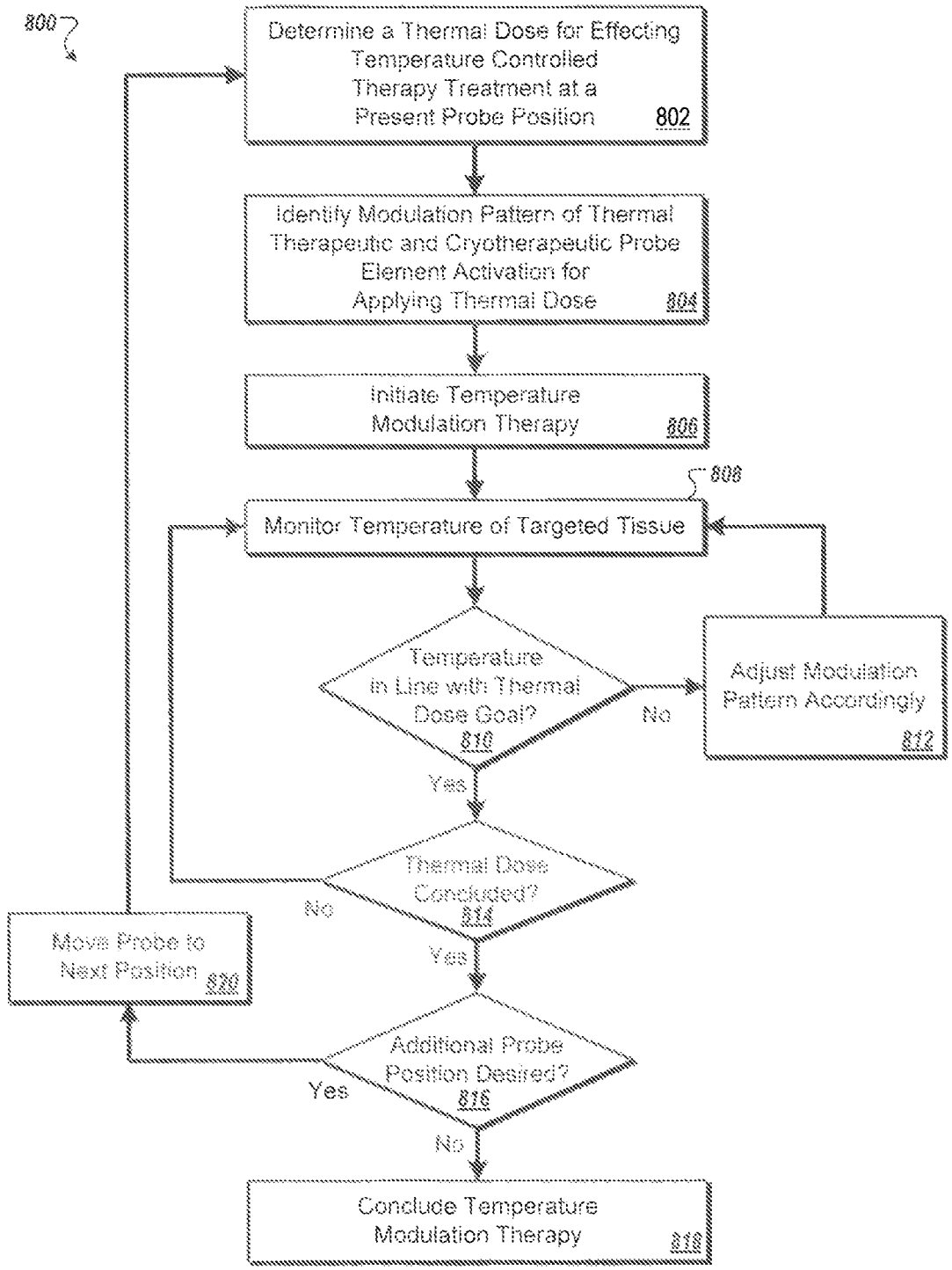
FIG. 8 is a flow chart of an example process for effecting a temperature modulation therapy using a temperature modulation probe.

FIG. 8 is a flow chart of an example method 800 for effecting a temperature modulation therapy using a temperature modulation probe including at least one thermal therapy-generating element and at least one cryotherapy-generating element. The method 800, for example, may be performed using the temperature modulation probe 300 described in relation to FIG. 3A. Aspects of the method 800 may be performed with automated equipment for controlling operation of a temperature modulation probe, such as the commander and follower described in relation to FIG. 2. Aspects of the method 800, for example, may be performed on a workstation or other computing device in communication with the automated equipment for controlling operation of the temperature modulation probe. The workstation or other computing device, for example, may be configured to transmit position control signals to the automated equipment for controlling operation of the temperature modulation probe and/or energy control signals to one or more energy sources, coolant sources, or heat-producing sources delivering energy, fluid, or gas to the temperature modulation probe. The workstation or other computing device, in one example, may be configured to process a sequence of energy, fluid, and/or gas control signals to effect a temperature modulation therapy to the tissue with the temperature modulation probe. Further, the workstation or other computing device may be configured to analyze temperature data received from the temperature modulation probe, a temperature sensor deployed within or near the tissue, and/or a thermal imaging module. Based upon the temperature data analysis, the workstation or other computing device may be configured to modify, suspend, or complete the temperature modulation therapy.

In some implementations, the method 800 begins with determining a thermal dose for effecting temperature controlled therapy treatment at a present position of the temperature modulation probe (802). The present position, for example, corresponds to a particular region of interest of tissue. The thermal dose may include a goal temperature, a goal thermal dose profile, or a goal energy dose profile. Thermal dose profiles, with respect to a specified time period, can include one or more temperatures or temperature gradients for effecting treatment to the particular region of interest. The thermal dose profiles and/or the temperature gradients may permit the determination of an extent of cellular damage in the targeted tissue area and/or other effects upon the targeted tissue area occurring as a result of the temperature modulation therapy. Energy dose profiles may describe energy emissions, over time, which are calculated to cause a particular thermal effect upon the targeted tissue. The thermal dose, for example, may correspond to a desired effect upon the targeted tissue, such as altering normal biological function (e.g., electrical impulse carrying capacity, cytoplasmic enzyme activity, etc.), altering abnormal biological function (e.g., oncogenes, etc.), or influencing cellular activity by an external agent (e.g., drug, chemical, biochemical, etc.). A workstation or computing device, in some embodiments, may determine the thermal dose based upon properties of the region of interest, the desired effect upon the targeted tissue, and/or a type of secondary treatment to be applied at the region of interest (e.g., drug, chemical, biochemical, radiation, etc.).

In some implementations, a modulation pattern of thermal therapy-generating element activation and cryotherapy-generating element activation is identified for applying the thermal dose (804). The modulation pattern may be pre-programmed (e.g., corresponding to the desired thermal dose and/or desired effect) or independently calculated (e.g., using particular properties of the region of interest, desired effect upon the targeted tissue, and/or type of secondary treatment to be applied at the region of interest). Further, the modulation pattern may be static (e.g., applied during the entire temperature modulation therapy) or dynamic (e.g., capable of real-time adjustment based upon temperature monitoring of the tissue during temperature modulation therapy). In other implementations, the modulation may be user-controlled (e.g., user entered and/or user-activated switching between thermal therapy-generating element(s) and cryotherapy-generating element(s).

In some implementations, temperature modulation therapy is initiated (806). In some examples, an operator may physically activate (e.g., depress a button, switch a control) or electronically activate (e.g., via a graphical user interface control element) functionality of the temperature modulation probe. In a particular example, an operator at a workstation may activate temperature modulation therapy by depressing a foot pedal operatively connected to the workstation to activate the first energy or temperature emission of the modulation pattern (e.g., via a corresponding thermal therapy-generating element or cryotherapy-generating element of the temperature modulation probe).

In some implementations, temperature(s) of the targeted tissue is monitored (808). Initiating temperature modulation therapy may further include initiating thermal monitoring of the targeted tissue. In other embodiments, thermal monitoring is initiated separately from temperature modulation therapy. For example, thermal monitoring may begin prior to temperature modulation therapy to establish a baseline temperature and verify functionality of temperature monitoring equipment prior to activation of temperature modulation therapy. One or more temperatures within the target tissue may be monitored. For example, if the thermal dose included a temperature profile corresponding to a desired temperature gradient, multiple temperatures at multiple locations within and/or abutting the target tissue may be monitored. In one example, temperature monitoring includes receiving temperature data from a temperature sensor element built into the temperature modulation probe. In another example, temperature monitoring includes receiving temperature-sensitive imaging data from an imaging device capturing images including the targeted tissue. In a particular example, utilizing MRI imaging in real time guidance may provide controlled accuracy, while contemporaneous thermography may provide accurate temperature information in determining whether a tissue has achieved a goal temperature or temperature profile to producing a desired therapeutic effect.

In some embodiments, temperatures are monitored throughout the temperature modulation therapy. In other embodiments, temperatures are monitored periodically during temperature modulation therapy. For example, due to potential interference with a particular style of emission element, temperature monitoring may be activated during de-activation of that particular style of emission element. In a particular example, temperature monitoring may be activated during emission of the cryotherapy-generating element of the temperature modulation probe but suspended during emission of an RF style thermal therapy-generating element of the temperature modulation probe. Temperature monitoring of a tissue is discussed in greater detail in U.S. Pat. No. 8,979,871 to Tyc, entitled "Image-Guided Therapy of a Tissue" and filed Mar. 15, 2013, incorporated by reference herein in its entirety.

In some implementations, if the temperature(s) is not in line with the thermal dose goal (810), the modulation pattern is adjusted accordingly (812). Depending on the ability of the tissue or surrounding environment to absorb, conduct, or moderate heating or cooling, for example, the actual temperature changes within the target tissue may fail to correspond with the planned tissue temperature(s). For example, temperature(s) in the target tissue may be lower or higher than desired according to the thermal dose. In this circumstance, the modulation pattern driving emission of the temperature modulation probe may be adjusted to effect the desired change (e.g., increase or decrease in target tissue temperature(s)). The workstation or other computing device, for example, may adjust modulation parameters based upon analysis of temperature data.

Temperature modulation therapy may be suspended, in some embodiments, prior to modulation pattern adjustment. For example, if tissue temperatures are outside of a range associated with a desired therapeutic effect (e.g., moving from temperatures associated with reversible cellular damage to temperatures associated with cellular death), temperature modulation therapy may be temporarily suspended while adjusting the temperature modulation pattern. In other embodiments, temperature modulation therapy may continue during the adjustment period.

In some implementations, if the temperature is in line with the thermal dose goal (810), it may be determined that the thermal dose is concluded (814). For example, the thermal dose may correspond to a particular temperature (or temperatures) for a particular period of time or a series of such temperature profiles or temperature gradients. Temperature monitoring may include analyzing historic temperature measurements of the target tissue to verify that the target tissue has reached a particular temperature (or a particular temperature range) for a particular length of time. In other embodiments, determining conclusion of thermal dose includes analyzing the target tissue for evidence of a desired physical-biological effect. The evidence, in one example, may be derived through analysis of image data. In another example, the evidence may be derived through an invasive analysis element, such as the recording elements described in relation to FIGS. 5A through 5H.

In some implementations, if the thermal dose is concluded (814), and an additional probe position is desired (816), the probe is moved to a next position (820). In some embodiments, a rotational and/or linear position of the probe may be adjusted by translating or rotating the probe via automated probe manipulation equipment, such as the commander and follower described in relation to FIG. 2. For example, a workstation or other computing device may direct the automated probe manipulation equipment to reposition the probe to a new rotational and/or linear position. In other embodiments, the probe position is adjusted manually. In one example, the workstation or other computing device may present one or more recommended adjustments (e.g., upon a graphical user interface) for review by a medical professional, and the medical professional may follow the instructions to manually adjust the position of the probe. If the probe position is automatically adjusted, in some embodiments, temperature modulation therapy may continue during repositioning. For example, the temperature modulation pattern may remain active while the probe is translated to a next position. In other embodiments, energy output of the temperature modulation probe may be terminated prior to repositioning.

After adjusting the probe position, in some embodiments, the method 800 returns to determining a thermal dose for effecting temperature controlled therapy treatment at the present probe position (802) and identifying a modulation pattern (804). In other embodiments, the method 800 may continue to use the previously determined thermal dose and/or modulation pattern while proceeding with temperature modulation therapy (806) at the next probe position. The method 800 may thus continue until an entire volume of interest within the targeted tissue has been treated, at which time temperature modulation therapy is concluded (818).

Although described as a particular series of steps, in other implementations, the method 800 may include more or fewer steps. For example, after determining that the thermal dose is concluded (814), and prior to determining whether an additional probe position is desired (816), an additional therapy may be applied to the temperature modulation therapy-treated tissue at the present position. For example, upon preparing the tissue for increased sensitivity to a particular drug or radiation treatment via temperature modulation therapy, the method 800 may include deploying the particular drug or radiation treatment at the present position prior to moving the probe to the next position (820). Secondary treatment, in this example, may be performed by the same probe or an additional instrument. For example, the temperature modulation probe may be retracted into a shared sheath, while a pharmaceutical therapy instrument is supplemented at the same position for performing the secondary treatment. In this example, moving the probe to the next position 820 may involve moving the sheath containing both the probe and the secondary instrument to the next position.

Additionally, in other implementations, steps of the method 800 may be performed in a different order. For example, as discussed above, temperature monitoring of the targeted tissue (808) may begin prior to initiating temperature modulation therapy (806).

As illustrated in FIG. 3B a focal laser probe 320 includes a short lens region 322 (e.g., clear capsule) for focusing the laser. The lens 322, in some examples, may be composed of ceramic polymer, or quartz. The focal laser probe 320 may be used for providing focal thermal therapy through at least one of ablation, coagulation, cavitation, vaporization, necrosis, carbonization, and reversible thermal cellular damage. The focal laser probe 320, for example, may be used to provide focal ablation with minimal edema for minimally invasive neurosurgical applications. The focal ablation provides precision to protect surrounding tissues during thermal therapy, while the minimal edema encourages immediate therapeutic benefit. The focal laser probe 320, for example, may be included as an alternative embodiment of various probes described herein (e.g., probe 300 of FIG. 3A, probe 900 of FIG. 9, the probe of FIG. 11, probe 1300 of FIG. 13A, probe 1400 of FIG. 14A or probe 1500 of FIG. 15A) by exposing only a forward directed tip of the laser fiber and shortening the capsule portion of the respective probe to avoid stray energy transmission, for example due to internal reflections. Additionally, the shortened capsule portion may be easier to manufacture, reducing costs of the focal laser probe.

In designing the focal laser probe 320, a tip portion 324 of the lens 322, in some implementations, is shaped to best direct the focal energy of the tip of the laser fiber. For example, the tip portion 324 may be substantially flat in shape (e.g., potentially with some rounding to enable better penetration of the probe into the tissue region). In another example, the tip portion 324 may be substantially rounded to encourage a substantially even diffuse pattern of focal energy throughout the entire tip portion 324 of the probe 320. In designing the focal laser probe 320 to direct energy from the tip portion 324 of the lens 322 to create ablation zones directly ahead of the probe rather than from the side, the tip portion of the laser fiber itself can be plain (e.g., flat) cut so the energy directly exits the tip of fiber along its axis.

FIG. 4 illustrates an example probe 400 configured for cryotherapy (cryogenic therapy) including at least cryoablation. The probe 400 may include an injection tube 404 for delivering a refrigerant 402 to a tip region 414 of the probe 400. The probe 400 for example, may employ Joule-Thompson cooling to provide a range of temperatures to the tip region 414. For example, The fluid supply to the injection tube 404, in some embodiments, is controlled by a control unit to generate a predetermined pressure within the fluid supply to the injection tube 404 which can be varied so as to vary the flow rate of the refrigerant 402 into an expansion area of the probe 400, thus varying the temperature at the exterior of the tip region 414 abutting the tissue.

In some implementations, the probe 400 may include multiple cryotherapy-generating elements and/or multiple supply orifices for a single cryotherapy-generating element to provide a particular deployment shape or pattern. In some examples, multiple orifices may be arranged in a line, a cluster, or a circular pattern to form a longer and/or wider cooling pattern at a distal tip of the probe 400. In some embodiments, the multiple orifices may be provided via multiple perforations or other openings at an aperture of the injection tube 404. In other embodiments, each orifice may include a separate nozzle (e.g., venturi nozzle, etc.) or other release valve, such that the probe 400 may produce two or more delivery patterns (e.g., based upon which release valve(s) of a number of release valves is placed in an open position). A controller, such as software and/or firmware, may control the patterning of a multi-nozzle, multi-pattern probe 400.

Further, the sizing and/or shape of the orifice(s) may be selected to produce differing effects, such as expanding or contracting (e.g., focusing) deployment of cryotherapy energy. For example, in the circumstance where multiple perforations or release valves are arranged along a length of a tip portion of the probe, the perforations or release valves may include a vent shaping to direct the cryotherapeutic stream in a direction other than perpendicular to the surface of the injection tube 404 at which the particular orifice is positioned.

In some embodiments, the aperture at the orifice of the injection tube 414 and/or individual release valves arranged upon may be mechanically and/or electrically adjustable to vary flow rate of the refrigerant within the probe 400 itself. Further, the size or patterning of the aperture may be adjusted to vary focal diameter of the refrigerant 402 at the tip region 414 of the probe 400, for example by maintaining a flow rate (e.g., via an external control unit) while adjusting the outlet available to the refrigerant at the tip of the injection tube 414.

The aperture, in some examples, may include an adjustable valve or a porous plug. In a particular example, to avoid use of components which may interfere with the imaging system and/or energy producing elements of the cryoablation probe 400, a deflection wire 410 may be used to mechanically manipulate the aperture of the orifice of the injection tube 404. In other embodiments, the deflection wire 410 is used to direct the tip of the injection tube 414 in an offset direction (e.g., in the circumstance of a flexible probe body).

A vacuum return lumen 406, in some embodiments, allows a return cycle of the refrigerant from the expansion region of the probe 400. Thus, the refrigerant is pumped through the injection tube 404 and escapes from the end of the injection tube 404 into the tip region 414 of the probe 400, and then the evaporated refrigerant is returned through the vacuum return lumen 406. From the vacuum return lumen 406, the evaporated refrigerant may be released to the atmosphere or connected to a return tube (not illustrated) to direct the evaporated refrigerant to a return collection. In a particular example, as illustrated in FIG. 1H, the evaporated refrigerant may be released to the atmosphere via the vent 138 of the transition portion 120. In other embodiments, a return tube (not illustrated) is connected to a return collection for the refrigerant. The refrigerant, in some examples, may be liquid nitrogen allowed to expand to nitrogen gas at cryogenic temperatures or liquid argon allowed to expand to argon gas at cryogenic temperatures.

In some implementations, the probe 400 includes a temperature sensor 408 such as one or more thermocouple wires or a fiber optic thermometer. The temperature data generated by the temperature sensor 408, for example, may be provided to a control unit (not illustrated) for monitoring temperature at the tip region 414 of the probe 400. The control unit, responsive to temperature fluctuations may modulate delivery of the refrigerant 402 to maintain (or controllably fluctuate) a temperature at the exterior of the tip region 414. In some implementations, the probe 400 includes at least one electroencephalography (EEG), stereo EEG (SEEG), or electrocardiography (ECG) recording element (e.g., wire, electrode, coil, etc.) 412 for monitoring biological rhythms or electrical signals or activity (e.g., within the brain) during positioning of the probe 400 and/or during cryotherapy using the probe 400. The pulse data generated by the recording element 412, for example, may be provided to a control unit. Uses for the data collected by the recording element 412 are described in relation to FIGS. 5A through 5E, below.

FIGS. 5A through 5E illustrate example options for incorporation of one or more recording elements with a thermal therapy, cryotherapy, or temperature modulation therapy probe such as the probe 300 described in relation to FIG. 3A or the probe 400 described in relation to FIG. 4. FIGS. 5F through 5H, further, illustrate example options for designing a recording instrument including at least one recording element. In some examples, a recording element may include an electrocardiography (ECG) recording element, an electroencephalography (EEG) recording element, and/or stereo EEG (SEEG) recording element.

In some embodiments, a recording element is incorporated into a recording instrument or therapeutic probe for recording signals used to detect abnormal neurological, cardiac, spinal, and/or other in vivo tissue response signals. The recording instrument or probe, for example, may include the ability to electrically stimulate nearby tissue then detect abnormal signals issued by the tissue responsive to stimulation. In another example, the recording instrument may include the ability to thermally stimulate nearby tissue then detect abnormal signals issued by the tissue responsive to stimulation. Detection may involve sub chronical recording and stimulation to detect abnormal signals.

A recording element incorporated into a therapeutic probe, in some embodiments, is used for lesion localization and assessment at the time of cryotherapy or thermal therapy. In lesions without sclerosis, the lesion may not be visually detectable. As such, to appropriately position a probe including a recording element, the recording element may be used detect a signal pattern indicative of the position of the lesion.

In some embodiments, a recording element incorporated into a therapeutic probe is used for detection of critical structures surrounding a target tissue area prior and/or during cryotherapy or thermal therapy. For example, identification of arteries, nerves, functional motor strip within motor cortex, corticospinal track and other critical neural pathways.

In some embodiments, a recording element is incorporated into a recording instrument or probe with a cryogenic energy element and/or thermal energy element for thermally stimulating the tissue. For example, the tissue proximate to the recording instrument or probe may be cooled using a cryogenic energy element to modify signal activity, such as causing brain signal activities detected by an EEG recording element to go into a hibernation pattern (e.g., at less than 10.degree. C.). Through warming (naturally or aided with a thermal energy element), the "wake-up" patterns triggered within the tissue may be detected by the EEG recording element, thus allowing detection of a signal pattern indicative, in some examples, the position of a lesion or an epileptogenic region (e.g., epilepsy onset spot). In another example, the tissue proximate to the recording instrument or probe may be warmed using a thermal energy element to modify signal activity of the effected tissue. In further examples, tissue temperature may be modulated (e.g., cooled and warmed, or vice-versa, two or more times) while identifying epilepsy onset spots or lesions.

A recording element, in some implementations, is incorporated into a recording instrument or therapeutic probe for detecting blood brain barrier (BBB) changes (e.g., effected at about 43.degree. C.). For example, the recording element may detect BBB disruption by identifying Gadolinium presence. In a particular example, electro-chemical sensing of a total amount of charge or electrical current generated by the BBB disruption may be measured to detect the BBB disruption event.

In some embodiments, a recording element of a therapeutic probe provides monitoring during functional neurosurgery. In the example of epileptic symptoms, the recording element may be used to confirm positioning of therapeutic energy for treatment of seizure activity. In another example, a recording element may be used to confirm disruption of the blood-brain barrier. In an additional example, a recording element may be used for monitoring while performing an operation or other therapy, such as monitoring patient biorhythms or electrical activity in the brain and adjusting or suspending therapy if an abnormal event is detected. In another example, the recording element may be used to apply local tissue stimulation responsive to detection of an abnormal event to regulate cellular behaviors during treatment. In particular, the recording element may effect deep brain stimulation during a neurosurgical operation. Further to this example, the recording element may be used to verify efficacy of the local tissue stimulation in modifying the abnormal signals previously detected.

Figure 5A:
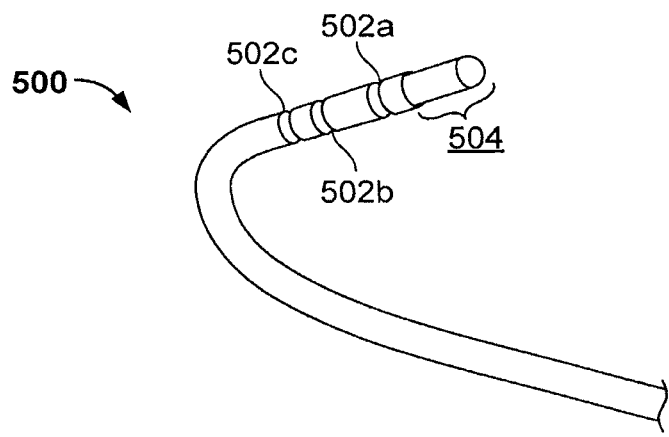
FIGS. 5A through 5E illustrate example options for incorporation of a signal recording element with a thermal therapy, cryotherapy, or temperature modulation therapy probe such as the probe of FIG. 3A or the probe of FIG. 4.

Turning to FIG. 5A, in some implementations, multiple recording elements 502 may be arranged in ring formation along the outer shaft of a probe 500. The recording elements 502, for example, may include individual micro electrodes. In some examples, the recording elements 502 are EEG elements or ECG elements. Although illustrated as including three recording elements 502a-502c, in other embodiments, the probe 500 may include more or fewer recording elements 502, such as five or ten recording elements 502. As illustrated, the recording elements 502 are positioned at a distance from an emission region 504 (e.g., capsule, lens, or other heat, cool, and/or energy emitting portion of the probe 500). In one example, the recording elements 502 may be separated from the emission region 504 to avoid interference with the cryotherapy element(s) and/or thermal therapy element(s) of the probe 500.

Figure 5B:
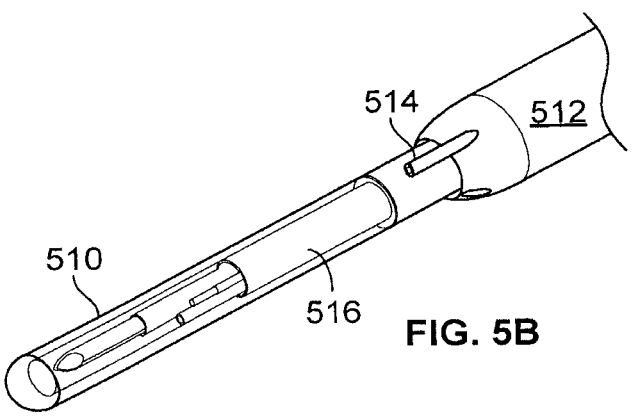
Figure 5C:
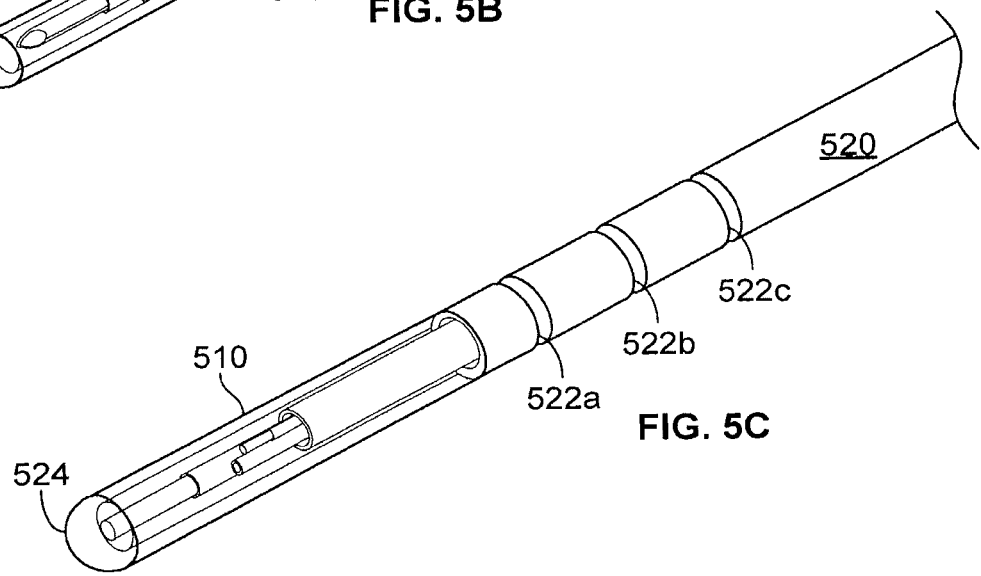

Turning to FIGS. 5B and 5C, in some implementations, a probe 510 may be inserted into a guide sheath or sleeve incorporating one or more recording elements. As illustrated in FIG. 5B, the probe 510 is inserted through a guide sheath 512 having at least one lumen 514 for deployment of a recording element or recording element array alongside the shaft of the probe 510. To avoid interference, in the illustrated embodiment, the recording element/array may be extended only during periods of probe inactivity (or inactivity of those element(s) capable of interference with recording element/array) and/or extended only far enough to avoid interference during therapy (e.g., extended along the length of an internal sheath 516 of the probe 510). In other embodiments, the recording element is included within the outer tube of the probe design. For example, in a multi-lumen probe design such as the lumens 904 through 906 of FIG. 10 described in relation to the probe 900 of FIG. 9, a separate lumen may be provided for inclusion of the lesion detection element along an external surface of the probe (e.g., similar to the lumen 514 of the guide sheath 512). In positioning the recording element within a separate lumen, for example, the recording element 500 may be shielded in part from heating, cooling, and/or EMC effects.

As illustrated in FIG. 5C, the probe 510 is inserted into a sleeve 520 including multiple recording element rings 522. The sleeve 510, in some embodiments, is formed of flexible material, for example to snuggly wrap around the probe 510. The stretchiness of the sleeve 520, in some embodiments, may be selected to accept a range of probe diameters. In another example, the sleeve may be formed of stiffened material, shaped to surround the probe 510. The recording element rings 522 may each be connected to a recording element lead (e.g., wire) delivering signals recorded by the recording element rings 522 to an external device for analysis.

In some embodiments, the probe 510 may be extended and retracted within the sleeve 520. For example, when the probe 510 is inactive and signals collected by the recording element rings 522 are being monitored, the probe 510 may be retracted within the sleeve 520 such that the recording element rings 522 are deployed as close as possible to the tissue near a tip region 524 of the probe 510.

In some embodiments, a recording element/array may be included inside a probe. For example, the recording element/array may be included within a same lumen as one or more other elements of the probe, such as the temperature sensor 408 described in relation to FIG. 4. In another example, the recording element/array may be included in a separate lumen with an external access, such that the recording element/array may be deployed externally to the probe's outer sheath, and then retracted when not in use.

Figure 5D:
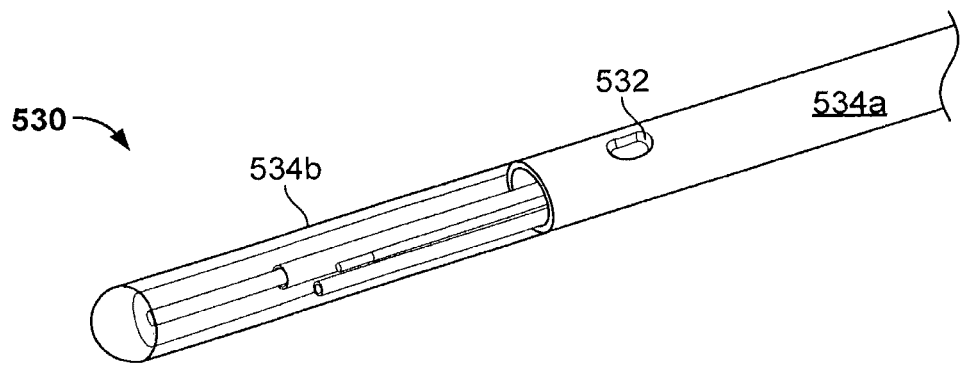
Figure 5E:
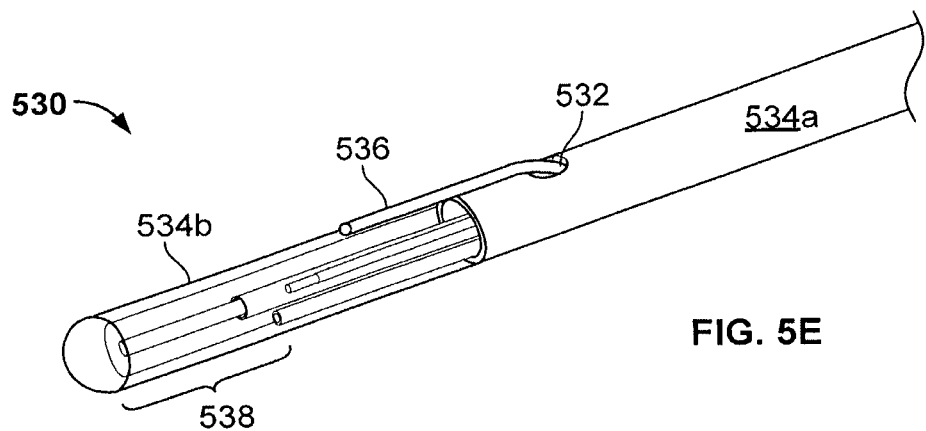

As illustrated in FIG. 5D, a probe 530 includes a port 532 in a side of a shaft section 534a. Turning to FIG. 5E, a recording element 536 (e.g., electrode) is extended through the port 532 along the side of a capsule section 534b of the probe 530 to utilize the features of the recording element 536. In this manner, the probe 530 may be positioned at the target tissue prior to deployment of the recording element 536. In some embodiments, the recording element 536 is configured for deployment short of an emission region 538 of the probe 530, for example to avoid interference between the recording element 536 and therapeutic emissions of the probe 530. In other embodiments, the recording element 536 may be extended within the emission region 538 or even beyond the tip of the probe 530. The recording element 536, in some implementations, includes an angled shape to allow deployment of the recording element 536 through the port 532 to a stop point. In other examples, the recording element 536 is a flexible electrode, such that it may be deployed at variable distances beyond the port 532. Although illustrated as a single port 532 and recording element 536, in other embodiments, the probe 530 may include multiple ports 532 and multiple recording elements 536. In further embodiments, the probe 530 may include a recording array deployed from the single port 532.

As illustrated in FIGS. 5F through 5H, in some implementations, a recording instrument 540 is designed for collecting and analyzing signals obtained by one or more recording elements, such as recording elements 542 and 543. The recording instrument 540, for example, may be designed with an outer diameter between 0.75 and 1.22 mm for intracranial placement. As shown in FIG. 5F, a first recording element contact surface 542a is disposed at a tip of the recording instrument 540, and a second recording element contact surface 543a is disposed along a shaft region of the recording instrument 540. Turning to FIG. 5G, a cross-sectional view 550 of the probe 540 illustrates a first recording element lead 542b and a second recording element lead 542b disposed along the shaft region of the recording instrument 540. The recording element leads 542b, 543b, for example, may connect to a connection unit 562. Further, signals supplied by the recording element leads 542b, 543b may be provided to an external analyzer, controller, and/or recording device via a lead connection 572 of the connection unit 562. Although described as a lead connection 572, in other embodiments, the connection unit 562 may be designed for wireless transmission of the recording element signals, for example via a Bluetooth, Wi-Fi, or other NFC connection to a wirelessly connected recording and/or analysis device.

The recording instrument 540, in some implementations, includes an outer tubing 552 of an insulating material, such as the signals recorded by the recording element contact surfaces 542a, 543a are isolated from each other. In a particular example, the outer tubing 552 is formed of a flexible polymer. The contact surfaces, for example, may be integrated with the flexible polymer material.

In some implementations, the recording instrument 540 includes a coolant supply tube 546 for delivery cooling fluid or gas to a cooling zone region 544 of the recording instrument 540 (as illustrated in FIG. 5F). The cooling fluid or gas, for example, may be introduced at a cooling gas input 568 of the connection unit 562. Further, the cooling gas (or expanded cooling fluid) may be exhausted from the recording instrument 540 via an exhaust chamber 554 disposed along the shaft of the recording instrument 540 (as illustrated in the cross-sectional view 550 of FIG. 5G) and out an gas exhaust port 570 of the connection unit 562. Alternatively, the gas exhaust port 570 may be replaced by a collector assembly for return collection and recycling of coolant.

The connection unit 562, in some implementations, includes a control module for regulating coolant pressure and/or flow rate to provide a desired temperature to the cooling zone region 544 of the recording instrument 540. The control module, for example, may monitor temperature within the cooling zone region 544 through temperature sensor signals supplied by a temperature sensor 548 (e.g., thermocouple) and modulate coolant feed accordingly to maintain a desired temperature or temperature modulation pattern. Additionally or alternatively, coolant pressure may be manually adjusted via a manual pressure control valve 566 of the connection unit 562.

In a particular example, the connection unit 562 may modulate temperatures of tissue within 0.8 and 1.22 mm of the cooling zone region 544 of the recording instrument 540 by first cooling the tissues using the cooling gas (e.g., via JT cooling as discussed, for example, in relation to FIG. 4) and then allowing the tissue to warm. Rather than allowing the body to return to a baseline temperature, in some embodiments, the connection unit 562 may deploy thermal energy to the cooling zone region 544 to encourage warming of the tissues. In a particular example, the connection unit 562 may supply warming gas or fluid. In another illustrative example, the connection unit may alter gas pressure of the coolant to encourage increased temperature at the cooling zone region 544 of the recording instrument 540. The Joule-Thomson principle can be used to either warm or cool a gas expanding through a throttling device such as the cooling injection tube. Depending on the J-T inversion temperature, some gases may warm when expanded (e.g., Helium or hydrogen) and other gases cool (e.g., $CO_2$, nitrogen, argon).

In some implementations, the connection unit 562 includes a temperature readout display 564. For example, the control module may translate temperature signals supplied by the temperature sensor 548 into digits for presentation upon the temperature readout display 564 for review by a medical professional.

Although illustrated as connecting to a single recording instrument 540, in other implementations, the connection unit 562 may be configured to provide input/output connections for two or more recording instruments 540. For example, between two and ten recording instruments 540 may be positioned at various locations within a patient, and the recording instruments 540 may be configured for thermal modulation control and/or analysis via the single connection unit 562.

Figure 5I:
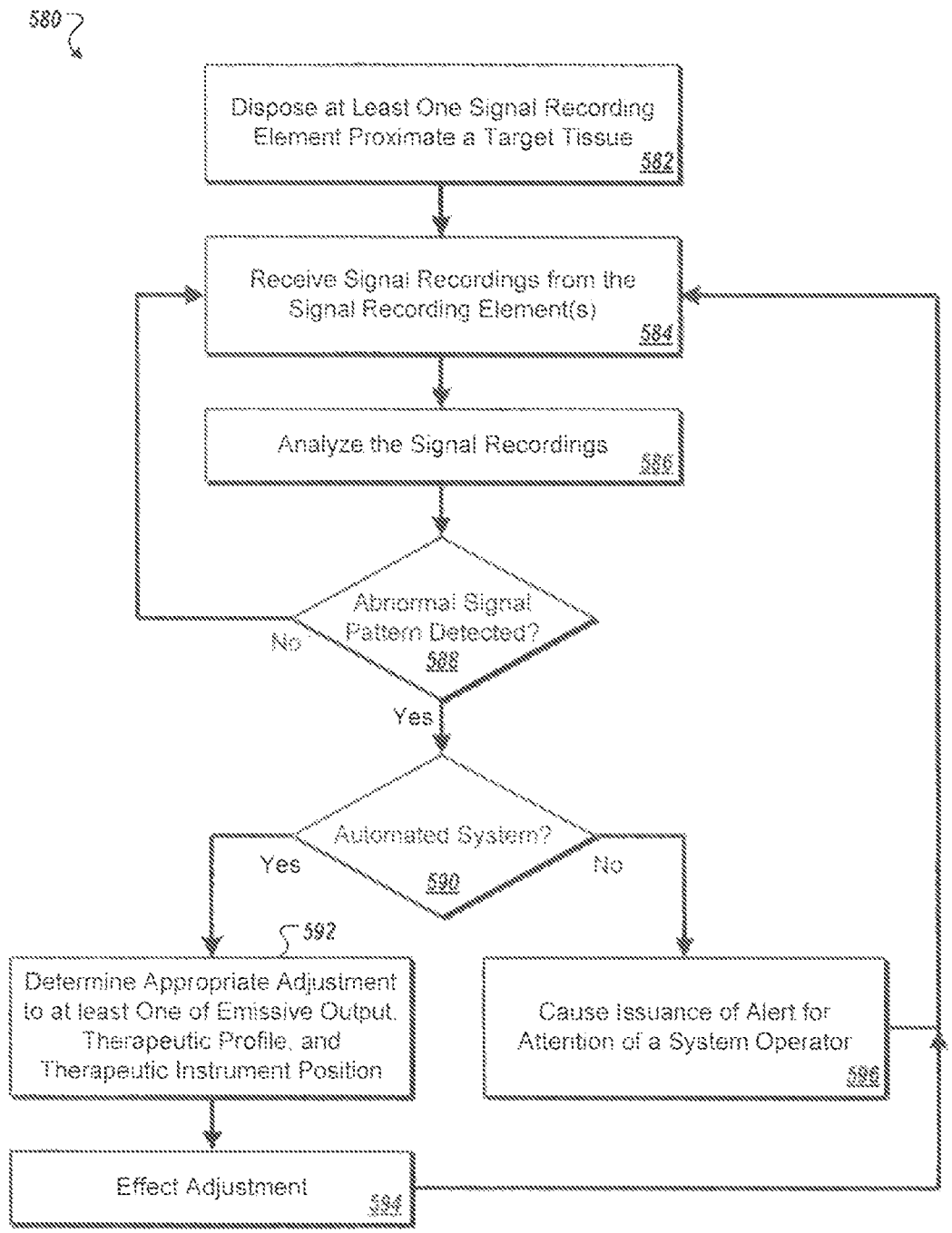
FIG. 5I illustrates a flow chart of a method for using interstitial signal recording elements, such as the recording elements described in relation to FIGS. 5A through 5G.

FIG. 5I illustrates a flow chart of a method 580 for using interstitial signal recording elements, such as the recording elements described in relation to FIGS. 5A through 5G. The method 580, in some embodiments, may be performed at least in part by processing circuitry of an interstitial probe. In some embodiments, the method 580 may be performed at least in part upon processing circuitry separate from the device including the recording element, such as a controller in wired or wireless communication with the device including the recording element. In a particular embodiment, signals read by one or more recording elements may be collected by collection circuitry, and processing circuitry in wired or wireless communication with the collection circuitry may perform subsequent steps of the method 580. Other permutations are possible.

In some implementations, the method 580 begins with disposing at least one signal recording element proximate a target tissue (582). The tissue, in some examples, may include brain tissue, spinal tissue, or pericardial tissue. In some embodiments, the signal recording element is a separate device (or, optionally, a set of signal recording elements may be included within a single device). For example, as illustrated in FIGS. 5F through 5H, the recording instrument 540 may include one or more rings of recording elements (e.g., such as the rings 502 illustrated in on the probe 500 of FIG. 5A). In other embodiments, the signal recording element is coupled to an interstitial therapy instrument. FIG.

5B, for example, illustrates both a recording instrument and a probe deployed via a same guide sheath, while FIG. 5C illustrates a recording element sheath surrounding the probe. In further embodiments, the signal recording element is integrated into an interstitial therapy instrument. For example, as illustrated in FIGS. 5A 5D, and 5E the recording elements are integrated into the probes.

In some implementations, signal recordings are received from the signal recording element(s) (584). The signals may be recorded in a continuous or periodic manner. For example, signals may be recorded opposite an energy emission pattern of a probe deployed with (e.g., proximate to, coupled to, or integrated with) the signal recording element(s) such that the energy emission pattern is not disrupted by the signal recording element(s) or vice versa. The signals recordings may include discrete signal measurements and/or signal patterns sensed over a period of time. The signals, in some examples, may optionally be filtered, amplified, or otherwise adjusted prior to receipt by the method 580. Further, in some embodiments, the signal recordings may be provided with contemporaneous data such as, in some examples, time stamp data, tissue temperature recording data, probe temperature recording data, therapeutic emission pattern data, and/or biometric data (e.g., heart rate, pulse rate, breathing rate, etc.) of the patient.

In some implementations, the signal recordings are analyzed to detect an abnormal signal pattern (586). Analysis may include monitoring for abnormal signal patterns indicative of one or more of a brain tissue hibernation pattern, a brain tissue warm-up (e.g., post hibernation) pattern, a seizure activity pattern or pre-seizure activity pattern (e.g., epilepsy onset spot), location of a lesion, location of a critical structure (e.g., artery, nerve, functional motor strip within motor cortex, corticospinal track, and/or other critical neural pathways, etc.), alterations in the blood brain barrier (e.g., disruption of the BBB), abnormal biorhythms, or other electrical activity markedly different from a baseline for the tissue region (e.g., brain, thoracic cavity, spinal region). In some embodiments, analysis includes coordinating signal data with additional brain activity measurement data, for example derived non-invasively through imaging or other means. For example, analyzing the signal recordings may include analyzing the signal recordings in light of magnetoencephalography (MEG) data or in an effort to confirm MEG data. Further, in some embodiments, analyzing the signal recordings includes analyzing the signal recordings in light of historic signal recording data. For example, detecting an abnormal signal pattern may include detecting movement from previously recorded abnormal signal pattern to a desirable (e.g., normal, healthy, or indicative of success of a therapeutic treatment) or baseline signal pattern.

In some implementations, if an abnormal signal pattern is detected (588) and the recording elements are part of an automated system for therapeutic treatment using an interstitial therapy instrument, an appropriate adjustment to at least one of an emissive output, a therapeutic profile, and a therapeutic instrument position is determined (592). In a first example, the abnormal signal pattern may identify position of a lesion, and adjustment of the emissive output may include delivery of treatment (e.g., thermal therapy, cryotherapy, and/or pharmacological therapy, etc.) to the lesion. In another example, the abnormal signal pattern may identify disruption of the blood brain barrier, and adjustment of therapeutic profile may include shortening a timeframe for delivery of a therapeutic treatment. In an example related to therapeutic instrument position, the abnormal signal pattern may be indicative of location of a critical structure, and the position (e.g., linear position, rotational position, etc.) may be adjusted to avoid damage to the critical structure. The examples are provided for illustrative purposes only, and are in no way mean to be limiting to the opportunities for automated response to detection of an abnormal signal pattern recorded by the signal recording element(s).

In some implementations, after determining the appropriate adjustment, the appropriate adjustment is effected (594). As presented in greater detail, for example, in U.S. Pat. No. 8,979,871 entitled "Image-Guided Therapy of a Tissue" and filed Mar. 15, 2013 (incorporated by reference herein in its entirety), a probe driver may be activated to adjust physical position of the thermal therapy instrument. In another example, as discussed in greater detail in relation to FIGS. 6A and 6B, emission output and/or emission patterns may be adjusted by the controller (e.g., onboard the probe or external thereto) of a thermal therapy, cryotherapy, or temperature modulation therapy instrument. Prior to effecting an adjustment, in some embodiments, the method 580 may prompt an operator for approval to effect the adjustment. For example, a visual and/or audible prompt may alert the operator to the option to effect the recommended adjustment. Effecting adjustment, further, may include prompting an operator to manually perform one or more adjustments.

In some embodiments, if the system is not designed for automated adjustment (590), an alert may be issued for attention of a system operator (596). For example, a visual output including a signal pattern display (e.g., graph, chart, or other illustration indicative of the received signal recordings) and/or signal pattern identifier (e.g., visual arrangement and/or text indicative of particular type of abnormal signal pattern) may be presented upon a display device provided for the system operator. In another example, an audible alert, such as a verbal message, a warning tone, or a series of intonations representative of an abnormal signal pattern may be output for the system operator via a speaker device.

Whether or not an abnormal signal pattern was detected 588, in some implementations, the method 580 proceeds to continue to receive signal recordings (584).

Although described as a particular series of steps, in other implementations, the method 580 may include more or fewer steps. For example, after disposing the signal recording element(s) proximate a target tissue (582) and prior to analyzing the signal recordings (586), the method 580 may receive additional data recordings (e.g., as described in relation to step 586) separate from the signal recordings (e.g., from one or more separate instruments or systems). In another example, after detecting the abnormal signal pattern (588), rather than issuing an alert or determining an adjustment, the method 580 may simply log the abnormal signal pattern (e.g., for later use as historic signal pattern data).

Additionally, in other implementations, steps of the method 580 may be performed in a different order. For example, the method 580 may initially deliver therapeutic output, then receive (584) and analyze (586) signal recordings in an effort to determine success of the delivered therapeutic emission. Other modifications of the method 580 are possible while remaining within the scope and purpose of the method 580.

FIGS. 13A-B, 14A-B, and 15A-C illustrate various embodiments of reduced profile probe designs. Reducing the profile of a probe is desirable for achieving minimally invasive surgery, performing surgical operations upon small bodies such as infants, juveniles and animals, and reaching otherwise difficult-to-reach in situ locations without negatively impacting surrounding tissues. A reduced profile probe, for example, can allow entry into small and narrow spaces in the brain while reducing patient injury. However, reducing the profile of a probe may adversely impact the cross-sectional area of a lumen inside the probe, as well as adversely impact thermal and mechanical properties as a result of reducing wall thickness of a probe shaft. The low profile probe, for example, may have a shaft substructure that has a reduced outside diameter to achieve the desired low profile for expanded lesion location and access while maintaining the desired properties (e.g., mechanical and/or thermal properties) to allow for the desired therapy procedures.

In some embodiments, single-layer low profile probe shafts are designed with a thermoplastic material having a glass transition temperature higher than 100.degree. C. and a Young's Modulus of higher than 2 GPa for effecting thermal therapy by delivering energy to a targeted tissue area, such as brain tissue. In an exemplary embodiment, the energy modality is laser light and the thermal therapy is laser induced interstitial thermal therapy (LITT). The low profile probes described below, for example, may be used to effect reversible cellular damage and/or cellular death (ablation) as discussed above.

As discussed in further detail below, low profile probes may be configured with selected materials, lumen structures, and layer structures to provide desired and/or selected mechanical properties including straightness, rigidity, torque strength, column strength, tensile strength, kink resistance, and thermal properties such as thermal stability and thermal stress capacity. In some embodiments, the low profiled probes are MR-compatible. Maintaining the desired and/or selected mechanical and/or thermal properties, for example, can allow for remotely controlling and operating the low profile probe in a rotational and/or axial direction. In particular implementations, low profile probes are designed such that the tensile strength, torque strength, and column strength are greater than approximately 15 N and the kink resistance is such that no damage to the probe results at curvature radiuses higher than approximately 40 mm. In some embodiments, the low profile probe shaft is air-tight to support modulated heating and cooling operations, such as the temperature-modulation probe designs and uses described above.

Low profile probe dimensions may vary, in some examples, based upon the style of the low profile probe (e.g., thermal therapy, cryotherapy, temperature modulation therapy), the anticipated probe deployment (e.g., intracranial, spinal, cardiac, etc.), the required thermal tolerances of the low profile probe, and/or the required structural tolerances of the probe (e.g., flexible vs. rigid). The wall thickness of the probe shaft, in particular, is related to the stiffness of the low profile probe, which helps the low profile probe stay on trajectory (or allows the probe to deflect therefrom). The following are examples of low profile probe dimensions. In a first example, the inner shaft of a low profile probe has an outer diameter of 2.0 mm, within a tolerance of 0.03 mm and an inner diameter of 1.5 mm, within a tolerance of 0.03 mm; in this embodiment, the sapphire lens has the same inner diameter. In a second example, the outer shaft of the low profile probe has an outer diameter of 2.25 mm, within a tolerance of 0.03 mm and an inner diameter of 2.07 mm, within a tolerance of 0.03 mm. In further examples, the shaft of various low profile probe designs may have an outer diameter of approximately 2.1 mm, approximately 2.2 mm, or less than approximately 3.2 mm. In additional examples, the shaft of various low profile probe designs may have an outer diameter of approximately 1.0 mm or approximately 1.2 mm.

In some implementations, a low profile probe includes multiple internal lumens. The multi-lumen structure, for example, can provide a greater cross-sectional lumen area relative to the profile of the low profile probe while, at the same time, maintaining desired and/or selected mechanical properties including, for example, straightness, rigidity, torque strength, column strength, tensile strength, kink resistance, and thermal properties such as, for example, thermal stability and thermal stress capacity.

The multi-lumen structure, in some implementations, contains one or more thermal therapy-generating elements and one or more cryotherapy-generating elements for temperature modulation therapy. In addition, the multi-lumen structure may contain a temperature sensor, such as a thermocouple (laser or fiber), to monitor internal temperatures during temperature modulation therapy. The thermal therapy-generating element, in a particular example, is a laser fiber. The laser fiber may be optionally selectively etched with a pattern to achieve a desired lasing pattern. Further to the particular example, the cryotherapy-generating element is a Joule-Thompson cooling apparatus. As discussed in greater detail above (e.g., in relation to FIGS. 6A, 6B, and 8), such a low profile temperature modulation probe may be designed to yield directional energy delivery (e.g., directional heating) or symmetric energy delivery (e.g., symmetric heating). Directional energy delivery, for example, may be achieved by a varying relative temperature while activating both the thermal therapy-generating element and the cryotherapy-generating element, by pulsing (e.g., turning on and off) the thermal therapy-generating element while maintaining activation of the cryotherapy-generating element, and/or by pulsing the cryotherapy-generating element while maintaining activation of the thermal therapy-generating element.

In some embodiments of a laser-based low profile temperature modulation probe designed for LITT, a sapphire lens is utilized for the optimal laser transparency, and robust thermal (e.g., hot and cold) stress capacity. The multi-lumen structure of the low profile probe, in this example, provides comparable modulated lasing and cooling ability when compared with a probe having a larger profile and/or a single lumen.

Figure 13A:
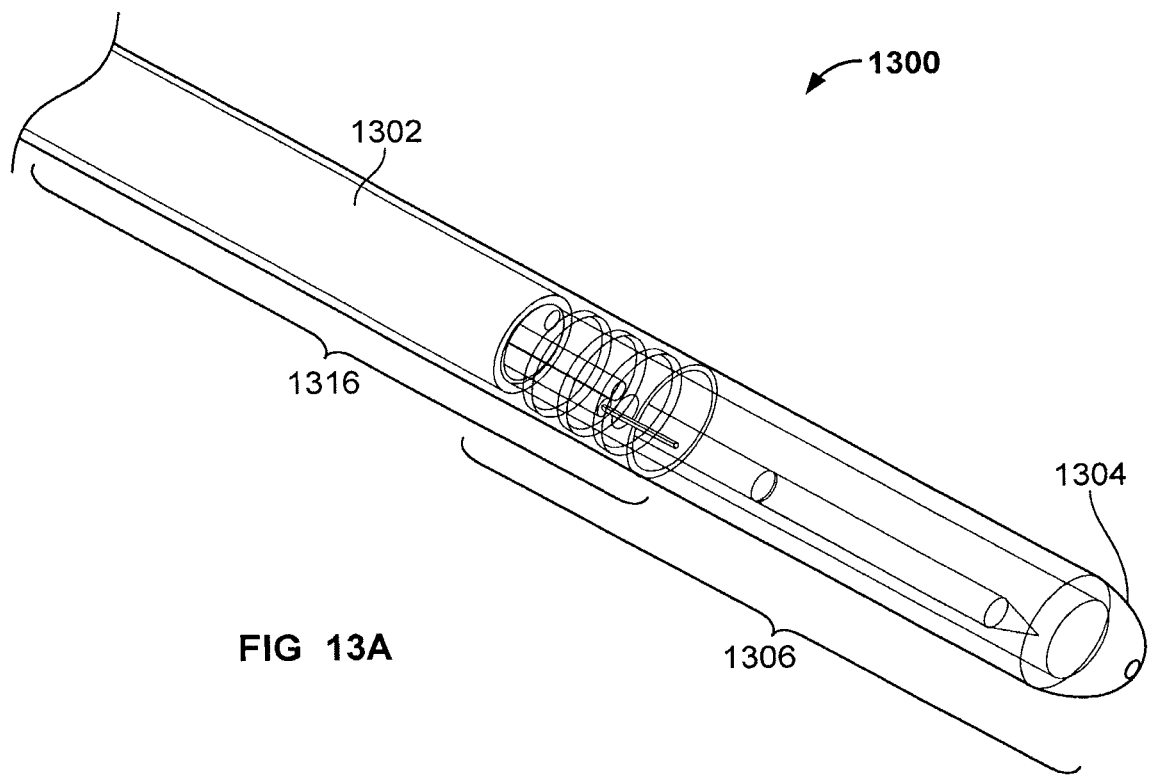
FIGS. 13A and 13B illustrate a first example multi-lumen low profile probe design.
Figure 13B:
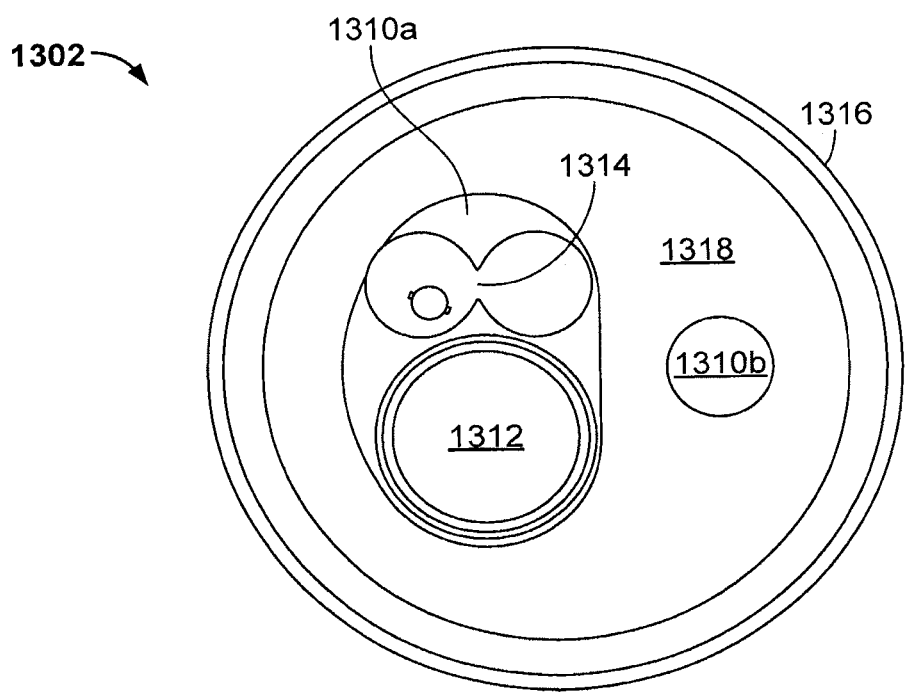

Turning to FIG. 13A, a shaft 1302 of an example low profile probe 1300 includes a multi-lumen rod 1318 (internal cross-sectional detail illustrated in FIG. 13B). The rod 1318, for example, may be composed of a ceramic material selected for strength and break resistance. FIG. 13B illustrates two lumens 1310 defined along the length of the rod 1318, however, it should be understood that more than two lumens may be included in the rod 1318 depending on application. FIG. 13B depicts lumen 1310a as being larger than lumen 1310b, but it should be understood that both lumens 1310 can be approximately the same size. Lumen 1310a may contain, for example, a laser fiber 1312 which delivers laser energy, as well as a thermocouple 1314 (wire or fiber). The thermocouple 1314 may be shrink-wrapped within the lumen 1310a.

Lumen 1310a, in some embodiments, acts as a venting port for a cooling gas (or evaporated cooling liquid) that is delivered via lumen 1310b. A flexible cooling line, for example, may be connected to the distal end of the rod 1318 (not illustrated) and high pressure gas may flow through lumen 1310b, expanding in a tip region 1304 of the low profile probe 1300, and then flowing back through lumen 1310a.

As illustrated in FIG. 13B, the rod 1318, in some embodiments, is covered by a thin-walled polyether ether ketone (PEEK) plastic tube 1316. The PEEK tube 1316, for example, may act as a protective barrier in case the rod 1318 breaks. In the result of a break, the PEEK plastic tube 1316 will keep the probe shaft 1302 connected so it can be completely removed from the patient. Breakage of the rod 1318 may be detected by the low profile probe 1300 and/or a controller thereof, in some examples, based upon unanticipated fluctuations in cooling gas pressure and/or the probe tip temperature. To guard against breakage, material properties and burst pressure ratings of the materials of the rod 1318 may be selected to conform to thermal operating ranges of the particular probe design. Further, in manufacture, the thermal operating ranges of the materials may be verified/validated to prevent breakage or coolant gas leakage during operation. PEEK plastic material is biocompatible which makes it an acceptable material for contact with the patient.

Extending from and integral with the tip 1304 of the low profile probe 1300, in some embodiments, is a lens 1306. The lens 1306, for example, may be composed of machined sapphire. As illustrated, the lens 1306 is bonded to the proximal end of the rod 1318 and is also inserted into the end of the PEEK plastic tube 1316. The energy delivery occurs via the lens 1306. As illustrated, the tip 1304 of the lens 1306 has a torpedo-like nose shape. In another embodiment (not illustrated), the tip 1304 of the lens 1306 has a rounded nose shape.

As discussed above, in the example embodiment illustrated, the components of the probe shaft 1302 are composed of heterogeneous materials (e.g., PEEK and ceramic). In other embodiments, homogenous materials form the components of the probe shaft 1302. Each material may be selected to achieve the desired and/or selected mechanical and/or thermal properties for the low profile probe 1300. In some embodiments, the shaft 1302 and the PEEK tube 1316 are bonded together.

Figure 14A:
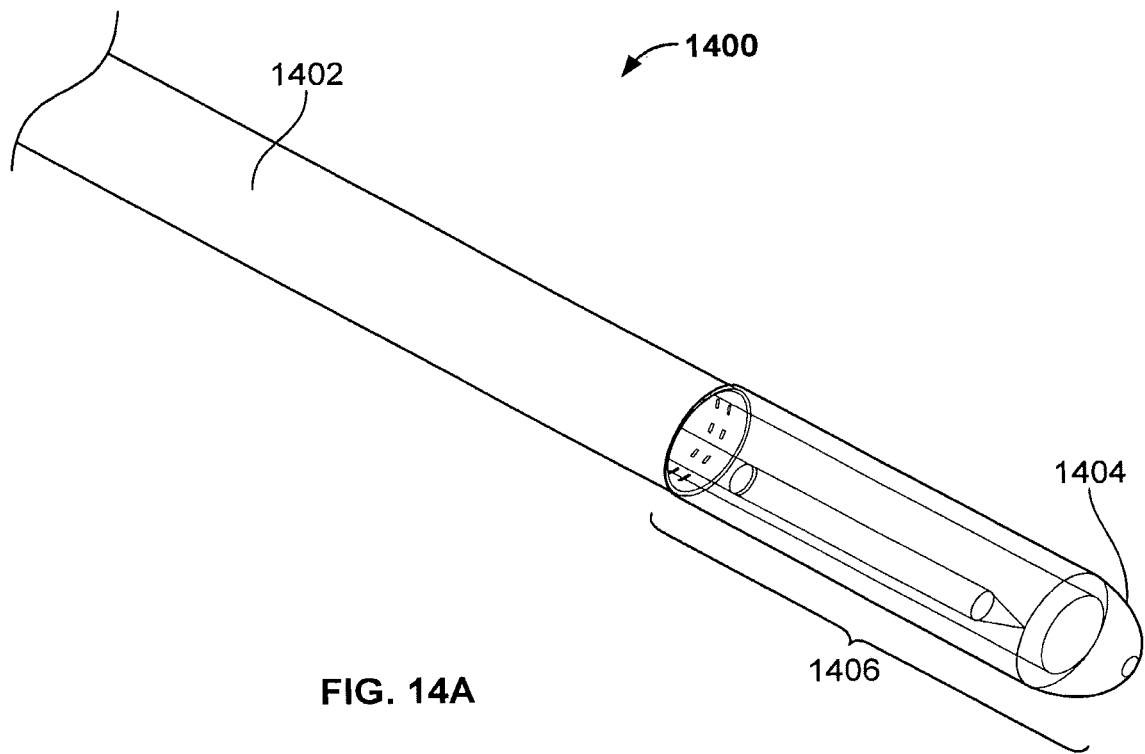
FIGS. 14A and 14B illustrate a second example multi-lumen low profile probe design.
Figure 14B:
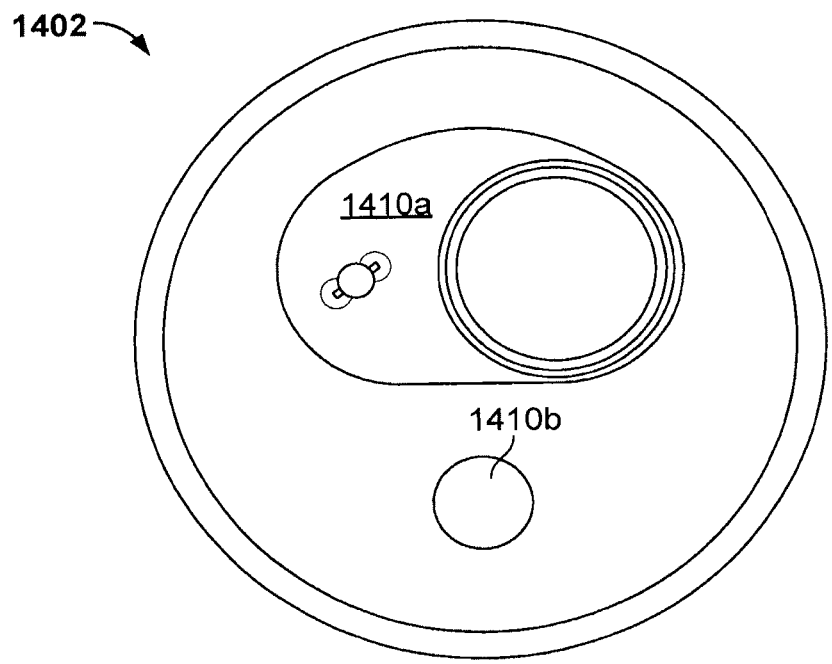

Turning to FIGS. 14A and 14B, a shaft 1402 of a low profile probe 1400 is shown as including a multi-lumen structure (illustrated in a cross-sectional view of the shaft 1402 in FIG. 14B). The shaft 1402, for example, may be configured as a PEEK rod. The style and sizes of the lumens 1410, in some embodiments, are similar to the lumens 1310 of FIG. 13B. To create the low profile probe 1400, in one example, the proximal end of the shaft 1402 may be drilled to allow the distal end of a lens 1406 (e.g., machined sapphire, etc.) to insert and bond. The lens 1406, in this example, may be manufactured with an outer diameter in accordance with the outer and/or inner diameter of the probe shaft 1402. In other embodiments (not illustrated), the probe shaft 1402 is composed of two PEEK rods (i.e., inner and outer shafts).

Figure 15A:
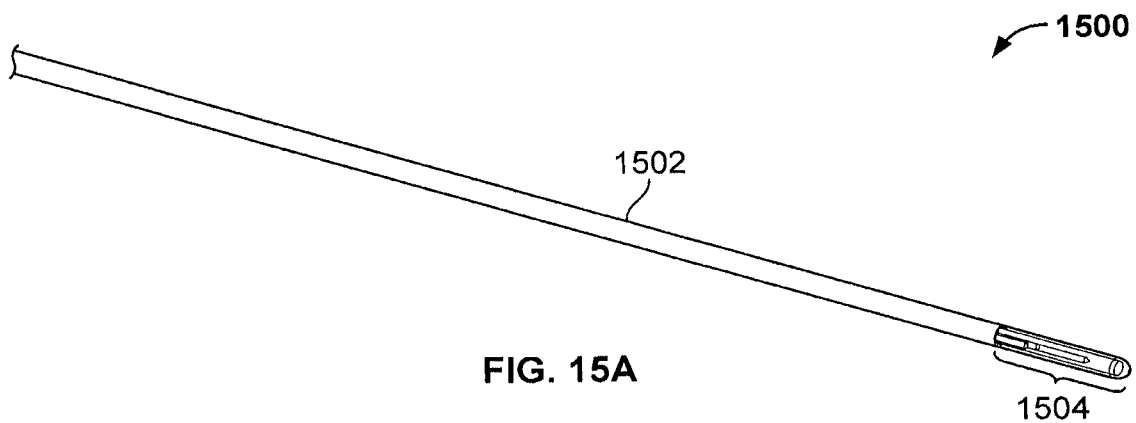
FIGS. 15A through 15C illustrate an example low profile probe design with a multi-layer shaft.
Figure 15B:
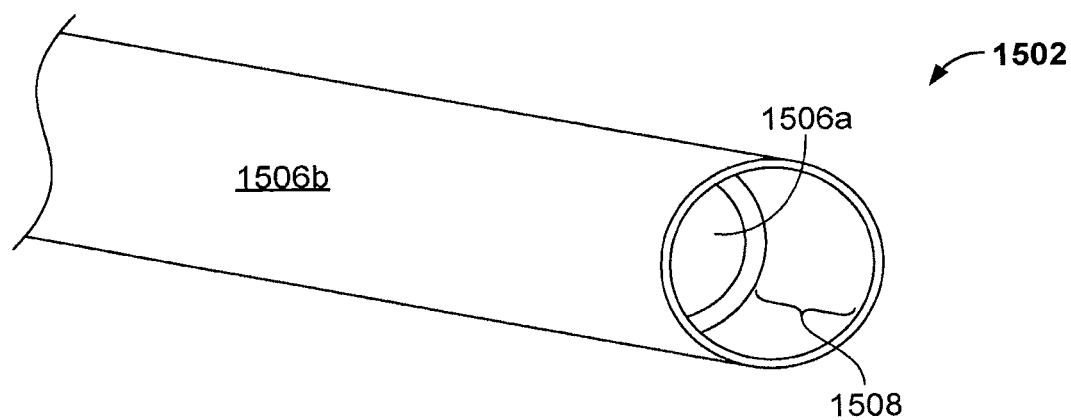
Figure 15C:
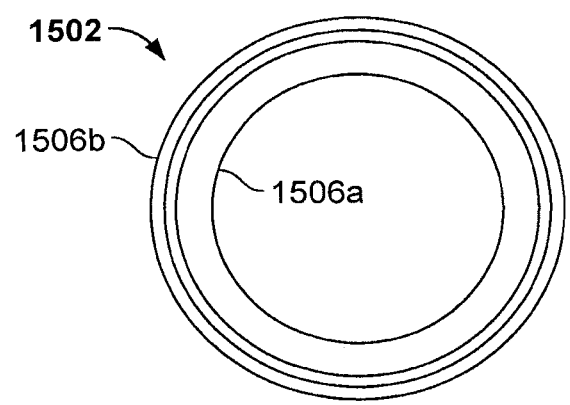

FIGS. 15B and 15C illustrate an example multi-layer single lumen (e.g., open cylinder) probe shaft design of a shaft 1502 of a low profile probe 1500 illustrated in FIG. 15A. As illustrated in FIG. 15C, the shaft 1502 includes an inner layer 1506a and an outer layer 1506b. In other embodiments, a multilayer shaft structure includes three or more layers. The layers may be composed of different or same materials. For example, each of the layers 1506 may be composed of a thermoplastic selected for having a high Young's modulus value. In additional examples, one or more layers may be composed of a non-solid surface material such as, in some examples, a coiled or braided structure. Materials useful in manufacturing the non-solid surface layer, in some examples, include PTFE, PEEK, Polyimide, Polyamide, Polyethylene and PEBAX. In some embodiments, a layer may include winding material made of stainless steel, Nitinol, Nylon or PEEK. Example layers for a probe designed to bend away from skull include a polyimide layer for rigidity (e.g., for a distal portion of a probe shaft) and a PTFE layer for flexibility (e.g., for a proximal portion of a probe shaft,). Other multi-layer probe shaft designs may include a polyimide layer disposed under an etched layer of PTFE for improved bonding characteristics. As illustrated, the inner layer 1506a is thicker than the outer layer 1506b. In other embodiments, the layers may be all of the same thickness, or an inner layer may be thinner than an outer layer. For overall dimensions, in some examples, the design of the shaft 1502 may allow for an outer diameter of a lens 1504 of the probe 1500 to be reduced to about 2.2 mm.

The layers 1506 of the shaft 1502, as illustrated in FIG. 15B, are linearly aligned to create a counterbore 1508 in the proximal end of the shaft 1502. During manufacture of the probe 1500, for example, the distal end of the lens 1504 may be glued to the proximal end of the shaft 1502 at the counterbore 1508. The proximal end of the shaft 1502, as illustrated in FIG. 15B, can be structured such that the lens 1504 can be configured to have both lap join and bud join to the shaft 1502 for secured bond strength. The length of the counterbore, in one example, is controlled match the shoulder length of the lens 1504. In a particular example, the design of the probe 1500 may allow for reduction of a shoulder diameter of the lens 1504 to approximately 2.0 mm.

Turning to FIG. 9, an example laser probe 900 includes a fiber 901 which extends from a tip portion 902 including a light dispersion arrangement connected to a suitable light source at an opposed end of the fiber 901. The light dispersion arrangement, for example, may include a light-directing element at an end of the fiber 901 for directing the light from the laser to the predetermined direction relative to the fiber 901 forming the limited angular orientation within a disk surrounding the axis of the probe 900. The probe 900 further includes, in some embodiments, a support tube 903 in the form of a multi-lumen catheter for the fiber 901 which extends along the fiber 901 from an end 904 of the tube just short of the tip 902 through to a position beyond a fiber drive system configured for controlling the orientation of the fiber within the patient. The fiber drive system, in one example may include a drive motor supported in fixed adjustable position on a stereotaxic frame. The motor may communicate through a control line to a device controller. In general the device controller may receive information from an imaging console such as an MRI console and from position detectors of the motor. The device controller may use this information to control the motor and to operate a power output from the laser, thereby controlling the position and amount of heat energy applied to the part within the body of the patient.

The support tube 903, as illustrated in FIG. 10, includes a first cylindrical duct 904 extending through the tube and two further ducts 905 and 906 parallel to the first duct 904 and arranged within a cylindrical outer surface 907 of the support tube 903.

Returning to FIG. 9, the supporting tube 903 has at its end opposite the outer end 904 a coupling 908 which is coupled to (e.g., molded onto, integrated into, etc.) the end 909 and connects individual supply tubes 910, 911 and 912 each connected to a respective one of the ducts 904, 905 and 906 of FIG. 10. Multi-lumen catheters of this type are commercially available and can be extruded from suitable material to provide the required dimensions and physical characteristics. Thus the duct 904 is dimensioned to closely receive the outside diameter of the fiber 901 so that the fiber 901 can be fed through the duct tube 910 into the duct 904 and can slide through the support tube 903 until the tip 902 is exposed at the end 904.

While tubing may be available which provides the required dimensions and rigidity, in many cases, the tubing is however flexible so that it bends side to side and also will torsionally twist. The support tube 903, in some embodiments, is therefore mounted within an optional stiffening tube or sleeve 914, which extends from an end 915 remote from the tip 902 to a second end 916 adjacent to the tip 902. The second end 916 is however spaced rearwardly from the end 904 of the support tube 903, which in turn is spaced from the tip 902. The distance from the second end 916 to the tip 902 may be arranged to be less than a length of the order of 1 inch. The stiffening tube 914 may be formed of a suitable stiff material that is non-ferro-magnetic so that it is MRI compatible. The support tube 903 may be bonded within the stiffening tube 914 so that it cannot rotate within the stiffening tube 914 and cannot move side to side within the stiffening tube 914. The stiffening tube 914, in some embodiments, is manufactured from titanium, ceramic or other material that can accommodate the magnetic fields of MRI. Titanium generates an artifact within the MRI image. For this reason, the second end 916 may spaced as far as practicable from the tip 902 so that the artifact is removed from the tip 902 to allow proper imagining of the tissues.

In some embodiments, a capsule 920 in the form of a sleeve 921 and domed or pointed end 922 is provided at the second end 916 of the stiffening tube 914. The sleeve 921 may surround the second end 916 of the stiffening tube 914 and be bonded thereto so as to provide a sealed enclosure around the exposed part of the support tube 903. The capsule 920, in some embodiments, is formed of quartz crystal so as to be transparent to allow the escape of the disbursed light energy from the tip 902. The distance of the end of the stiffening tube 914 from the tip 902 may be arranged such that the required length of the capsule 920 does not exceed what can be reasonably manufactured in the transparent material required.

In some embodiments, supply tube 911 is connected to a supply 925 of a cooling fluid and the supply tube 912 is connected to a return collection 926 for the cooling fluid. Thus, the cooling fluid is pumped through the duct 905 and escapes from the end 904 of the support tube 903 into the capsule 920 and then is returned through the duct 906. The cooling fluid can simply be liquid nitrogen allowed to expand to nitrogen gas at cryogenic temperatures and then pumped through the duct 905 and returned through the duct 906 where it can be simply released to atmosphere at the return 926.

In other embodiments, the supply 925 and the return 926 form parts of a refrigeration cycle where a suitable coolant is compressed and condensed at the supply end and is evaporated at the cooling zone at the capsule 920 so as to transfer heat from the tissue surrounding the capsule 920 to the cooling section at the supply end.

The arrangement set forth above allows the effective supply of the cooling fluid in gaseous or liquid form through the ducts 905 and 906 and also effectively supports the fiber 901 so that it is held against side to side or rotational movement relative to the stiffening tube 914. The location of the tip 902 of the fiber 901 is therefore closely controlled relative to the stiffening tube 914. In some embodiments, the stiffening tube 914 is driven by couplings 930 and 931, shown schematically in FIG. 9, of the type driven by reciprocating motor arrangements as set forth in U.S. Pat. No. 7,167,741 to Torchia, entitled "Hyperthermia Treatment and Probe Therefore" and filed Dec. 14, 2001, incorporated herein by reference in its entirety.

Figure 11:
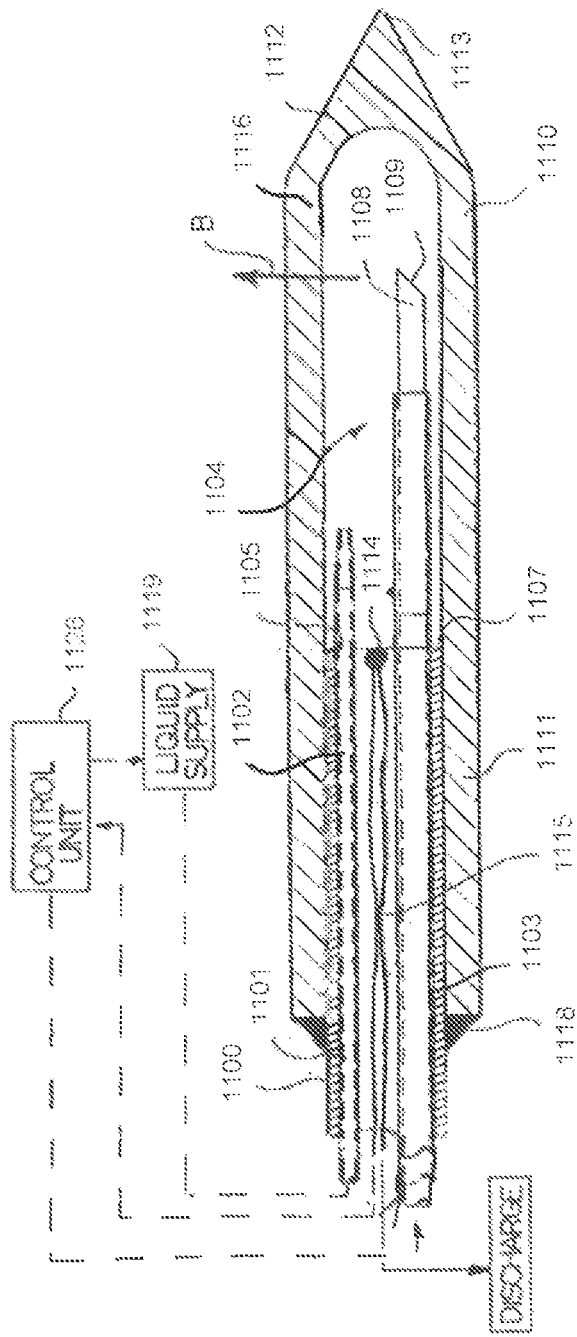
FIG. 11 is a longitudinal cross-sectional view through a further alternative form of probe which provides a flow of cooling fluid to the end of the probe for cooling the surrounding tissue.
Figure 12:
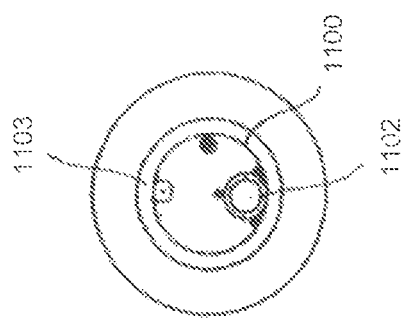
FIG. 12 is a cross-sectional view along the lines 12-12 of FIG. 11.

Turning to FIGS. 11 and 12, an example tip section of an alternative probe is illustrated, in which cooling of the tip section is effected using expansion of a gas into an expansion zone. The tip only is shown as the remainder of the probe and its movements are substantially as previously described.

In some embodiments, the probe includes a rigid extruded tube 1100 of a suitable material, for example titanium, that is compatible with MRI (non-ferromagnetic) and suitable for invasive medical treatment. The probe further includes a smaller cooling fluid supply tube 1102 which may be separately formed, for example by extrusion, and may be attached by adhesive to the inside surface of the outer tube 1100. An optical fiber 1104 is also attached by adhesive to the inside surface the outer tube 1100 so that the fiber 1104 is preferably diametrically opposed to the cooling supply tube 1102.

The cooling supply tube 1102 is swaged at its end to form a neck section 1105, which projects beyond the end of the tube 1101, to form a neck section of reduced diameter at the immediate end of the tube 1102. Thus in manufacture the extruded tube 1101 may be cut to length so as to define a tip end 1107 at which the outer tube terminates in a radial plane. At the tip end 1107 beyond the radial plane, the outer of the inner tube 1102 may be swaged by a suitable tool so as to form the neck section 1105 having an internal diameter, for example, of the order of 0.003 to 0.005 inch.

The fiber 1104, in some embodiments, is attached to the tube 1101 so that a tip portion 1108 of the fiber 1104 projects beyond the tip end 1107 to a chamfered end face 1109 of the fiber. As illustrated, the chamfered end face 1109 is cut at approximately 45 degrees to define a reflective end plane of the fiber 1104.

The tip end 1107, in some embodiments, is covered and encased by an end cap 1110 (e.g., molded quartz) that includes a sleeve portion 1111 closely surrounding the last part of the tube 1100 and extending beyond the tip end 1107 to an end face 1112, which closes the capsule. The end face 1112 is tapered to define a nose 1113, which allows the insertion of the probe to a required location. The end of the tube 1101 may be reduced in diameter so that the capsule has an outer diameter matching that of the main portion of the tube 1101. However in the arrangement shown in FIG. 11 the capsule is formed on the outer surface so that its outer diameter is larger than that of the tube and its inner diameter is approximately equal to the outer diameter of the tube.

A temperature sensor 1114 (e.g., thermocouple, fiber optic thermometer, etc.), in some embodiments, is attached to the inside surface of the outer tube 1100 at the tip end 1107 and includes connecting wires 1115 which extend from the temperature sensor 1114 to a control unit 1126. Thus the temperature sensor 1114 provides a sensor to generate an indication of the temperature at the tip end 1107 within the capsule. A fiber optic thermometer, in one example, may provide the benefit of being fully immune to RF environments and therefore require no electromagnetic compatibility (EMC) filtering. The capsule may be welded to or bonded to the outer surface of the tube as indicated at 1118 so as to form a closed expansion chamber within the capsule beyond the tip end 1107. In some embodiments, an inner surface 1116 of the capsule is of the same diameter as the outer surface of the tube 1100 so that the expansion chamber beyond the end of the tube 1100 has the same exterior dimension as the tube 1100.

The capsule, in some embodiments, is transparent so as to allow the reflected beam of the laser light from the end face 1109 of the fiber 1104 to escape through the transparent capsule in the limited angular direction substantially at right angles to the longitudinal axis of the fiber 1104 and within the axial plane defined by that longitudinal axis.

The tube 1102, in some embodiments, is connected at its end opposite to the neck section 1105 to a fluid supply 1119, which forms a pressurized supply of a suitable cooling fluid such as carbon dioxide or nitrous oxide. The fluid supply 1119, in some embodiments, is controlled by the control unit 1126 to generate a predetermined pressure within the fluid supply to the supply tube 1102 which can be varied so as to vary the flow rate of the fluid through the neck section 1105. The fluid may be supplied at normal or room temperature without cooling. The fluid, in some embodiments, is a gas at this pressure and temperature but fluids that are liquid can also be used provided that they form a gas at the pressures within the expansion chamber and thus go through an adiabatic gas expansion through the restricted orifice into the expansion chamber to provide the cooling effect.

Thus the restricted orifice has a cross-sectional area very much less than that of the expansion chamber and the return duct provided by the inside of the tube 1101. The items that reduce the effective cross-sectional area of the return tube 1101 may include, in some examples, the optical fiber 1104, the supply tube 1102, the thermocouple wires 1115, a shrink tube that fixes the thermocouple wires 1115 to the optical fiber 1104, and/or adhesives used to bond the items into place (e.g., at the inlet of the discharge duct).

Without the area of the adhesives included in the calculation, in some embodiments the exhaust duct area is about 300 times larger than a target size of the delivery orifice diameter (e.g., about 0.004"). When considering the area occupied by the adhesives, the exhaust duct inlet area may be approximately 200 to 250 times larger than the delivery orifice diameter. Considering the manufacturing tolerance range of the supply tube orifice diameter alone, the exhaust duct area may be anywhere between 190 to 540 times larger than the orifice area (without considering the area occupied by adhesives). Therefore, it is estimated that about a 200/1 gas expansion may be required to achieve appropriate cooling. This may allow the gas as it passes into the expansion chamber beyond the neck section 1105, in the particular example, to expand as a gas thus cooling the capsule and the interior thereof at the expansion chamber to a temperature in the range of approximately −20 C to 0 C. This range has been found to be suitable to provide the required level of cooling to the surface of the capsule so as to extract heat from the surrounding tissue at a required rate. Variations in the temperature in the above range can be achieved by varying the pressure from the supply 1119 so that, in one example, the pressure would be of the order of 700 to 850 psi at a flow rate of the order of 5 liters per min. The tube 1102, in some embodiments, has an outside diameter of the order of 0.014 inch OD, while a tube 1103 has a diameter of the order of 0.079 inch. Thus a discharge duct for the gas from the expansion chamber is defined by the inside surface of the tube 1100 having a flow area which is defined by the area of the tube 1100 minus the area taken up by the tube 1102 and the fiber 1104. This allows discharge of the gas from the expansion chamber defined within the capsule at a pressure of the order of 50 psi so that the gas can be simply discharged to atmosphere if inert or can be discharged to an extraction system or can be collected for cooling and returned to the fluid supply 1119 if economically desirable. Tip cooling may be necessary, in certain uses, for optimum tissue penetration of the laser or heating energy, reduction of tissue charring and definition of the shape of the coagulated zone. The gas expansion thus provides an arrangement that is suitable for higher power densities required in this probe to accommodate the energy supplied by the laser heating system.

The tip portion 1108 of the fiber 1104, in some embodiments, is accurately located within the expansion zone since it is maintained in fixed position within the capsule by its attachment to the inside surface of the outer tube 1100. The fiber 1104 may be located forwardly of the tip end 1107 sufficiently that the MRI artifact generated by the tip end 1107 is sufficiently removed from the plane of the fiber tip portion 1108 to avoid difficulties in monitoring the temperature within the plane of the fiber tip portion 1108. The outlet orifice of the tube 1102 may also be located forwardly of the tip end 1107 so as to be located with the cooling effect generated thereby at the plane of the fiber tip portion 1108 or end face 1109 thereof.

The end face 1109, in some embodiments, is located within the expansion chamber so that it is surrounded by the gas with no liquid within the expansion chamber. Thus, in practice there is no condensate on the end face 1109 nor any other liquid materials within the expansion chamber that would otherwise interfere with the reflective characteristics of the end face 1109.

The end face 1109, in some embodiments, is coated with a reflective coating such as a dual dielectric film. This may provide a reflection at the two wavelengths of the laser light used as a visible guide beam and as the heat energy source, such as He—Ne and Nd:YAG respectively. An alternative coating is gold, which can alone provide the reflections at the two wavelengths.

The arrangement of the probe of FIGS. 11 and 12 provides excellent MRI compatibility both for anatomic imaging as well as MR thermal profiling. Those skilled in the art will appreciate that the cooling system in accordance with the above description may also be used with circumferential fibers having point-of-source energy.

In some embodiments, in operation, the temperature within the expansion zone is monitored by the temperature sensor 1114 so as to maintain that temperature at a predetermined temperature level in relation to the amount of heat energy supplied through the fiber 1104. Thus the pressure within the fluid supply is varied to maintain the temperature at that predetermined set level during the hyperthermic process.

As described previously, the probe may moved to an axial location within the volume to be treated and the probe may rotated in steps so as to turn the heating zone generated by the beam B into each of a plurality of segments within the disk or radial plane surrounding the end face 1109. Within each segment of the radial plane, heat energy is supplied by the beam B that is transmitted through the capsule into the tissue at that segment. The heat energy is dissipated from that segment both by reflection of the light energy into adjacent tissue and by conduction of heat from the heated tissue to surrounding tissue. As stated previously, those skilled in the art will appreciate that the probe used with the cooling system in accordance with the description above may include circumferential fibers having point-of-source energy.

The surface of the capsule, in some embodiments, is cooled to a temperature so that it acts to extract heat from the surrounding tissue at a rate approximately equal to the dissipation or transfer of heat from the segment into the surrounding tissue. Thus the net result of the heating effect is that the segment alone is heated and surrounding tissue not in the segment required to be heated is maintained without any effective heating thereon, that is no heating to a temperature which causes coagulation or which could otherwise interfere with the transmission of heat when it comes time to heat that tissue in another of the segments. In this way when a first segment is heated to the required hyperthermic temperature throughout its extent from the probe to the peripheral surface of the volume, the remaining tissues in the areas surrounding the probe are effectively unheated so that no charring or coagulation has occurred which would otherwise prevent dissipation of heat and in extreme cases completely prevent penetration of the beam B.

Thus when each segment in turn has been heated, the probe can be rotated to the next segment or to another segment within the same radial plane and further heating can be effected of that segment only.

In practice in one example, the laser energy can be of the order of 12 to 15 watts penetrating into a segment having an angle of the order of 60 to 80 degrees to a depth of the order of 1.5 cm. In order to achieve this penetration without causing heating to the remaining portions of the tissue not in the segment, cooling of the outside of the capsule to a temperature of the order of −5.degree. C. may be required.

Figure 17:
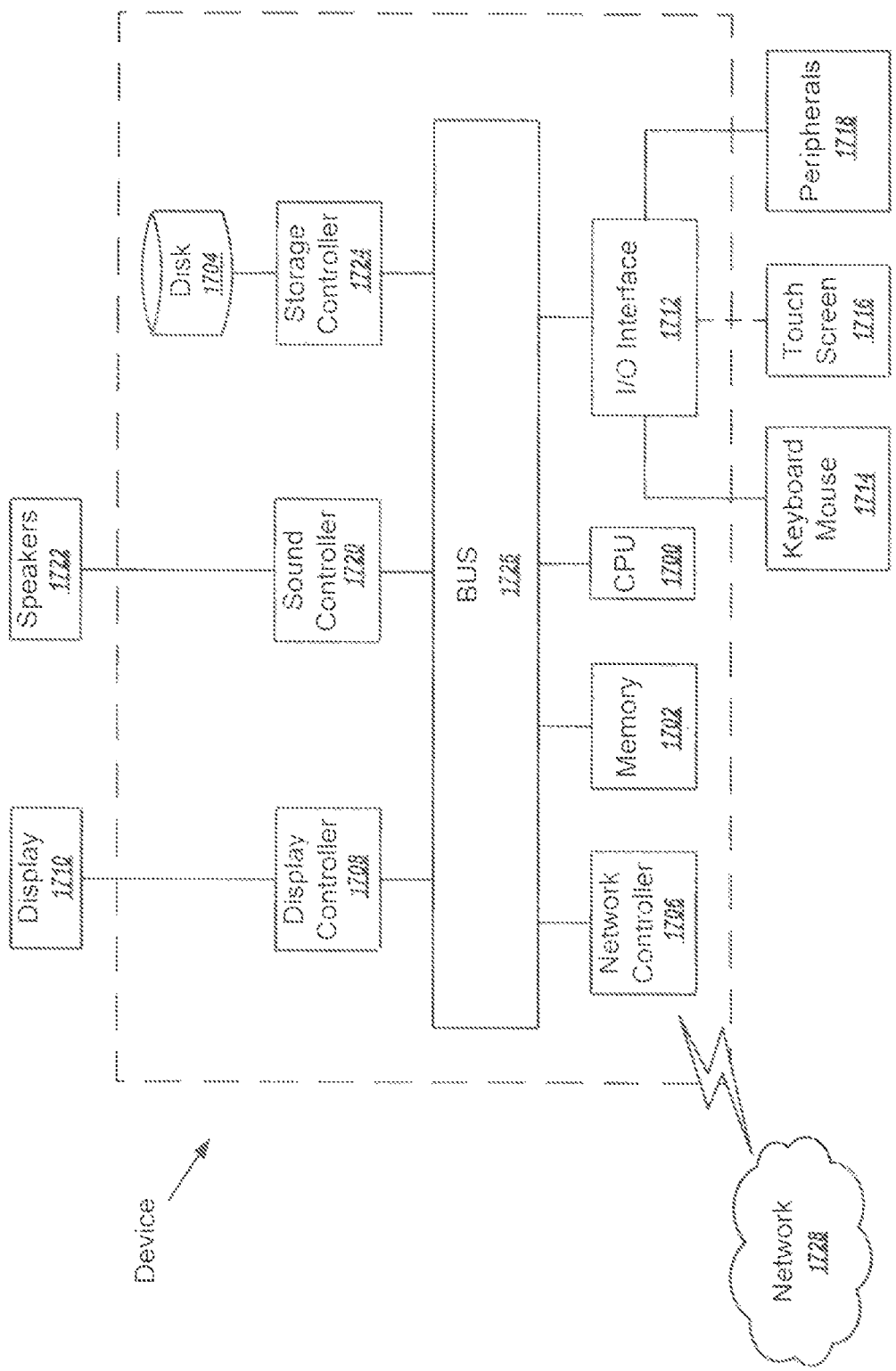
FIG. 17 is a block diagram of an example computing system hardware design.

Next, a hardware description of the computing device, mobile computing device, or server according to exemplary embodiments is described with reference to FIG. 17. In FIG. 17, the computing device, mobile computing device, or server includes a CPU 1700 which performs the processes described above. The process data and instructions may be stored in memory 1702. These processes and instructions may also be stored on a storage medium disk 1704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device, mobile computing device, or server communicates, such as a server or computer.

Further, a portion of the claimed advancements may be provided as a utility application, background daemon, or component of an operating system, or combination thereof, executing in conjunction with CPU 1700 and an operating system such as Microsoft Windows 7, UNIX, Solaris, LINUX, Apple MAC-OS and other systems known to those skilled in the art.

CPU 1700 may be a Xenon or Core processor from Intel of America or an Opteron processor from AMD of America, or may be other processor types that would be recognized by one of ordinary skill in the art. Alternatively, the CPU 1700 may be implemented on an FPGA, ASIC, PLD or using discrete logic circuits, as one of ordinary skill in the art would recognize. Further, CPU 1700 may be implemented as multiple processors cooperatively working in parallel to perform the instructions of the inventive processes described above.

The computing device, mobile computing device, or server in FIG. 17 also includes a network controller 1706, such as an Intel Ethernet PRO network interface card from Intel Corporation of America, for interfacing with network 1728. As can be appreciated, the network 1728 can be a public network, such as the Internet, or a private network such as an LAN or WAN network, or any combination thereof and can also include PSTN or ISDN sub-networks. The network 1728 can also be wired, such as an Ethernet network, or can be wireless such as a cellular network including EDGE, 3 G and 4 G wireless cellular systems. The wireless network can also be Wi-Fi, Bluetooth, or any other wireless form of communication that is known.

The computing device, mobile computing device, or server further includes a display controller 1708, such as a NVIDIA GeForce GTX or Quadro graphics adaptor from NVIDIA Corporation of America for interfacing with display 1710, such as a Hewlett Packard HPL2445w LCD monitor. A general purpose I/O interface 1712 interfaces with a keyboard and/or mouse 1714 as well as a touch screen panel 1716 on or separate from display 1710. General purpose I/O interface also connects to a variety of peripherals 1718 including printers and scanners, such as an OfficeJet or DeskJet from Hewlett Packard.

A sound controller 1720 is also provided in the computing device, mobile computing device, or server, such as Sound Blaster X-Fi Titanium from Creative, to interface with speakers/microphone 1722 thereby providing sounds and/or music.

The general purpose storage controller 1724 connects the storage medium disk 1704 with communication bus 1726, which may be an ISA, EISA, VESA, PCI, or similar, for interconnecting all of the components of the computing device, mobile computing device, or server. A description of the general features and functionality of the display 1710, keyboard and/or mouse 1714, as well as the display controller 1708, storage controller 1724, network controller 1706, sound controller 1720, and general purpose I/O interface 1712 is omitted herein for brevity as these features are known.

One or more processors can be utilized to implement various functions and/or algorithms described herein, unless explicitly stated otherwise. Additionally, any functions and/or algorithms described herein, unless explicitly stated otherwise, can be performed upon one or more virtual processors, for example on one or more physical computing systems such as a computer farm or a cloud drive.

Reference has been made to flowchart illustrations and block diagrams of methods, systems and computer program products according to implementations of this disclosure. Aspects thereof are implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, some implementations may be performed on modules or hardware not identical to those described. Accordingly, other implementations are within the scope that may be claimed.

What is claimed is:

1. A system for performing temperature modulation therapy to a tissue with an interstitial probe, the system comprising:
    an interstitial probe, comprising a shaft region, a tip region, at least one thermal therapy-generating element for thermal therapy emission via the tip region, and at least one cryotherapy-generating element for cryogenic therapy emission via the tip region;
    processing circuitry; and
    a memory having instructions stored thereon, wherein the instructions, when executed by the processing circuitry, cause the processing circuitry to, while the interstitial probe is positioned proximate a tissue:
        determine a thermal dose for effecting thermal therapy treatment based on a present position of the interstitial probe,
        identify, based at least in part upon the thermal dose, a modulation pattern comprising at least one cycle of lower thermal output interspersed between two higher thermal outputs, wherein a higher thermal output corresponds to activation of a first thermal therapy element of the at least one thermal therapy-generating element for a first time interval and the lower thermal output corresponds to activation of a first cryogenic therapy element of the at least one cryogenic therapy element for a second time interval,
        activate, at the present position of the interstitial probe, temperature modulation therapy by the interstitial probe utilizing the identified modulation pattern for applying the thermal dose to the tissue,
        during the application of the thermal dose via the modulation therapy, monitor at least one temperature of the tissue,
        identify a difference between a goal temperature corresponding to the thermal dose and the at least one temperature of the tissue, and
        responsive to identifying the difference, alter the modulation pattern, wherein altering the modulation pattern comprises altering at least one of a) a length of the first time interval, b) a length of the second time interval, c) an emission level of the first thermal therapy-generating element during the first time interval, d) an emission level of the first thermal therapy-generating element during the second time interval, e) an emission level of the first cryotherapy-generating element during the first time interval, and f) an emission level of the first cryotherapy-generating element during the second time interval.

2. The system of claim 1, wherein altering the modulation pattern comprises selecting a new modulation pattern of a plurality of pre-set modulation patterns.

3. The system of claim 1, wherein identifying the difference between the goal temperature and the at least one temperature of the tissue comprises identifying a measured tissue temperature differs from the goal temperature by at least a threshold amount.

4. The system of claim 1, wherein altering the modulation pattern comprises lowering an overall tissue temperature towards the goal temperature to avoid cellular damage during thermal therapy.

5. The system of claim 1, wherein a goal thermal dose profile comprises the goal temperature, wherein the goal thermal dose profile is related to the thermal dose.

6. The system of claim 1, wherein the instructions, when executed, cause the processing circuitry to identify, based at least in part upon the thermal dose, the modulation pattern further comprise instructions to cause the processing circuitry to identify the modulation pattern based at least in part upon a desired effect upon the tissue, wherein the desired effect comprises at least one of altering normal biological function, altering abnormal biological function, and disrupting a blood-brain barrier.

7. The system of claim 1, wherein the instructions, when executed, cause the processing circuitry to identify, based at least in part upon the thermal dose, the modulation pattern further comprise instructions to cause the processing circuitry to identify the modulation pattern based at least in part upon a type of secondary treatment to be applied at the region of interest, wherein the type of secondary treatment comprises at least one of a drug treatment, a chemical treatment, a biochemical treatment, and a radiation treatment.

8. The system of claim 1, wherein monitoring the at least one temperature of the tissue comprises performing image-based thermography of the tissue.

9. The system of claim 1, further comprising a controller remotely located to the probe, wherein the controller comprises at least a portion of the processing circuitry.

10. The system of claim 1, further comprising a flexible umbilical sheath portion permanently affixed to the shaft region, wherein the flexible umbilical sheath portion includes at least one interface for supplying one of energy, cooling fluid, cooling gas, heating fluid, and heating gas to the shaft region.

11. The system of claim 1, wherein the first time interval is different from the second time interval.

12. The system of claim 1, wherein the first time interval is similar to the second time interval.

13. The system of claim 1, wherein at least one of the two higher thermal outputs corresponds to a simultaneous activation of a cryogenic therapy element for at least part of the first time interval.

14. The system of claim 1, wherein the thermal dose comprises at least one of the following: a goal temperature, a goal thermal dose profile, or a goal energy dose profile.

* * * * *